(12) United States Patent
Nojiri et al.

(10) Patent No.: US 7,426,062 B2
(45) Date of Patent: Sep. 16, 2008

(54) SIGNAL OUTPUT APPARATUS, IMAGE FORMING APPARATUS AND INFORMATION OUTPUT APPARATUS

(75) Inventors: Hidetoshi Nojiri, Kanagawa (JP);
Masatake Akaike, Kanagawa (JP);
Norio Kaneko, Kanagawa (JP);
Takehiko Kawasaki, Kanagawa (JP);
Koichiro Nakanishi, Kanagawa (JP);
Naoyo Gemma, Kanagawa (JP);
Toshitsugu Morimoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 982 days.

(21) Appl. No.: 10/760,293

(22) Filed: Jan. 21, 2004

(65) Prior Publication Data
US 2005/0087010 A1    Apr. 28, 2005

Related U.S. Application Data

(63) Continuation-in-part of application No. 10/216,745, filed on Aug. 13, 2002, now abandoned.

(30) Foreign Application Priority Data

| | | |
|---|---|---|
| Aug. 21, 2001 | (JP) | ............................. 2001-250385 |
| Feb. 28, 2002 | (JP) | ............................. 2002-052984 |
| May 8, 2002 | (JP) | ............................. 2002-132809 |
| Jul. 25, 2002 | (JP) | ............................. 2002-216642 |
| Jan. 21, 2003 | (JP) | ............................. 2003-012798 |

(51) Int. Cl.
*G06K 15/02* (2006.01)
*H04N 1/23* (2006.01)
*G01N 3/30* (2006.01)

(52) U.S. Cl. ..................... 358/3.24; 358/406; 73/12.01; 347/153

(58) Field of Classification Search ................ 358/1.12, 358/3.24, 300, 504, 406, 498, 296; 73/12.01, 73/12.09, 12.11, 12.12, 12.13; 347/105, 347/106, 153, 155, 158, 292, 264
See application file for complete search history.

(56) References Cited

U.S. PATENT DOCUMENTS 4,519,245 A    5/1985    Evans (Continued)

FOREIGN PATENT DOCUMENTS

CN    11-20964    4/1997

(Continued)

*Primary Examiner*—Scott A Rogers
(74) *Attorney, Agent, or Firm*—Fitzpatrick, Cella, Harper & Scinto

(57) ABSTRACT

A signal output apparatus comprises an impact applying unit applying an impact to a sheet from the outside thereof, and a detection unit outputting a signal by the impact. An apparatus for determining the type of sheet comprises an impact applying unit applying an impact to a sheet from the outside thereof, and a detection unit outputting a signal by the impact, wherein the type of the sheet is determined based on the signal from the detection unit. An image forming apparatus comprises an impact applying unit applying an impact to a sheet from the outside thereof, and a detection unit outputting a signal by the impact. A method for determining the type of sheet comprises the steps of applying an impact to a sheet from the outside thereof, outputting a signal from a detection unit by the applying step, and determining the type of sheet based on the signal. An apparatus carries out the method for determining the type of sheet. An information output apparatus used in an image forming apparatus comprises an impact applying unit applying an impact to a target from the outside thereof, and a detection unit outputting information by the impact.

25 Claims, 59 Drawing Sheets

U.S. PATENT DOCUMENTS

| | | |
|---|---|---|
| 4,688,423 A | 8/1987 | Orkosalo |
| 4,847,638 A | 7/1989 | Moriyama |
| 4,864,851 A | 9/1989 | Haughton |
| 4,866,984 A | 9/1989 | Houghton |
| 4,970,895 A | 11/1990 | Houghton et al. |
| 4,991,432 A | 2/1991 | Houghton et al. |
| 5,136,202 A | 8/1992 | Carenzo et al. |
| 5,295,673 A | 3/1994 | Torisawa et al. |
| 5,361,332 A | 11/1994 | Yoshida et al. |
| 5,499,807 A | 3/1996 | Nakamura et al. |
| 5,533,399 A | 7/1996 | Gibson et al. |
| 5,606,113 A | 2/1997 | Sheen et al. |
| 5,934,140 A | 8/1999 | Jackson et al. |
| 6,026,681 A | 2/2000 | Wunderer et al. |
| 6,097,497 A | 8/2000 | McGraw |
| 6,276,776 B1 | 8/2001 | Umezawa et al. |
| 6,291,829 B1 | 9/2001 | Allen et al. |
| 6,866,263 B2 | 3/2005 | Kawasaki |
| 7,239,817 B2 * | 7/2007 | Kaneko et al. .............. 73/12.13 |
| 2003/0053089 A1 | 3/2003 | Nojiri et al. |
| 2004/0059534 A1 | 3/2004 | Nojiri |
| 2004/0094458 A1 | 5/2004 | Akaike |
| 2004/0139783 A1 | 7/2004 | Sakai |
| 2004/0187579 A1 | 9/2004 | Yabuta et al. |

FOREIGN PATENT DOCUMENTS

| | | |
|---|---|---|
| JP | 55-22166 | 2/1980 |
| JP | 55-33116 | 3/1980 |
| JP | 55-033116 | 3/1980 |
| JP | 57-148231 | 9/1982 |
| JP | 61-212744 | 9/1986 |
| JP | 04-251772 | 9/1992 |
| JP | 07-53095 | 2/1995 |
| JP | 07-303723 | 11/1995 |
| JP | 08-50073 | 2/1996 |
| JP | 09-40216 | 2/1997 |
| JP | 10-6607 | 1/1998 |
| JP | 10-152245 | 6/1998 |
| JP | 10-329964 | 12/1998 |
| JP | 11-314443 | 11/1999 |
| JP | 2000-301805 | 10/2000 |
| JP | 2001-328748 | 11/2001 |

* cited by examiner

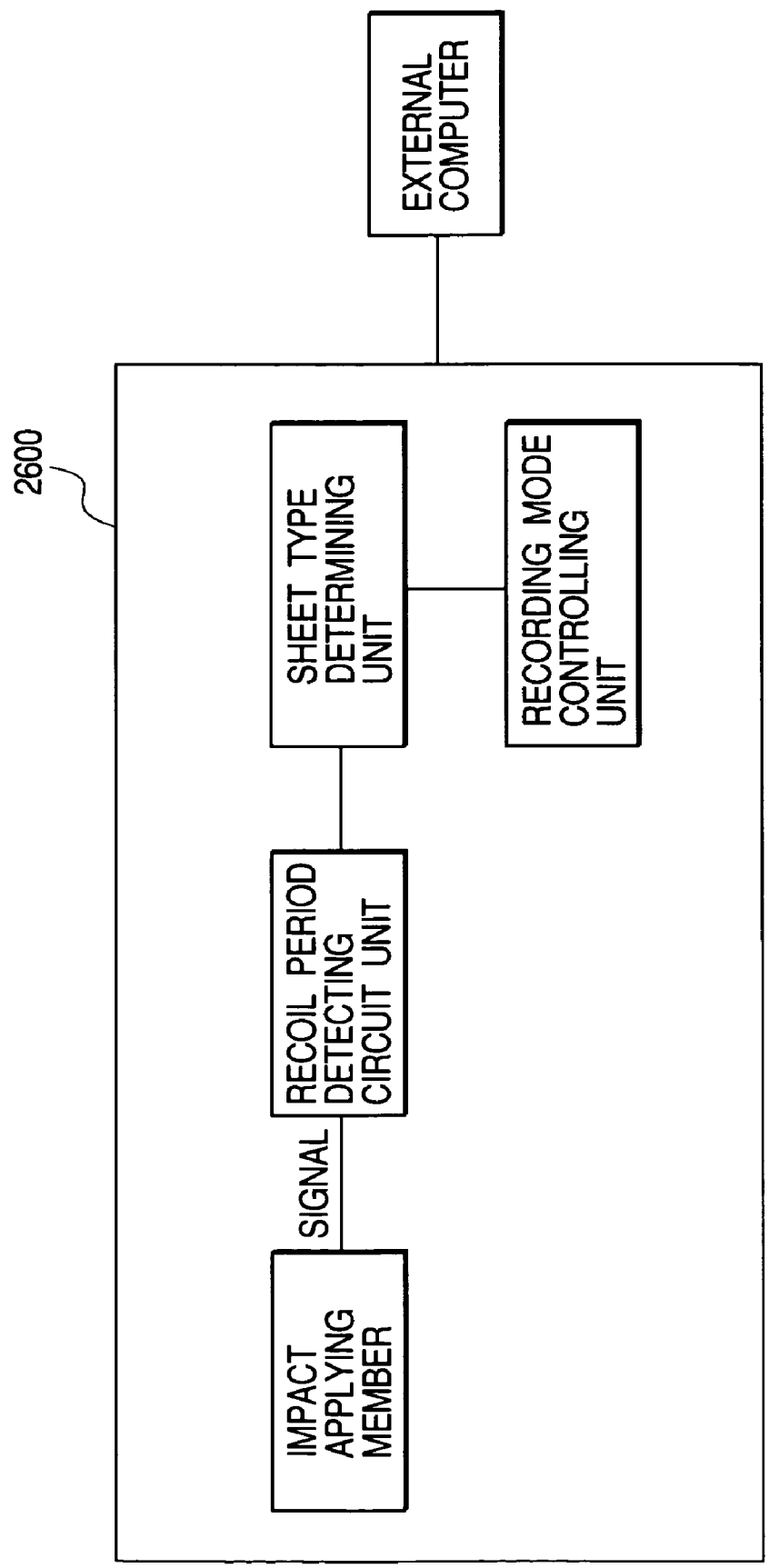

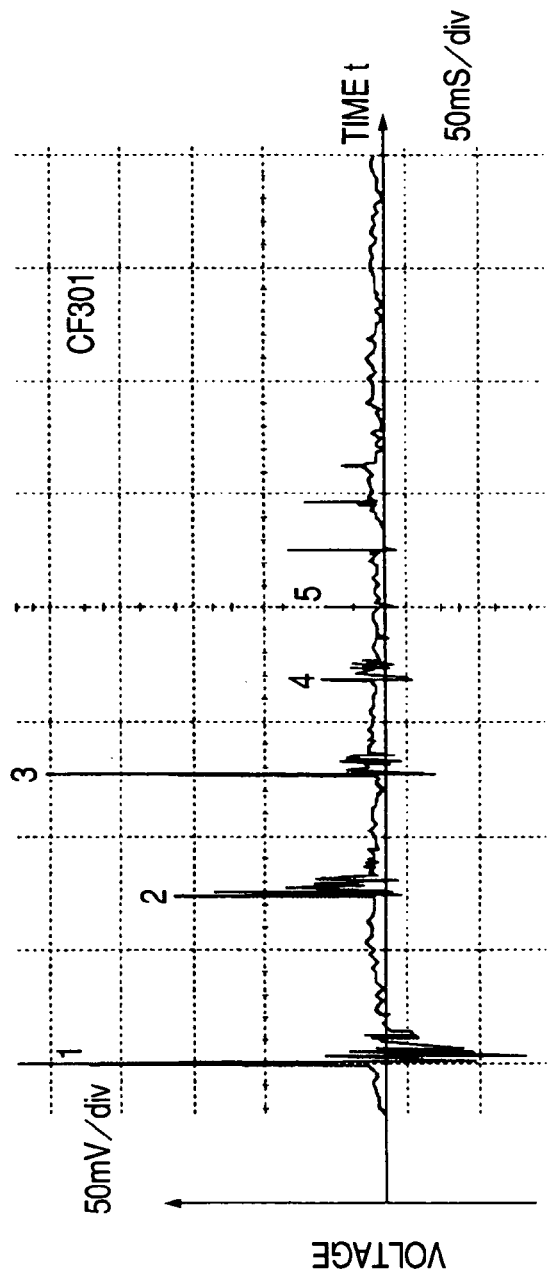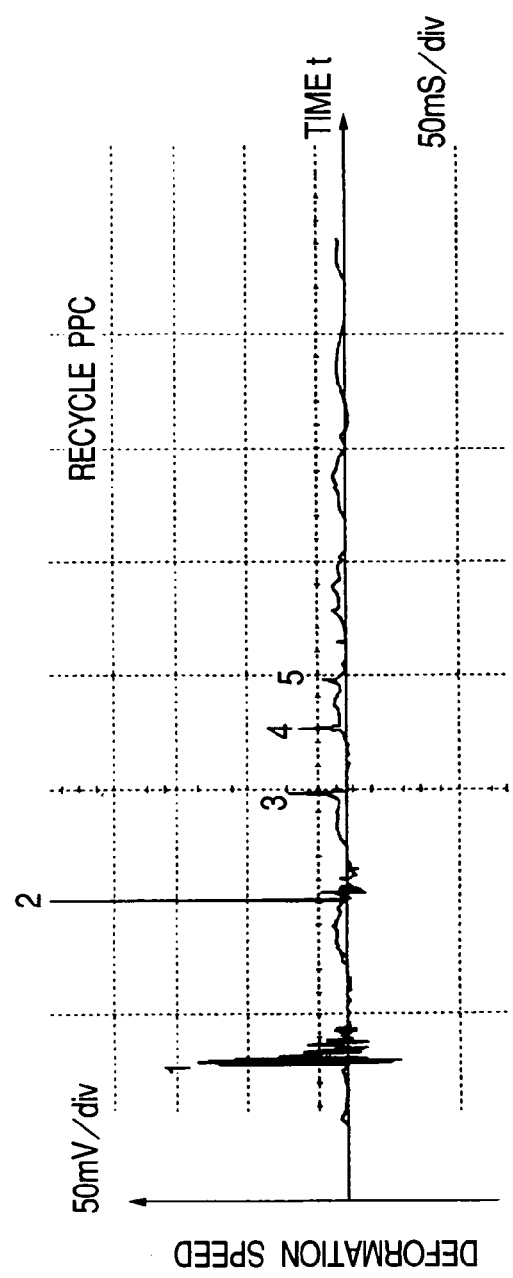
FIG. 37A
FIG. 37B

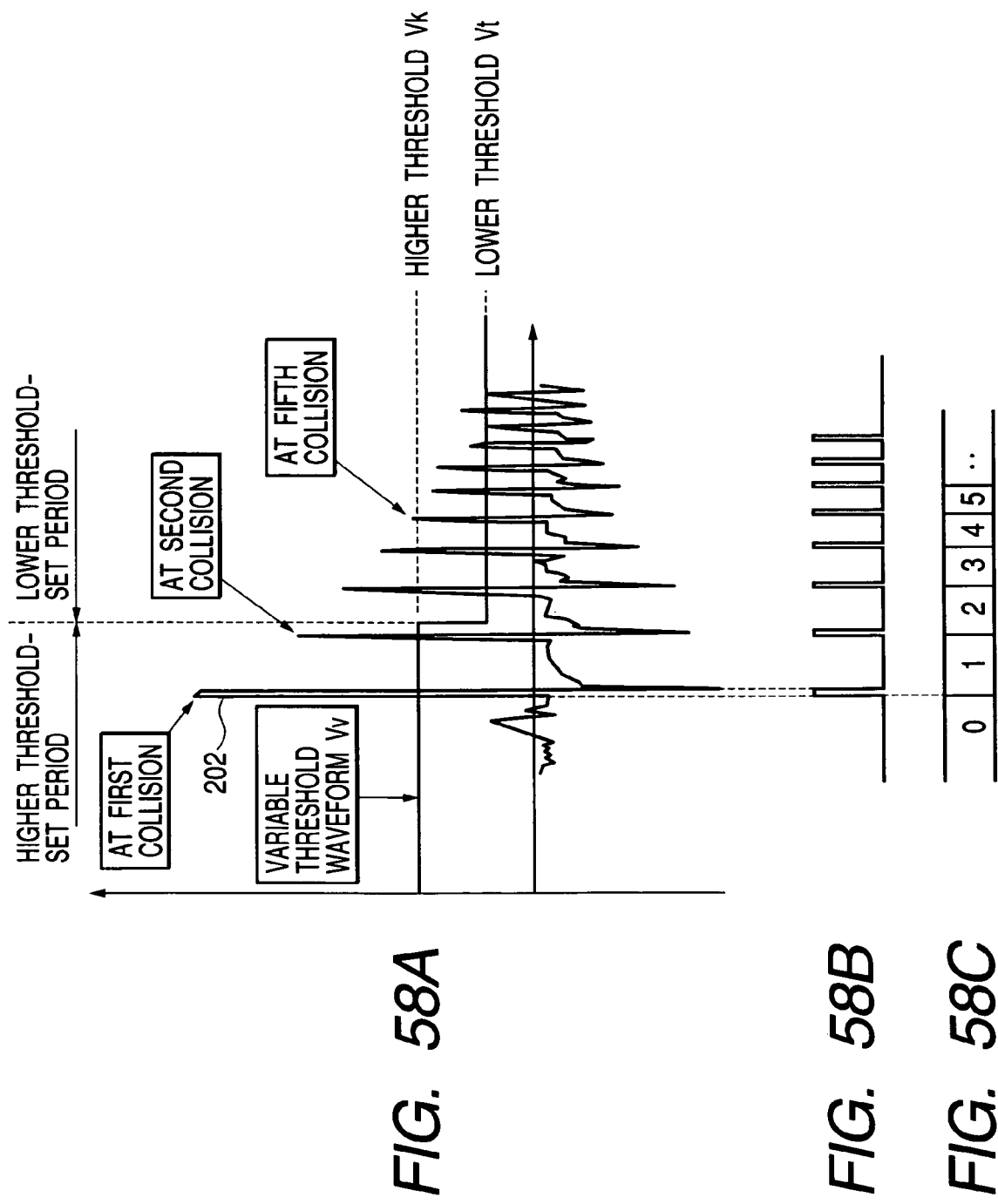

SIGNAL OUTPUT APPARATUS, IMAGE FORMING APPARATUS AND INFORMATION OUTPUT APPARATUS

This is a continuation-in-part application of U.S. patent application Ser. No. 10/216,745 filed Aug. 13, 2002.

BACKGROUND OF THE INVENTION

1. Field of the Invention

The present invention relates to a signal output apparatus. The present invention also relates to a detection apparatus detecting information about sheet materials for use in an image forming apparatus, a sheet conveying apparatus and the like, and an image forming apparatus comprising such a detection apparatus, and so on.

2. Related Background Art

In recent years, the types of printing sheets are being diversified for use in an image-forming apparatus such as copying machines and printers. With such trend, apparatuses for identifying the type of a sheet material are attracting attention.

A method of determining the type of sheet material is described in Japanese Patent Application Laid-Open No. H11-314443 (U.S. Pat. No. 6,097,497).

In the technique disclosed in the above patent publications, a numeral code or a symbol is attached preliminarily as a mark to the sheet material (hereinafter referred to as a "marking system"), and the information of the mark is read by a sensor equipped in a printer or a copying machine to select an optimum printing mode by utilizing the read information.

In the aforementioned marking system, the type of the sheet cannot be identified without the code or symbol attached thereto.

The present invention intends to provide an apparatus for identifying the type of a sheet material, being capable of outputting information on the type of the sheet material regardless of the presence or absence of the marked information attached to the sheet material.

SUMMARY OF THE INVENTION

The signal output apparatus according to the present invention is characterized by comprising an impact applying unit applying an impact to a sheet material from the outside, and a detection unit outputting a signal by the impact.

The detection unit comprises a piezoelectric element, or is provided on an elastic deformable member.

Also, the detection unit can be provided on the bottom face of the recess of a substrate having a recess.

The impact may be applied to a sheet material when the sheet material is in a static state.

Also, a configuration is possible such that the impact applying unit can be transited from the state in which it does not contact the sheet material to the state in which it contacts the sheet material at the time when the impact applying unit applies an impact.

The apparatus for determining the type of sheet material according to the present invention is characterized by comprising an impact applying unit applying an impact to a sheet material from the outside, and a detection unit outputting a signal by the impact, and determining the type of sheet material based on the signal from the detection unit.

The determination can be made using information about sheet materials stored in advance and the signal from the detection unit. The determination can be made using the peak value, the number of peaks or the time interval between peaks for the output signal from the detection unit.

Also, the determination can also be made using the nth peak value and (n+.alpha.)th peak value (.alpha. represents a natural number) of the out put signal from the detection unit, or using the recoil period of the impact applying unit.

Also, the image forming apparatus according to the present invention is characterized by comprising an impact applying unit applying an impact to a sheet material from the outside, and a detection unit outputting a signal by the impact. Thereby, the type of sheet material can be determined based on the signal from the detection unit to define conditions for items to be controlled.

In the case where the image forming apparatus forms images by discharging an ink, the amount of ink to be discharged is controlled, for example. Also, in the case where the image forming apparatus forms images using toners, the temperature of the sheet material is controlled. In addition thereto, items to be controlled include conditions for conveying the sheet material (conveyance speed, pressure between conveying rollers, space between rollers), paper feed conditions for sorting and feeding paper (sorter), conditions for drying the sheet material after formation of images and conditions about staples. Furthermore, whether printing is possible or not may be determined based on the signal from the detection unit. Also, an alarm (e.g. an alarm indicating that the print mode designated by the user or defined automatically does not match the type of sheet material) may be issued to the user based on the signal from the detection unit without setting conditions for the item to be controlled.

In addition, the method of determining the type of sheet material is characterized by comprising a first step of applying an impact to a sheet material from the outside, a second step of outputting a signal from the detection unit by the first step, and a third step of determining the type of sheet material based on the signal.

In addition, the system determining the type of sheet material, according to the present invention, is characterized by applying an impact to a sheet material from the outside, thereby causing a signal to be outputted from the detection unit in the image forming apparatus, and determining the type of sheet material based on the signal by a computer set inside the image forming apparatus or a computer connected to the image forming apparatus outside the image forming apparatus.

Also, the information output apparatus according to the present invention is an information output apparatus for use in the image forming apparatus, characterized by comprising an impact applying unit applying an impact to a target from the outside, and a detection unit outputting information by the impact.

The apparatus for determining the type of sheet of the present invention comprises an impact applying unit for impacting a sheet material, a detection unit for outputting a signal regarding the impact, a pulse-generating means for generating a pulse in response to a signal outputted from the detection unit at or above a prescribed threshold level, and a threshold-setting means for setting the prescribed threshold.

In successive rebounding of an impacting member on a sheet material, the output signal from the detection unit attenuates. In some cases, owing to the attenuation of the signal, no pulse is generated by the pulse-generating means even when the impacting member collides against the sheet material. In the present invention, since a threshold-setting means is provided in the apparatus for determining the type of sheet to adjust the threshold, pulses can be generated corresponding to prescribed times of the collisions. The time intervals between the pulses (between an n-th pulse and an m-th pulse (m>n)) contain information on the type of the sheet material. Therefore, the types of the sheet material can be identified by comparison of the pulse intervals with the preliminarily memorized information. Incidentally the information includes the judgment of the presence or absence of the sheet material.

The apparatus for determining the type of sheet of the present invention comprises an impact applying unit to be allowed to rebound from a sheet material, a detection unit for sensing the position of the impact applying unit, a pulse-generating means for generating a pulse on collision of the impact applying unit against the sheet material in response to an output signal from the detection unit at or above a prescribed threshold level, a period-computing means for computing an interval between the pulses generated by the pulse-generating means, identifying means for identifying the type of the sheet material on the basis of the computation by the period-computing means, and a threshold-setting means for setting the prescribed threshold at a suitable level; and the threshold-setting means sets a threshold for the second or later collision of the impacting means.

According to an aspect of the present invention, there is provided an apparatus for determining the type of sheet comprising:

an impact applying unit for applying an impact force against a sheet material, a detection unit for detecting attenuation of the applied impact force on the sheet material and outputting a signal regarding the attenuation, a pulse-generating means for generating a pulse in response to a signal outputted from the detection unit at or above a prescribed threshold level, a threshold-setting means for setting the threshold, and an identifying means for identifying a type of the sheet material according to the outputted pulse generated by the pulse-generating means in comparison with the set threshold, wherein the threshold-setting means sets the threshold according to the form of the output signal.

According to another aspect of the present invention, there is provided an image-forming apparatus comprising a apparatus for determining the type of sheet, and an image-forming section for forming an image under conditions corresponding to the identified sheet material, wherein the apparatus for determining the type of sheet comprises an impact applying unit for applying an impact against a sheet material, a detection unit for outputting a signal in response to the impact, a pulse-generating means for generating a pulse in response to a signal outputted from the detection unit at or above a prescribed threshold level, and a threshold-setting means for setting the threshold in correspondence with intensity of the signal.

According to still another aspect of the present invention, there is provided a method of identifying a type of a sheet material comprising the steps:

applying an impact force to the sheet material;

detecting attenuation of the applied impact force by the sheet material;

outputting a signal in correspondence with the detected force;

generating a pulse when the signal is at or above a prescribed threshold;

setting the prescribed threshold; and identifying the type of the sheet material based on the output of the pulse generated according to the threshold set above, wherein the threshold is set according to the output state of the signal.

BRIEF DESCRIPTION OF THE DRAWINGS

FIG. 16 illustrates the signal output apparatus according to the present invention;

FIGS. 37A and 37B show examples of the output signal according to the present invention;

FIG. 58A is a waveform chart showing comparison of a signal outputted from a piezoelectric element with a threshold value;

FIG. 58B shows a waveform chart of the pulse outputted on the basis of the comparison;

FIG. 58C shows detection of the pulse intervals;

FIG. 66A is a waveform chart showing comparison of a signal outputted from a piezoelectric element with a threshold value. FIG. 66B shows the pulse outputted on the basis of the comparison. FIG. 66C shows detection of the pulse intervals; FIG. 67A is a waveform chart showing comparison of a signal outputted from a piezoelectric element with a threshold value. FIG. 67B shows a waveform chart of the pulse outputted on the basis of the comparison. FIG. 67C shows detection of the pulse intervals.

DESCRIPTION OF THE PREFERRED EMBODIMENTS

The present invention will specifically be described below.

The signal output apparatus according to the present invention will be described in the first embodiment, the method and apparatus for determining the type of sheet material will be described in the second embodiment, the apparatus and system capable of determining the type of sheet material according to the present invention will be described in the third embodiment, and the information output apparatus according to the present invention will be described in the fourth embodiment.

First Embodiment

Signal Output Apparatus

Apparatus Configuration and Principle/Action

Figure 1:
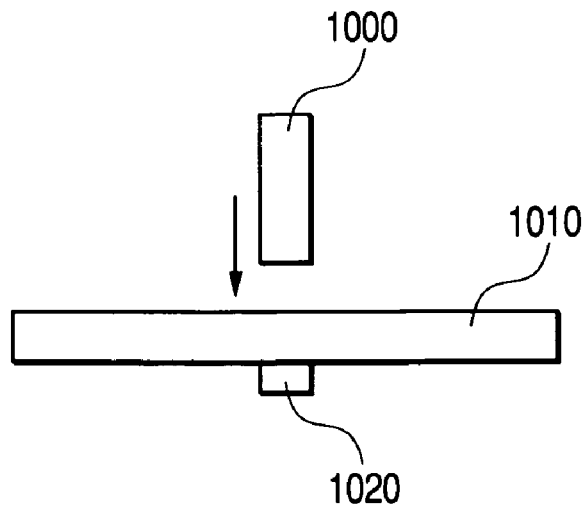
FIG. 1 illustrates a signal output apparatus according to the present invention.

The signal output apparatus according to the present invention comprises an impact applying unit, and a detection unit outputting a signal by the impact. FIG. 1 is a schematic diagram of the signal output apparatus according to the present invention. Reference numeral 1000 in this figure denotes the impact applying unit applying an impact to a sheet material 1010 from the outside. Reference numeral 1020 denotes the detection unit outputting a signal by the impact. The present invention originates from the fact that the inventor has found that the signal outputted from the detection unit varies depending on the type of sheet material. Furthermore, it is thought that variation of the output signal depending on the type of sheet material is mainly based on differences in mechanical properties such as stiffness of sheet materials.

Sheet Material

Sheet materials include papers serving as image formable materials, paper leafs, plastic sheets, recording media (including disk type-recording media such as CD-ROM), and printed matters and paper money on which images have been formed.

In the present invention, the target to which an impact to be applied is not particularly limited as long as information about the state and type of the target can be obtained by the signal from the detection unit.

Impact

The impact in the present invention is an external force applied from the outside of a sheet material to the sheet material on a temporary basis. The external force as the impact in the present invention is applied to a portion but not the whole of the length of the sheet material in an aspect of a specific dimension of the sheet material, e.g. a direction of conveying the sheet material. In other words, the impact is an external force applied to the sheet material instantly or as a continuous pulse (e.g. rapping or striking force), which is not a supersonic force or the like, but a mechanical force. The impact may be applied one time or intermittently several times to the sheet material. The impact may be applied several times using rebounds of the impact applying unit.

In the case where the impact is applied several times and where several kinds of forces are applied, a plurality of data can be obtained, thus improving accuracy of identification. In such a case, it is preferable that after the impact once applied is sufficiently attenuated, or after it is reduced to a predetermined level, a second impact is applied.

Materials through which the impact is applied to the sheet material may include solid materials (metals, plastics, alloys, ceramics, etc.), gaseous materials (air, nitrogen, carbon dioxide), liquid materials (water, inks), gel materials, powders and mixtures thereof, and these materials may be used to apply the impact. The impact may be applied using gravity, or an electric, mechanical, magnetic or electromagnetic force. For example, a spring and solenoid may be used, and a conveying roller in the image forming apparatus, a roller for forwarding the sheet material and so forth may be used.

The impact applying unit 1000 and the sheet material 1010 may be transited from the state in which they do not contact each other to the state in which they contact each other in applying the impact. In such a transition, a distance between the impact applying unit 1000 and the sheet material 1010 varies during the impact. Alternatively, the impact may be applied to the sheet material 1010 in the state in which the impact applying unit 1000 and the sheet material 1010 previously contact each other. For achieving the application of impact in the latter case, the impact is applied to a specified portion of the impact applying unit contacting the sheet material for example. Alternatively, an electromagnetic force may be exerted on the impact applying unit.

In the case where both the impact applying unit and detection unit contact the sheet material when the impact is applied, the distance between the impact applying unit and the detection unit changes when the impact is applied. Specifically, the distance is reduced when the impact is applied. For the distance to change, it is only required that any one of the impact applying unit and the detection unit should be moved relative to the other, and there are cases where both of them are moved and where one is fixed while the other is moved. When the detection unit is mounted on the impact applying unit, they make as one body the distance from the sheet vary.

Furthermore, FIG. 1 shows an impact applied to the sheet material 1010 in the vertical direction, but the impact may be applied slantingly to the sheet material. Alternatively, the impact may be applied to the edge face of the sheet material.

As a matter of course, the impact applying unit may be some distance from the sheet material when the impact is applied as long as the impact can be applied. It is, for example, the case where a gas or liquid is blown to apply an impact.

The impact may be applied when the sheet material is being moved (e.g. conveyed), but the impact is applied preferably when the sheet material is in the static state. The "static state" of the sheet material mentioned herein is a state when the sheet material is not being conveyed, or a state when conveyance of the sheet material is temporarily stopped at some midpoint, which means the state in which the sheet material substantially remains at rest. However, when the sheet material is not in the static state (for example, it is being conveyed), the impact may be applied to include information about the surface of the sheet material in the output signal.

Detection Unit

The detection unit 1020 outputs a signal by the impact to the sheet material.

The detection unit does not detect an impact (action) itself applied to the sheet material, but it detects directly or indirectly a force by reaction from the sheet material or a force attenuated by the sheet material. For example, the detection unit may detect a sound (acoustic wave) generated when the impact is applied to the sheet material.

The signal outputted from the detection unit 1020 is a signal based on the dynamical properties or mechanical properties of the sheet material. The mechanical properties include, for example, the rigidity, Young's modulus, density, weight, basis weight (basis weight is the weight per square meter of the sheet material), and thickness of the sheet material, or irregularities on the surface of the sheet material.

Forms of outputted signals include electric signals such as voltage, current, resistance, electric capacity and impedance, and optical signals. Elements for outputting electric signals include, for example, piezoelectric elements. In the case where the piezoelectric element is used for the detection unit, it is preferable that a protective part is provided on at least one face of the piezoelectric element to prevent it from being damaged by the impact.

The detection unit may be configured such that the signal is outputted only with the impact, or may be configured such that the output signal of the base is changed by the impact. If the detection is configured such that the signal is outputted only with the impact, the detection unit 1020 can be mounted on the impact applying unit 1000.

It is desirable that the detection unit and the sheet material contact each other at least at the time when the impact is applied. Therefore, the configuration is also possible such that the sheet material and the detection unit are prevented from contacting each other just before the impact is applied, and they contact each other at the time when the impact is applied.

If taking advantage of the detection unit outputting a signal by impact, the aforementioned signal output apparatus may be used as an impact detecting apparatus.

Specific Configurations of Impact Applying Unit and Detection Unit

The specific configurations of the impact applying unit and the detection unit will now be described.

The sheet material is held between a first member and a second member so that an impact is applied to the sheet material. The sheet material may be pinched between the members the moment when the impact is applied thereto, or the impact may be applied to the sheet material pinched between the members in advance.

Figure 4:
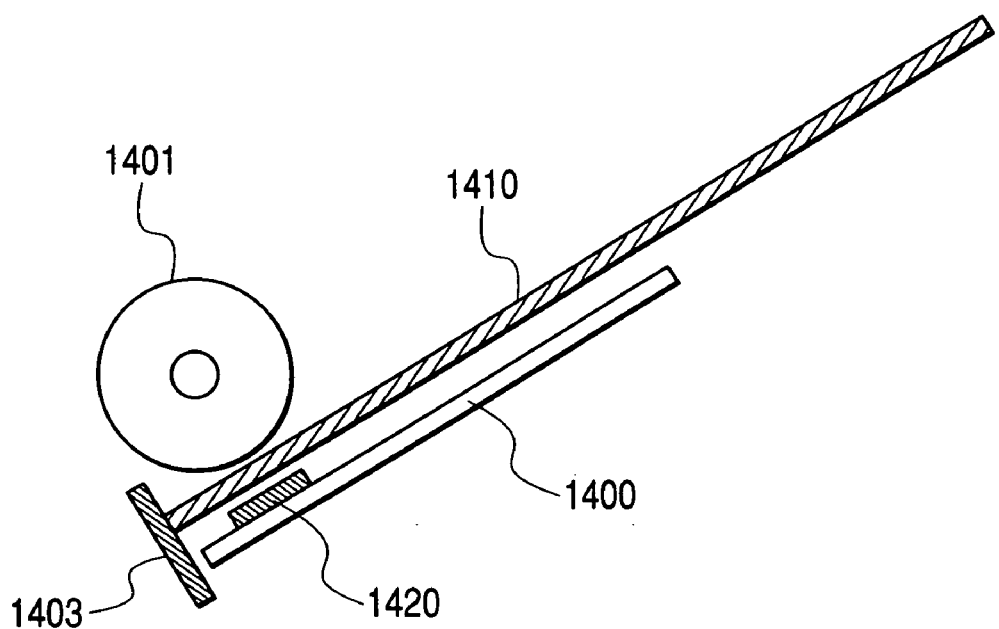
FIG. 4 illustrates the signal output apparatus according to the present invention.

For applying the impact to the sheet material in this specific configuration, any member may be mechanically bumped against the sheet material, or the piezoelectric element and the like may be used. The image forming apparatus such as a printer usually has a pinching guide portion 1400 (corresponding to the first member) and a pinch roller portion 1401 (corresponding to the second member) for feeding or conveying the sheet material as shown in FIG. 4, and thus an example of the configuration of this signal output apparatus in which they are used to apply an impact will be described here. In this figure, reference numeral 1410 denotes the sheet material, and reference numeral 1420 denotes the detection unit outputting a signal by the impact. The detection unit 1420 has an electrode 1422 provided on the piezoelectric element 1421, and the signal from the electrode is outputted from this detection unit.

In the image forming apparatus in which the sheet material is pinched between the first member such as the pinching guide portion and the second member such as the pinch roller portion for feeding or conveying the sheet, for example, an impact of magnitude equal to or greater than 1 g/cm$^2$ and smaller than 500 g/cm$^2$ can be applied instantly to the sheet material.

When the impact is applied to the sheet material 1410, a voltage signal is outputted from the electrode of the piezoelectric element 1420 as the output signal from the detection unit, thus making it possible to determine the type of sheet material using the output signal.

In the case where the sheet material is located between the impact applying unit and the detection unit, the detection unit may be placed on the bottom face of the recess of a substrate having a recess. In this case, the surface of the detection unit placed in the recess may or may not be protruded from the surface of the substrate. In the case where the surface of the detection unit is protruded, it should be protruded to a lesser extent so that the conveyance of the sheet material is not hindered. It is preferable that the depth of the recess or the force exerted on the sheet material by the impact applying unit is set so that the sheet material and the detection unit contact each other at the time when the impact applying unit is collided against the sheet material. In this case, a signal reflecting distortion (deformation) of the sheet material can be obtained. In this way, the configuration such that the sheet material and the detection unit are prevented from contacting each other before the impact is applied, and they contact each other at the time when the impact is applied represents a preferred form.

Arrangement of Detection Unit

The case where the piezoelectric element is used for the detection unit will be described below.

The piezoelectric element to be mounted on the detection unit may be provided on at least one of the first member and second member, or may be placed both the members. Therefore, the configuration is possible such that the sheet material is pinched between the detection unit placed on the first member and the second member (i.e. configuration such that the detection unit receives an impact through the sheet material). Also, the impact applying unit and the detection unit can be placed on the same side of the sheet material. In this way, the location of the detection unit comprising the piezoelectric element is not particularly limited as long as the impact can be detected by the piezoelectric element. That is, the location of the detection unit is not particularly limited as long as it is located so that the electric signal is outputted from the detection unit by the impact. Therefore, the impact may be applied by the first member itself having mounted thereon the piezoelectric element constituting the detection unit, or the impact may be applied by the second member, or the impact may be applied by both the first and second members.

For example, there is the case where the impact is applied for selectively conveying only one piece of sheet material, and in this case, the impact may be used as the impact in the present invention.

Figure 6A:
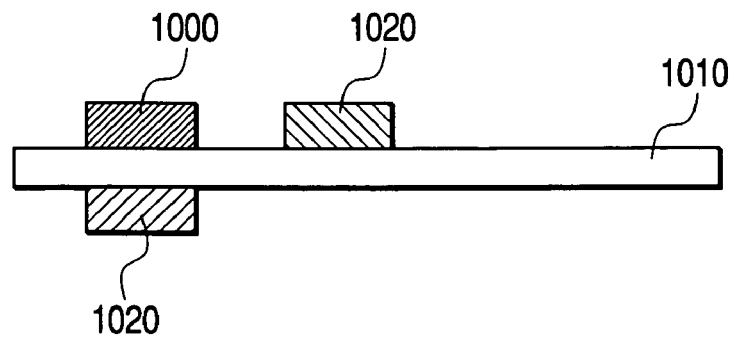
FIGS. 6A, 6B and 6C illustrate the signal output apparatus according to the present invention.
Figure 6B:
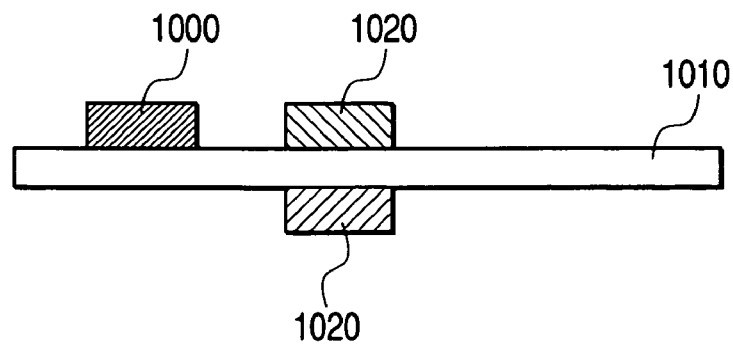
Figure 6C:
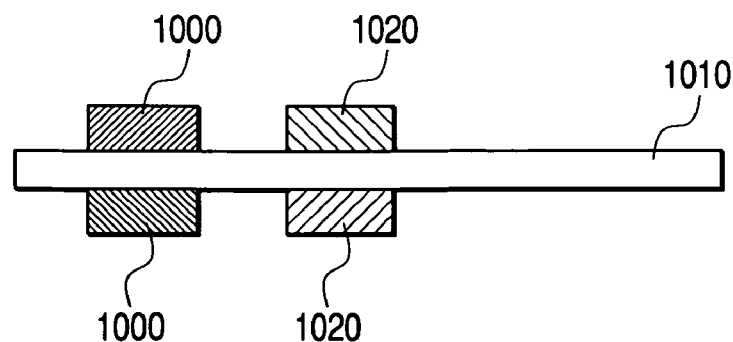

Examples of using a plurality of detections are shown in FIGS. 6A to 6C. In this figure, reference numeral 1000 denotes the impact applying unit, reference numeral 1020 denotes the detection unit in a schematic manner. FIG. 6A shows an example in which detection units are placed at two locations, respectively: one located opposite to the impact applying unit 1000 via the sheet material 1010, and the other located on the same side as the face of the sheet material with the impact applying unit mounted thereon.

FIG. 6B shows an example in which two detection units are equally distanced from the impact applying unit 1000 in the lateral direction.

FIG. 6C shows an example in which the impact applying unit and the signal output unit are placed in such a manner that they are opposite to each other with the sheet material therebetween.

In this way, if the impact applying unit and the signal output unit are placed in such a manner that they are opposite to each other with the sheet material therebetween, and if the impact applying units (or signal output units) are placed in such a manner that they are opposite to each other with the sheet material therebetween, the signal by the impact can be detected as a change in capacitance of the sheet material. Also, data about capacitance (electrostatic capacity) of the sheet material can be obtained.

When applying an impact to one side of the sheet, it is possible to acquire information concerning the surface of the sheet from a detection unit located at the side. In such a case, another detection unit located at the other side of the sheet can detect a signal propagated in the sheet to acquire information concerning structure, material, thickness, etc. of the sheet.

Also, if detection units are each placed on the front side and the back side of the sheet material, information about the front and back sides of the sheet material, for example information about which is front side and which is the back side, can be obtained. In this case, the impact may be applied to both sides of the sheet material to obtain such information from each output signal.

Also, a plurality of detection units may be arranged in one dimension or may be arranged in two dimensions. If the detection units are arranged along the width of the sheet material, the width of the sheet material can be detected. If the detection units are arranged in two dimensions in such a manner that they are arranged along the length as well as the width of the sheet material, the size of the sheet material can be detected.

In addition, if the detection unit is also mounted on the impact applying unit itself, it is not necessary to arrange the impact applying unit and the detection unit through the sheet material, which is preferred in terms of degree of freedom for design of the apparatus.

Material of Detection Unit

The above described piezoelectric element may comprise an inorganic material or organic material having piezoelectric properties, which may be, for example, an inorganic material such as PZT (titanic lead zirconate) and PLZT, $BaTiO_3$, and PMN-PT "$Pb(Mg_{1/3}Nb_{2/3})O_3$-$PbTiO_3$" or an organic piezoelectric material. By using the piezoelectric element for the detection unit, the voltage signal can be outputted from the detection unit without using a power source. Furthermore, for example a piezo resistance material (such as semiconductor) may be used for the detection unit instead of the piezoelectric element.

Any matter illustrated in First Embodiment can be applied to every embodiment and working example described below.

Second Embodiment

Method and Apparatus for Determining the Type of Sheet Material

Figure 2:
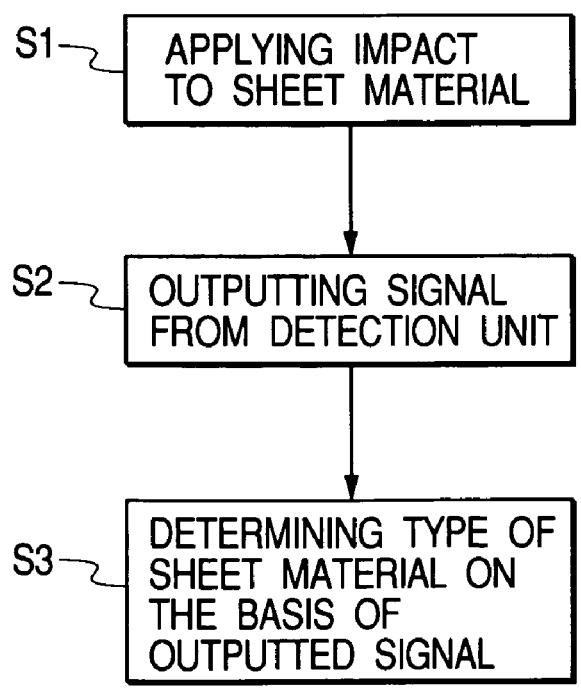
FIG. 2 is a flow chart for determining the type of sheet material according to the present invention.

The method and apparatus for determining the type of sheet material using the signal output apparatus of the present invention will now be described. FIG. 2 shows a general outline of the method for determining the type of sheet material of the present invention.

Method for Determining the Type

First, a predetermined impact is applied to a sheet material (S1).

How the impact is applied is not particularly limited as long as the predetermined impact is applied. A signal is outputted from the detection unit by the impact (S2), and the type of sheet material is determined based on the outputted signal (S3).

The determination is made by storing in advance information of the output signal for each type of sheet material and information into which the above information is processed, and comparing the stored information (hereinafter referred to as "data table") with the signal.

Figure 3:
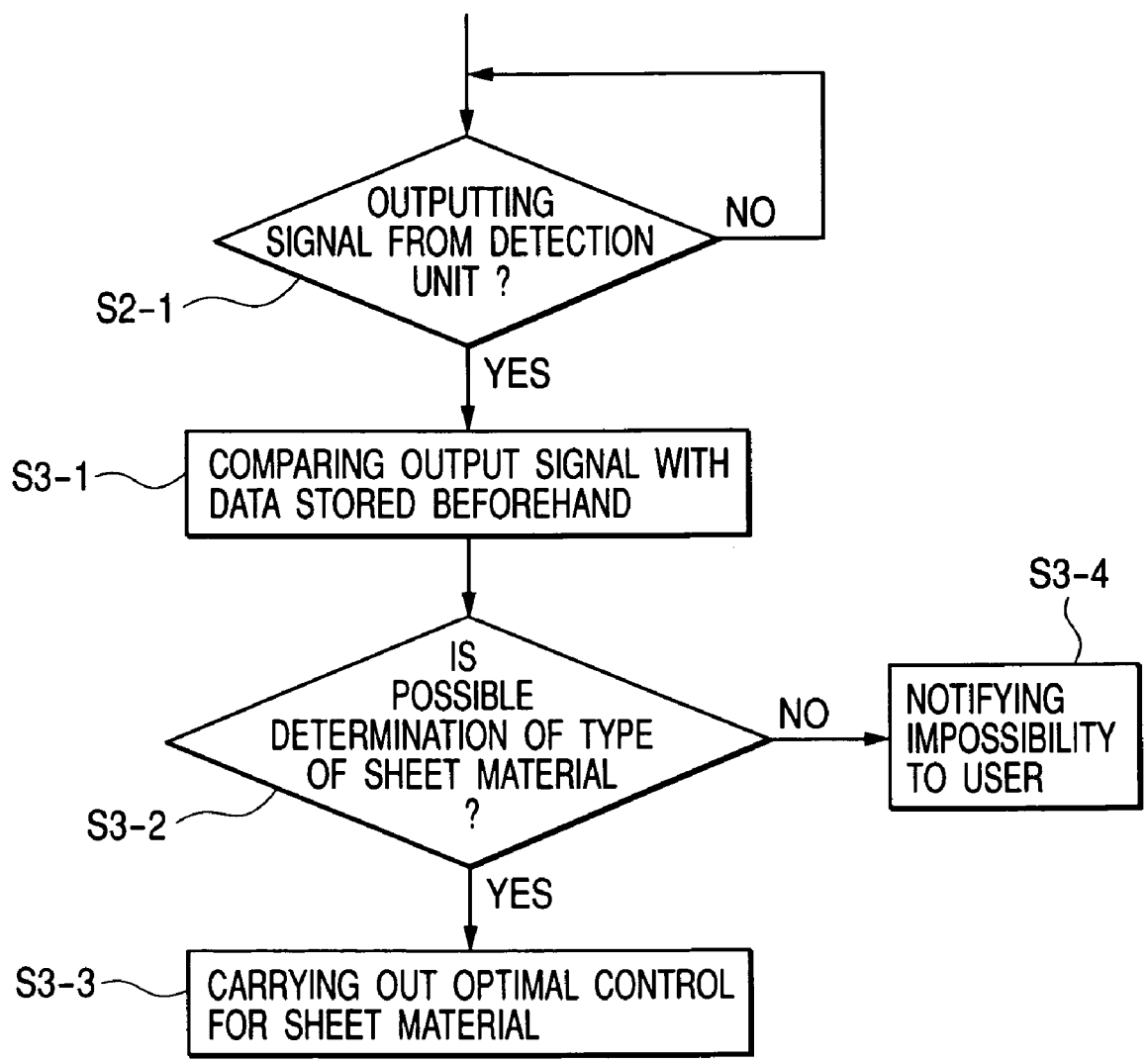
FIG. 3 is a flow chart for determining the type of sheet material according to the present invention.

Furthermore, the determination of the type in the present invention is a concept including not only determination of the type of sheet material but also determination of what the sheet material is close to if the type of the sheet material is not known. For example, it includes determination of whether the sheet material is a paper or plastic sheet (OHP sheet: transparency for overhead projector), and determination of whether it is a thick paper or thin paper even for the same type of sheet. Difference in thickness means difference in weight of sheet material. In the present invention, determination for at least two types is acceptable, but as a matter of course, determination for more than two types, for example determination of whether the sheet material is a plain paper, a coated paper or a photo paper is preferred. Furthermore, the coated paper is a paper with a coating layer provided on the surface. The photo paper is a paper with bright finish applied to the surface. The photo paper is generally more expensive than the coated paper. Also, the setting of conditions for any item to be controlled based on the output signal from the detection unit so that they are suitable for the sheet material is equal to determination of the type of sheet material as a matter of course. The item to be controlled will be described later. FIG. 3 shows an example in which the method for determining the type is used when an image is formed. The detection unit outputs a signal by the impact (S2-1), the output signal is compared with information stored in advance (S3-1), and if determination of the type of sheet material is possible, the item to be controlled is controlled so that it is optimally set for the sheet material (S3-3), and if the determination is impossible, notification of this result is given to the user (S3-4) If the determination is impossible, an image can be formed based on the predefined setting without giving the notification to the user, as a matter of course.

The information about a sheet material is preferably information incorporating temperature and humidity conditions.

Furthermore, in determination of the type of sheet material, the determination of the type of sheet material by application of an impact, and determination by an optical method may be used in combination. The optical method is a method in which the surface of the sheet material is exposed to light, and taking advantage of the fact that its transmitted light, scattered light and reflected light depends on the type of sheet material, the type of sheet material is determined. The method is described in Japanese Patent Application Laid-Open No. 2000-301805 (U.S. Pat. No. 6,291,829), for example.

Apparatus for Determining the Type

The apparatus for determining the type of sheet material of the present invention comprises an impact applying unit applying an impact to a sheet material from the outside, and a detection unit outputting a signal by the impact, and determines the type of sheet material based on the signal from the detection unit. The type of sheet material is determined using a data table stored in advance and the signal from the detection unit. The determination of the type of sheet material may be made by an electric circuit, or using a program.

This determination apparatus may be mounted on image forming apparatuses (printer, copier, facsimile, etc.), image readers (scanner, page reader), sheet conveying apparatuses (sheet feeder), sheet material number counting apparatuses, sheet material type classifying apparatuses, sheet conveying apparatuses and sheet payload apparatuses.

The determination of the type of sheet material may be made by man using a detection signal, but may also be made in the above image forming apparatus or the like, or by an external apparatus (e.g. computer) connected to such an apparatus.

If the apparatus for determining the type according to the present invention is mounted on the image forming apparatus, the detection unit of this apparatus for determining the type has a configuration of, for example, a detection unit 1420 shown in FIG. 4. The signal from this detection unit is transmitted to an external computer (including wireless transmission and wire transmission), the type of sheet material is determined in the computer, and the conditions for the item to be controlled are set based on the result of the determination so that they are the most suitable for the sheet material.

Signal Processing for Determination

For the signal for use in determination of the type of sheet, a signal (second signal) outputted before the impact is applied and a signal (third signal) outputted at the time when the impact is applied to the signal output apparatus in the situation in which the sheet material does not exist may be used in addition to the first signal outputted from the detection at the time when the impact is applied.

For example, signal processing is carried out such that the output signal (third signal) when the sheet material 1410 is not pinched in FIG. 4 is subtracted from the first signal. For such signal processing, a signal processing circuit for carrying out the processing may be used.

Determination Method

Figure 7:
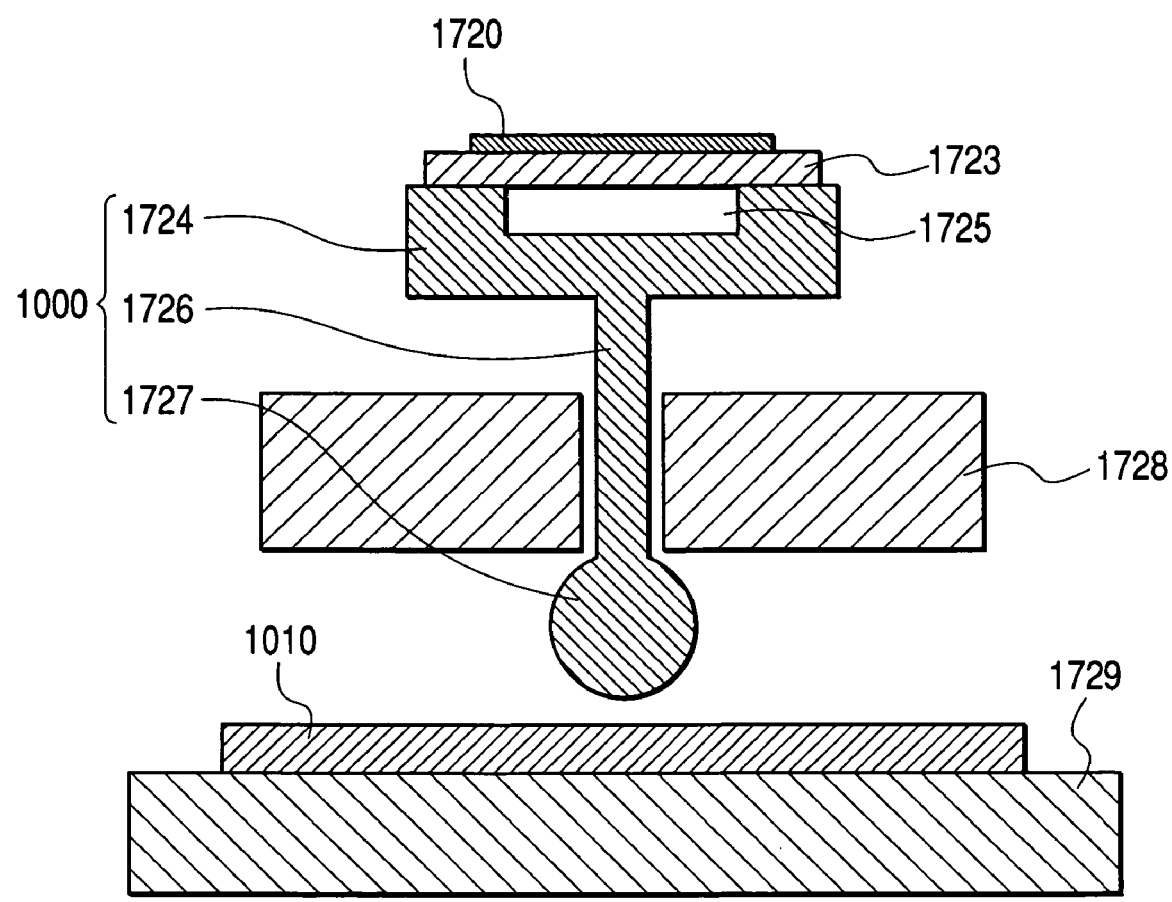
FIG. 7 illustrates the signal output apparatus according to the present invention.

An example of the configuration of the apparatus using the piezoelectric element as the detection unit is shown in FIG. 7. In this figure, Reference numeral 1720 denotes the piezoelectric element functioning as the detection unit, reference numeral 1723 denotes an elastic deformable member (e.g. flat spring) having the piezoelectric element 1720 thereon and being pinched so that it can be deformed by collision, reference numeral 1724 denotes a movable base portion for fixing the elastic deformable member on a pedestal, reference numeral 1725 denotes a groove portion formed on the movable base portion for enabling the elastic deformable member to be deformed, reference numeral 1726 denotes a movable axis portion connected to the movable base portion, and reference numeral 1727 denotes an impact portion having a hemispherical surface, which is connected to the front edge of the movable axis portion. The piezoelectric element is located so that deformation of the elastic deformable member can be detected.

The impact applying unit 1000 is comprised of the movable base portion 1724, the movable axis portion 1726 and the impact portion 1727. The impact applying unit 1000 may be a united body, or may have a configuration such that each portion can be separated. The detection unit 1020 is comprised of the piezoelectric element 1720 and the elastic deformable member 1723. In this way, the aspect of this figure is an example of the detection unit mounted on the impact applying unit. Reference numeral 1728 denotes a bearing portion for promoting the uniaxial movement of the movable axis portion 1726, reference numeral 1010 denotes the sheet material, and reference numeral 1729 denotes a substrate for supporting the sheet material 1010.

Figure 8:
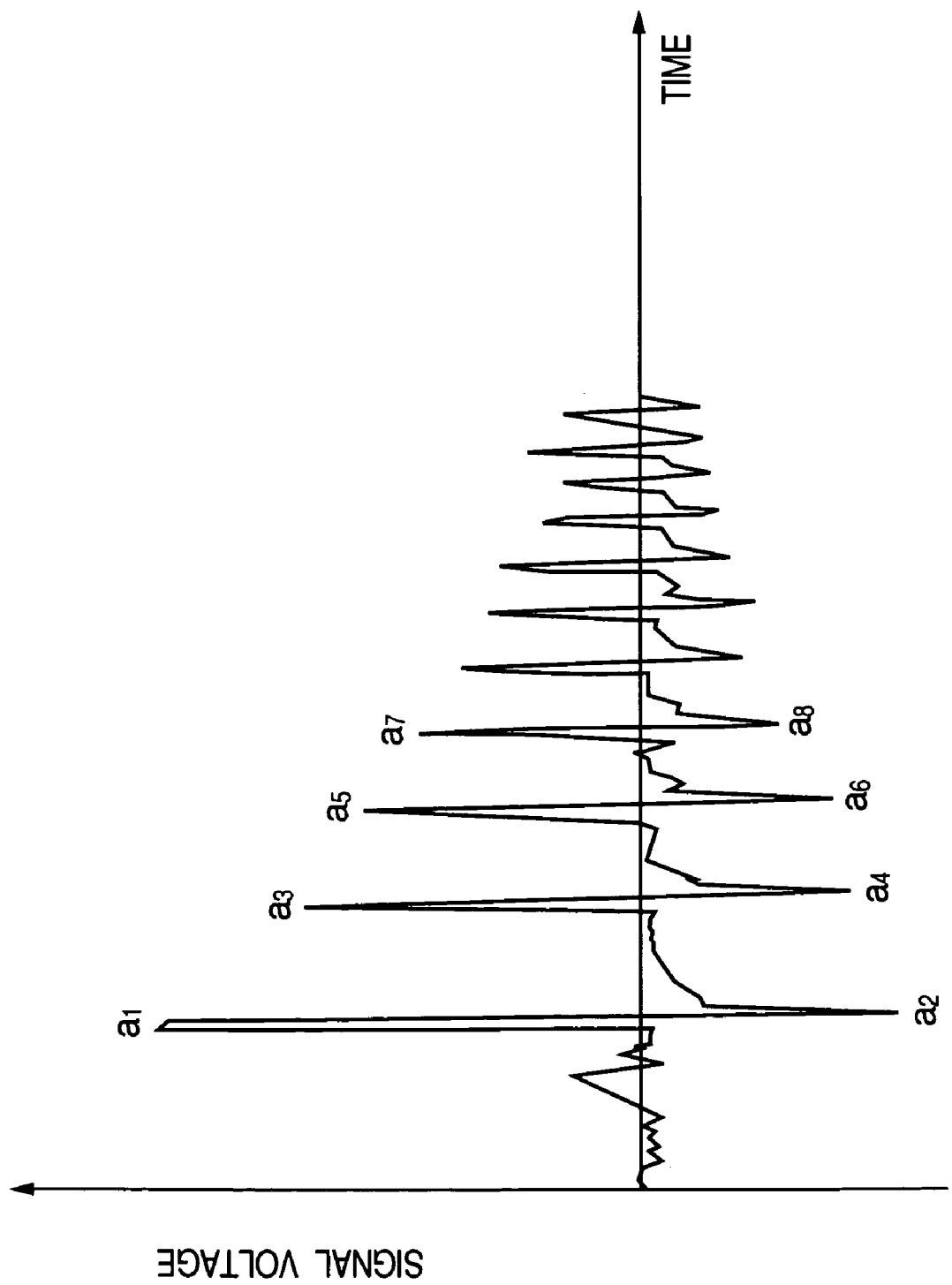
FIG. 8 shows an example of an output signal according to the present invention.

When the impact is applied to the sheet material 1010 by the impact applying unit 1000, the signal shown in FIG. 8 is outputted from the piezoelectric element. In this figure, the horizontal axis represents time, and the vertical axis represents voltage (electric potential difference). Reference character a1 denotes a signal occurring by first collision against the impact applying unit, reference character a3 denotes a signal occurring by second collision, reference character a5 denotes a signal occurring by third collision, and reference character a7 denotes a signal occurring by fifth collision.

For determining the type of sheet material, information such as the peak value of the signal, the peak interval, a change in time of the peak interval, time until the signal is attenuated to a predetermined value or smaller, the number of peaks until the signal reaches a predetermined value or smaller, time until a predetermined peak occurs, the number of peaks in a predetermined time interval, the signal wave form, frequency properties and integrated intensity may be used. Using a plurality of piezoelectric elements, information such as the intensity difference and intensity ratio between signals from respective elements, or the phase difference and peak time difference may be used.

Figure 10:
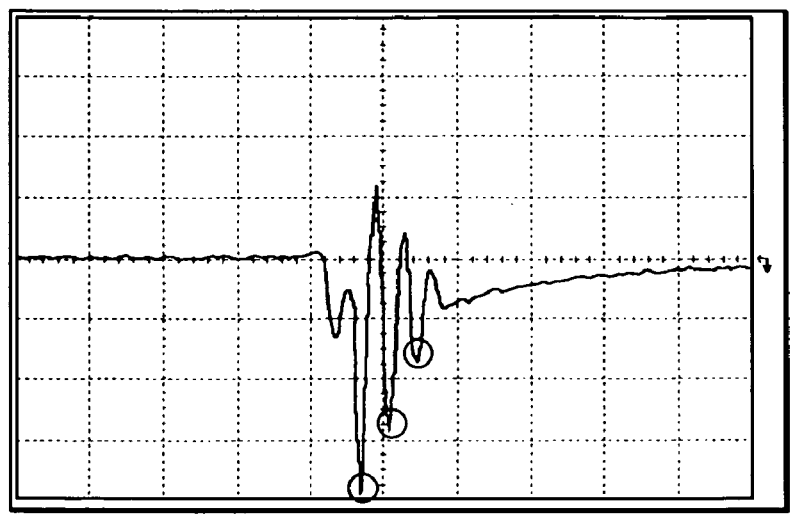
FIG. 10 shows an example of the output signal according to the present invention.
Figure 11:
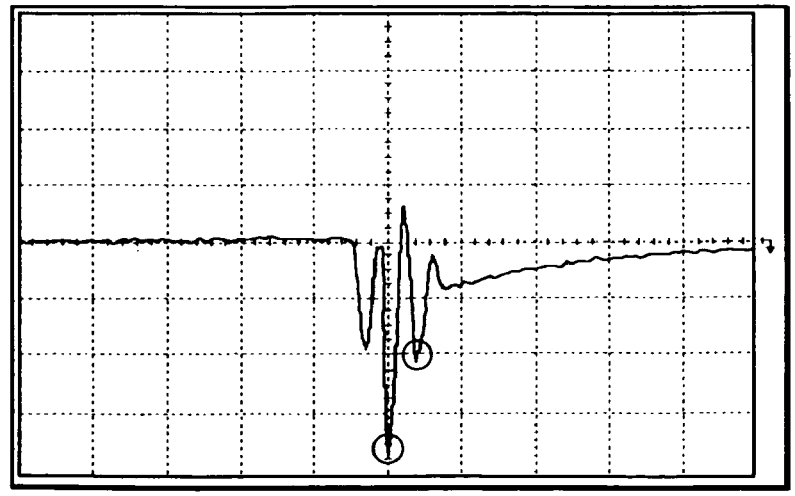
FIG. 11 shows an example of the output signal according to the present invention.

When the inventor applied a same impact to each of a plain paper (CP-250: New Printer Paper), a coated paper (HR101S: High Resolution Paper), Photo Paper (GP301: Photo Glossy Paper) (all manufactured by Canon Inc.), the numbers of peaks until the voltage signal was attenuated were different for each type of sheet: 5 for the plain paper (FIG. 9), 3 for the coated paper (FIG. 10), and 2 for the photo paper (FIG. 11), so that the type of sheet material could detected. Furthermore, the peak mentioned herein corresponds to the spot marked with a circle in the figure.

Method of Making a Determination Using Recoil Period of Impact Applying Unit

The impact applying unit travels in the first direction toward the sheet material, collides against the sheet material, and then recoils in the direction (second direction) opposite to the first direction. This phenomenon is the recoil.

The recoil period is a time period over which the impact applying unit stays in space after colliding against the sheet material and before colliding against the sheet material again. Alternatively, it may be the total of a plurality of periods between collision and next collision, or it may be a period between the time when the impact applying unit initially collides against the sheet material and the time when it is substantially in the static state. The time points at which the recoil period starts and ends may be determined using the maximum value of the signal from the piezoelectric element at the time of collision. The recoil period including a plurality of collisions may be determined by calculating the time interval between the nth collision (n is an integer number equal to or larger than 1) and the mth collision (m is an integer number equal to or larger than 2, and m>n holds). Also, a predetermined pulse may be generated over a time period between the nth collision and the (n+1)th collision to calculate the recoil period from the number of clock pulses generated in the AND circuit of the pulse and an external clock pulse of known frequency.

Figure 14:
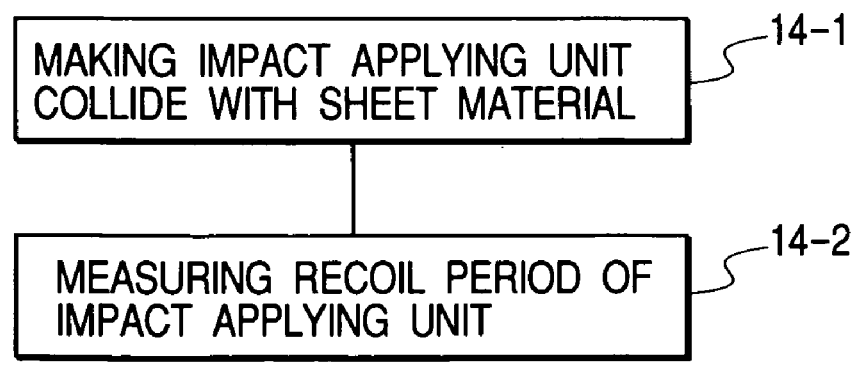
FIG. 14 illustrates the present invention.

The method for determining the type of sheet material using the recoil period will be described with reference to FIG. 14. First, the impact applying unit comprising the piezoelectric element is made to collide with the sheet material (14-1). A signal is outputted from the piezoelectric element by the collision, and the signal is used to measure the recoil period of the impact applying unit (14-2). The measured value is compared with the data table stored in advance, whereby the type of sheet material can be determined.

Also, the recoil period can be determined by calculating the time interval between the nth collision (n is an integer number equal to or larger than 1) and the mth collision (m is an integer number equal to or larger than 2, and m>n holds). For example, the duration between the first collision and the fifth collision is calculated, and the type of sheet material can be determined using the calculated duration.

The threshold may be set corresponding to the time after collision of the impact applying unit against the sheet material.

The threshold also may be set in correspondence with the signal intensity having been detected in preliminary collision of the impact applying unit against the sheet material before identification of the sheet material.

The threshold also may be set in accordance with the maximum and the minimum of the signal generated by one collision of the impact applying unit.

The apparatus may comprise further an interval-computing means for computing the interval between the pulses generated by the pulse generating means, and an identifying means for identifying the type of the sheet material based on computation by the interval-computing means.

The threshold-setting means may set the threshold for the second or later collision of the impact applying unit.

The threshold-setting means may compute a threshold from the maximum and the minimum of the signal outputted from the detection unit on the collision and feed the computed threshold to the pulse-generating means as the threshold for the subsequent collision.

An initial threshold-setting means may be provided for setting the threshold for the first collision of the impact applying unit, the initial threshold-setting means computing the initial threshold from the output from the detection unit in collision of the impact applying unit against the sheet material preliminarily before identification of the sheet material.

In the image-forming apparatus of the present invention, the threshold-setting means may compute the threshold on start or reset of the image-forming apparatus. Further, the threshold-setting means may compute the threshold when a change of the sheet material is expected.

The apparatus for determining the type of sheet of the present invention is described below by reference to FIGS. 55 to 58A through 58C.

The apparatus for determining the type of sheet of the present invention is used for identifying the type of a sheet material, and comprises impact applying unit 1 to be rebounded from sheet material P, and sensor 2 for detecting the position of the impact applying unit. This sensor 2 outputs signals as to the position of impact applying unit 1 (201 in FIG. 57A, and 202 in FIG. 58A). The signal output reaches a maximum on collision of impact applying unit 1 against sheet P. The pulse-generating means (3 in FIG. 56A) generates a pulse when output signal 202,201 reaches or exceeds a prescribed threshold on collision of impact applying unit 1 against sheet material P (FIG. 57B, and FIG. 58B). An interval computing means (5 in FIG. 56A) derives an interval (rebounding period) between a pulse and another pulse generated by pulse-generating means 3. An identifying means (6 in FIG. 56A) identifies the type of the sheet material according to the result of the detection by interval-computing means 5.

The aforementioned threshold value (threshold for the second and later collisions of the impact applying unit) is set at a suitable level by a threshold-setting means (4 in FIG. 56A). The setting is conducted by any of the methods of (1) lowering the threshold level with lapse of the time (see Example 14),
(2) lowering the threshold level with times of collisions of impact applying unit 1,
(3) lowering the threshold level on occurrence of change of the maximum or minimum level, and
(4) computing the threshold from the maximum and minimum (e.g., average thereof) of the signal outputted from the sensor 2 on the aforementioned collision and utilizing the computed threshold as the threshold for the subsequent collision (see Example 15).

The threshold for the first collision (initial threshold) of the aforementioned impact applying unit 1 may be (1) the one set before the sheet material identification, or
(2) the one computed by an initial threshold-setting means (901,902,903 in FIG. 62A) from the output of sensor 2 in preliminary rebounding of impact applying unit 1 from the sheet material before the sheet material identification measurement (preliminary rebounding test conducted before the sheet material identification, not the rebounding for identification of the sheet material) (see Example 3).

The apparatus for determining the type of sheet having the aforementioned constitution is preferably incorporated in an image-forming apparatus and the image is formed in the image formation section preferably under the conditions selected as the result of the detection by the apparatus for determining the type of sheet. In the image-forming apparatus, at the start or reset of the image-forming apparatus, the initial threshold may be computed by the aforementioned initial threshold-setting means (Example 4), or at the time when the change of the sheet material is expected (e.g., exchange of a paper feed tray; Example 5).

An elastic member may be placed to be deformable on impact force application by impact applying unit member 1 (symbol A in FIG. 55), and a piezoelectric element may be mounted preferably on elastic member A as a sensor. Thereby collision of impact applying unit 1 against sheet material P distorts elastic member A to allow piezoelectric element 2 to output a signal.

The rebounding period (interval between pulses) computed by the aforementioned interval computing means 5 may be (1) a period of floating of impact applying unit 1 unsupportedly in the air after collision against sheet material P,
(2) a period between collision of impact applying unit 1 against sheet material P and the subsequent collision, or
(3) a period between collision of impact applying unit 1 against sheet material P and another collision (time interval between an n-th collision and an m-th collision (m being an integer of 2 or greater, and m>n). For the measurement of the period, the time is measured suitably by employing clock pulses and a time-counting circuit for counting the clock pulses.

The effects of this embodiment are described below.

In this embodiment, the sheet material quality (e.g., distinction between plain paper and coated paper) can be identified accurately by detecting precisely the collision of the impact applying unit against the sheet material.

Figure 66A:
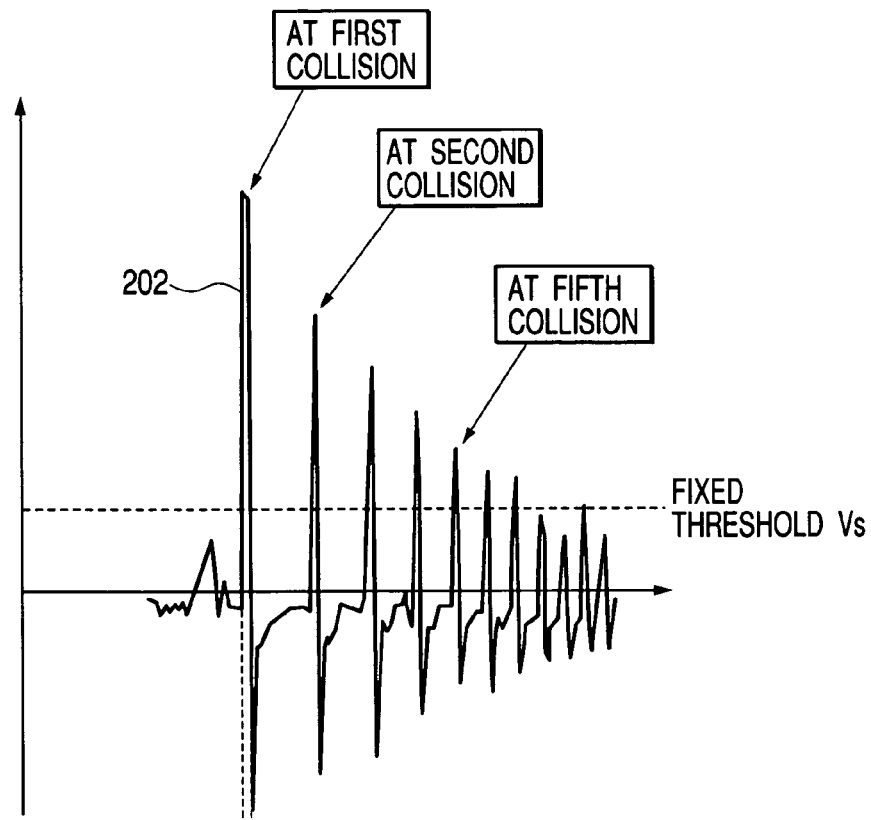
FIGS. 66A, 66B and 66C illustrate disadvantage of conventional detection apparatus.
Figure 66B:
Figure 66C:
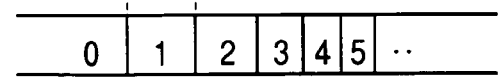

The type of a sheet material can be identified by the behavior of an impact applying unit in rebounding from a sheet material. In this material identification, the position of the impact applying unit is detected with a piezoelectric element, and is represented by an output signal as shown by reference numeral 202 in FIG. 66A. The output signal 202 is compared with threshold value Vs by a comparator (not shown in the drawing). The peak portions of the output signal waveform are made binary (see FIG. 66B), and the pulse intervals are measured by a time counter circuit (see FIG. 66C), from which the sheet material can be identified.

Figure 67A:
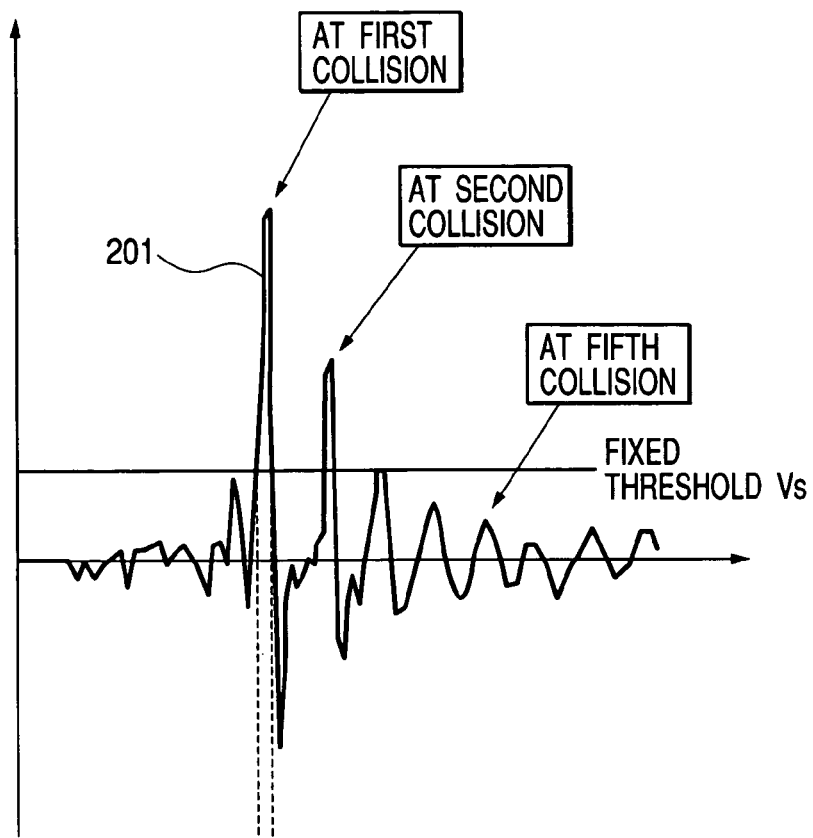
FIGS. 67A, 67B and 67C illustrate disadvantage of conventional detection apparatus.
Figure 67B:
Figure 67C:
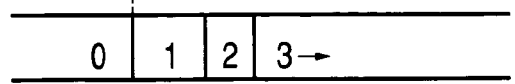

The output from the piezoelectric element, however, cannot always be made binary with a fixed threshold value. For example, the binary signal cannot be produced in the case where the output signal of the piezoelectric element attenuates greatly to be lower than the threshold level as shown by reference numeral 201 in FIG. 67A. If the threshold level is set too low preliminarily, a noise can also be detected. Therefore, in this embodiment, the threshold level is set between the successive rebounds of the impact applying unit to solve the above problem.

For the damped rebounding of the impact applying unit, the threshold for the m-th collision (second threshold) is made lower than the threshold for n-th collision (m>n) (first threshold).

Incidentally, the sensor for outputting a signal on the impact application is referred to occasionally as a "position sensor" for impact applying unit in the description in this specification.

The impact applying unit that can suitably be used in this embodiment will be described with reference to FIG. 7 in which the impact applying unit is free-fallen to apply an impact to the sheet material. In this embodiment, for the impact itself, springs (including those using expansion and contraction of solids and those using dumping of gas) and electromagnetic force may also be used, as a matter off course.

Figure 15A:
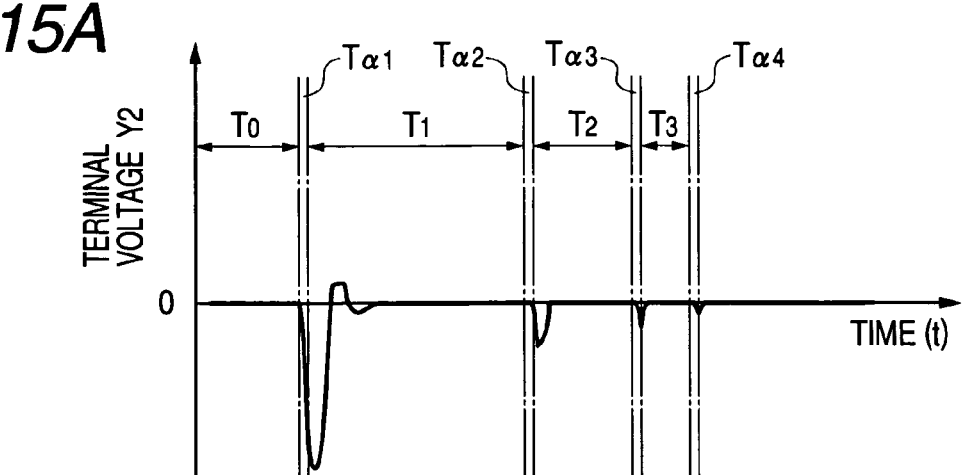
FIGS. 15A, 15B and 15C show examples of the output signal according to the present invention.
Figure 15B:
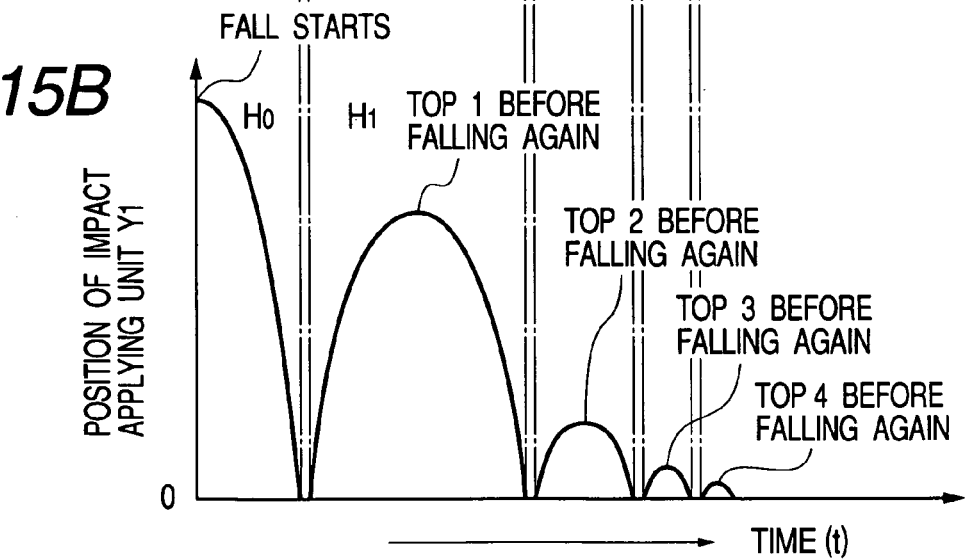

Each time when the impact applying unit is collided against the sheet material 1010, a piezoelectric signal as shown in FIG. 15A is obtained. The horizontal axis in FIGS. 15A and 15B represents time. The vertical axis in FIG. 15A represents the terminal voltage. FIG. 15B shows the positions of the impact applying unit corresponding to the time shown in FIG. 15A. Examples of the elastic deformable member 1723 include a flat spring, a cantilever spring, a center spring, a periphery fixation spring and a coil spring.

Also, the substrate 1729 being a platen or the like is not absolutely necessary, but any member causing a recoil may be used.

When the movable base portion 1724 as shown in FIG. 7 is fallen from an altitude of H0, then the impact portion 1727 is collided against the sheet material 1010 on the substrate 1729 after a period of time T0, and the impact applying unit 1000 recoils through a period T.alpha.1 over which the sheet material is deformed. Here, the deformation includes plastic deformation and/or elastic deformation.

Thereafter, the impact applying unit rises along the bearing portion 1728 into the space to an altitude H1, then starts to fall, and collides against the sheet material 1010 again.

The impact unit 1727 again recoils through a period T.alpha.2 over which the sheet material is deformed, and finally stops after repeating the above operations.

As the movable base portion 1724 undergoes gradual reduction in the recoil height, the elastic deformable member 1723 has its momentum changed by the impulse occurring at the time when the movable base portion 1724 (including the piezoelectric body 1720, elastic deformable member 1723, movable axis portion 1726 and impact portion 1727) is collided against the sheet member 1010.

Specifically, the elastic deformable member 1723 is transited from the static state into the dynamic state to start vibrating, and the vibration has its amplitude reduced due to rapid attenuation by viscous resistance of a flat spring vibration system, thus finally bringing about a stopped state on a temporary basis. A piezoelectric signal is outputted from the piezoelectric element in response to such deformation of the flat spring. Thereafter, as the collision and the fall described above repeatedly occur, the rapid attenuation of vibration is repeated due to the rapid deformation and the viscous resistance of the flat spring vibration system, respectively.

In the process of the above repetition, the time interval at which the impact applying unit 1727 collides against the sheet material 1010 (the recoil period) and the piezoelectric signal (voltage or piezoelectric current) are detected, thereby detecting the type of sheet material.

The piezoelectric current occurs in proportion to the deformation speed of the piezoelectric body, and therefore the piezoelectric body 1720 taking on a rapid deformation speed due to the rapid deformation of the flat spring at the time of each collision causes a maximum piezoelectric current at the time of the collision (a voltage V is generated at each electrode of the piezoelectric body in proportion to the piezoelectric current) as shown in FIG. 15B.

By the internal impedance of the piezoelectric body, the piezoelectric current can be picked up as a voltage signal from the each electrode of the piezoelectric body.

Figure 15C:
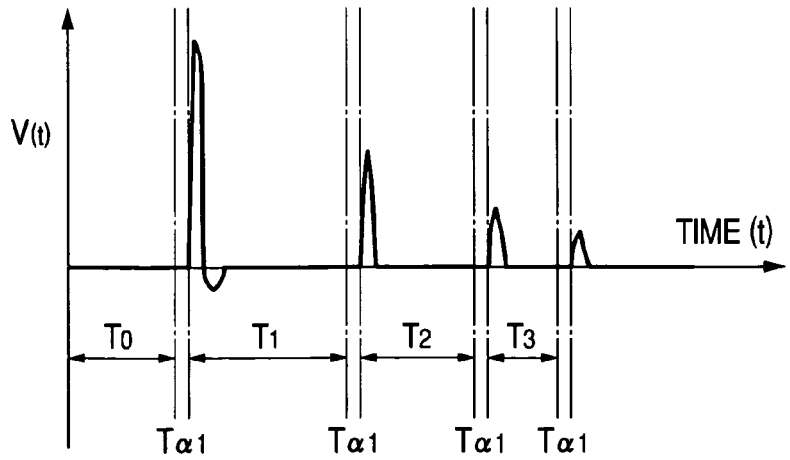

Thus, in the period of time after the impact member is fallen as shown in FIGS. 15A to 15C, the time interval between maximum signals of the voltage generated in the piezoelectric body at the time of each collision is measured, whereby the type of sheet material (e.g. the type of sheet) can be detected. This takes advantage of the fact that the deformability and rigidity of sheet material varies depending on the type of sheet material.

In the case of the measurement of time described above, comparisons may be made by measurement of time T1, or measurement of time T1+T2, or measurement of time T1+T2+T3 (see FIGS. 15A to 15C). Alternatively, the type of sheet may be determined after data is processed using the time measured as described above (e.g. data of recoil period for each type of sheet material is memorized in advance, and comparisons are made to determine whether the measured data is consistent with the measured value, or which type of sheet material the value is relevant to. At that time, a data table incorporating parameters related to humidity and temperature may be memorized, so that in making a determination, the temperature and humidity are measured to determine the type of sheet material). During application of the impact, the sheet material may be substantially in the static state (it is not being conveyed in a printer, but is at rest, and it may be in a state either before or after being conveyed), or the impact applying member may be collided against the sheet material while it is conveyed (i.e. moved).

Furthermore, a data table with recoil periods corresponding to types of sheet materials stored therein in advance is provided in a printer or a computer connected to the printer, and information detected by the recoil period detecting unit is compared with the data table, whereby the type of sheet material can be determined. After the type of sheet material is determined, the setting of print modes can be performed in the printer, or from the computer connected to the printer. The setting of print modes includes, for example, control of discharge of ink. The setting may be inputted by man, or may be done automatically.

FIG. 16 shows a schematic view of the configuration in the printer 2600.

The signal from the impact applying unit is inputted to a recoil period detecting circuit unit (recoil period detecting unit) to detect the period, and thereafter the type of sheet material is determined through the type determining unit with the above described data table stored therein. Thereafter, printing is carried out in optimal recording mode in a recording mode controlling unit. Furthermore, the type of sheet material may be determined in an external computer (connected to the printer) using the signal from the recoil period detecting unit, not in the printer. In this case, the recording mode controlling signal is sent from the external computer to the printer. Also, the type of sheet may be determined for each piece, or for a predetermined number of pieces specified by the user. A configuration such that the type of sheet material is detected only when the main power source of the printer is turned on is also possible.

Figure 17:
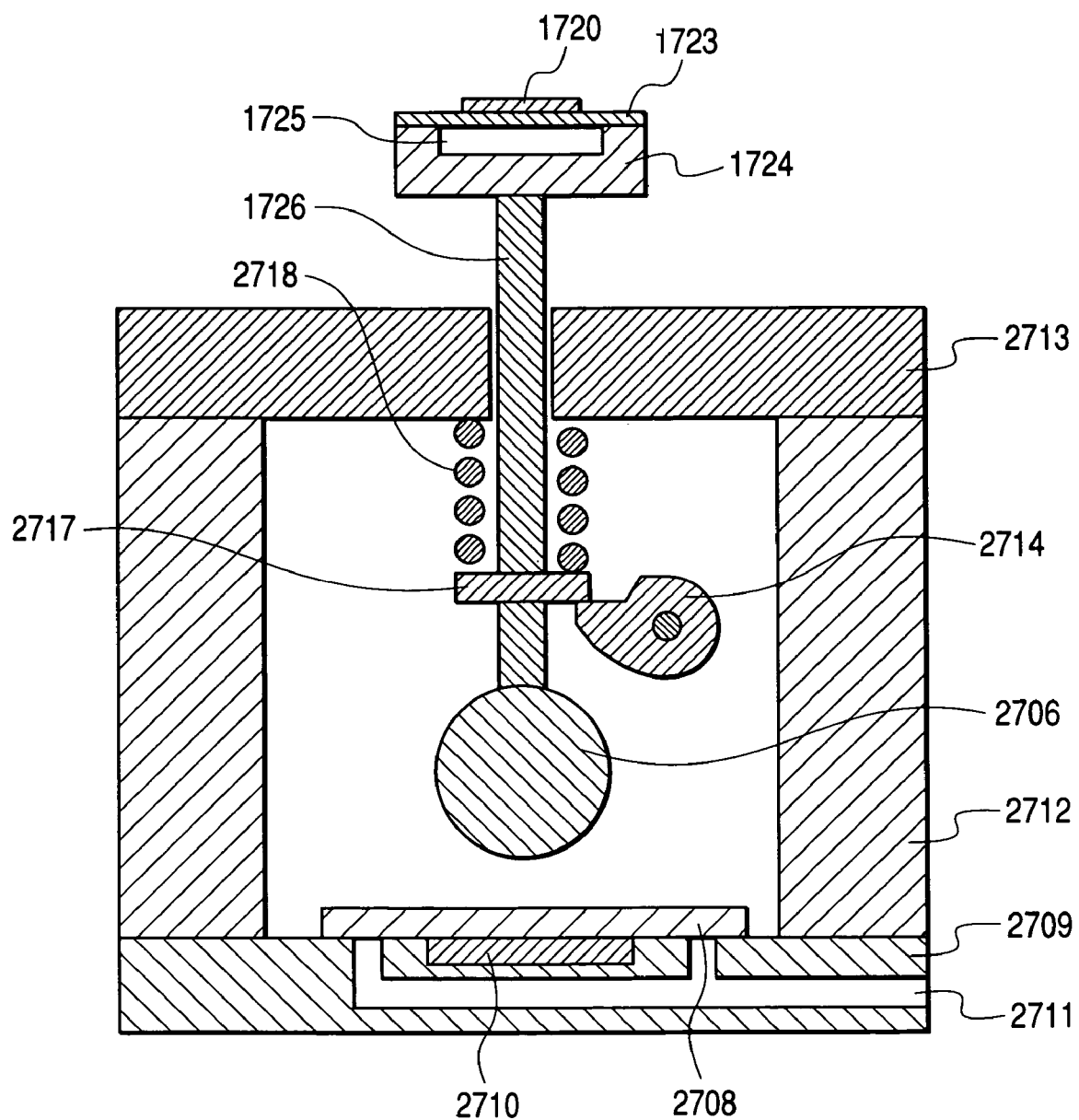
FIG. 17 illustrates the signal output apparatus according to the present invention.

Furthermore, for how the impact applying member is fallen, not only gravity but also a spring 2718 may be used as shown in FIG. 17. In the case where the spring and the like are used, a higher degree of freedom as to the angle of the impact applied to the sheet material can be provided.

Another method for measuring the recoil period will be described.

When the impact applying member is collided, a predetermined pulse is generated over a time period between the nth (n is an integer equal to or greater than 1) collision and the (n+1)th collision to calculate the recoil period from the number of clock pulses (AND pulses) generated in the AND circuit of the pulse and an external clock pulse of known frequency. The predetermined pulse can be generated using as a trigger the signal from the piezoelectric element at the time of collision of the impulse applying member. This will be described specifically below.

Specifically, as shown in FIGS. 18A to 18D, the voltage (denoted by reference numeral 2801 in FIG. 18A) generated in the piezoelectric body at the time of the collision is used as a trigger to generate a first pulse (denoted by reference numeral 2802 in FIG. 18B), and an AND pulse (denoted by reference numeral 2804 in FIG. 18D) is generated in the AND circuit of an external pulse of known frequency (denoted by reference numeral 2803 in FIG. 18C, and referred to as a second pulse) and the first pulse, and the AND pulse 2804 is counted to calculate the time period (recoil time), thereby detecting the type of sheet.

For the relation between the first pulse and the second pulse, the duration (period) of the second pulse is shorter then the duration of the first pulse.

Figure 18A:
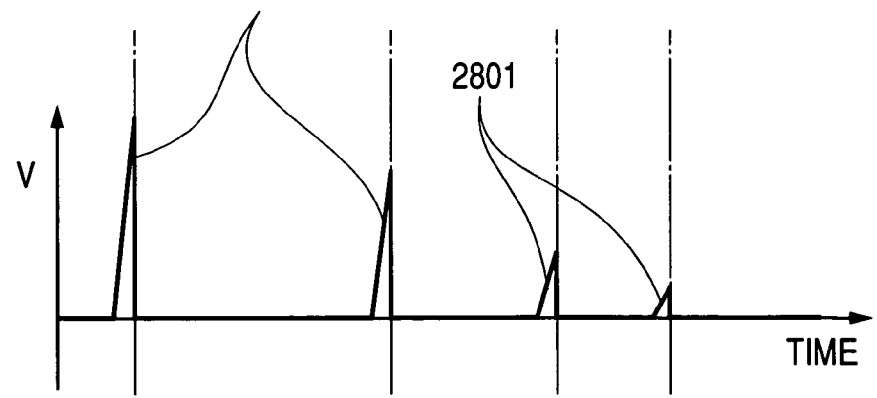
FIGS. 18A, 18B, 18C and 18D show examples of the output signal according to the present invention.
Figure 18B:
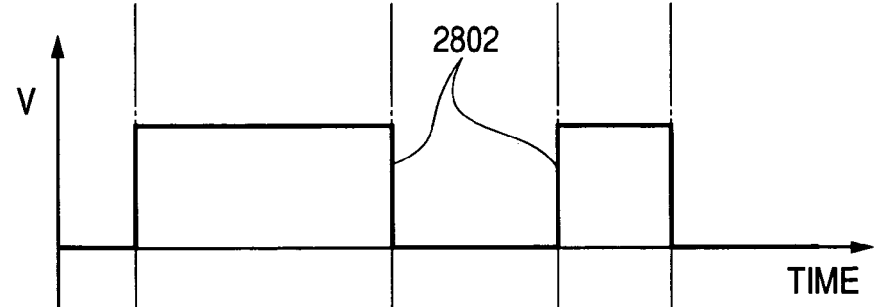
Figure 18C:
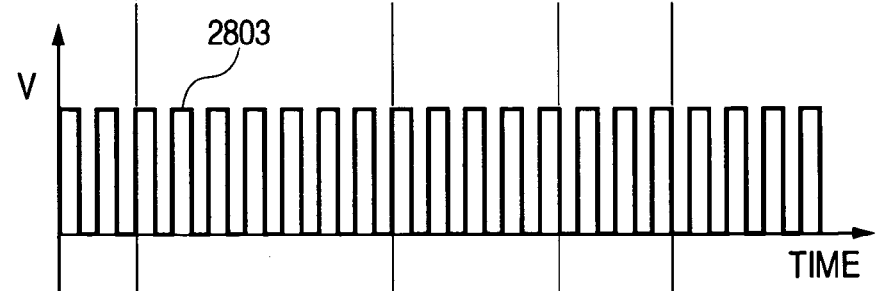
Figure 18D:
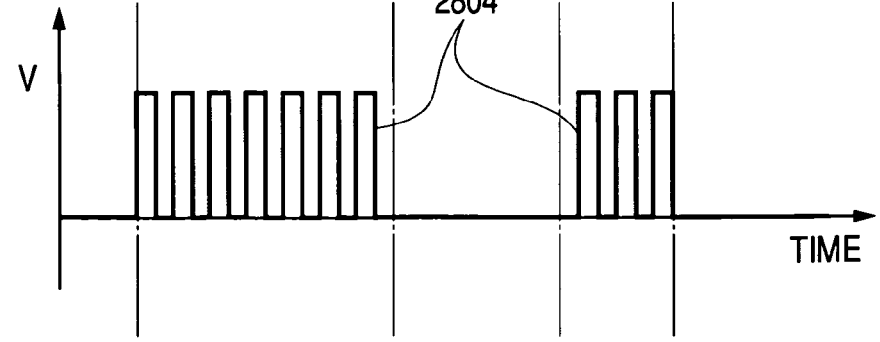

Also, the time interval between the pulse 2802 and the pulse 2803 in FIGS. 18B and 18C may be determined using the NAND circuit. In such a case, time intervals other than calculated time intervals described above will be calculated. Furthermore, combination of the both time periods is equivalent to calculation of the time period between the instant when collision occurs and the instant when the recoil is ended.

Furthermore, the piezoelectric current is converted into a voltage and used in this case, but a change in piezoelectric current may be used to detect the instant when collision occurs.

In addition, in the vibration system of the elastic deformable member (impact applying unit described with FIG. 7), the periphery of the deformable member (e.g. the flat spring described above) can be retained in the atmosphere of pressure gas to increase as much as possible the viscous resistance component serving for attenuation of vibration. Furthermore, the piezoelectric body can also be retained in the atmosphere of pressure gas. For the atmosphere in such a case, the pressure is preferably higher than the ambient pressure (e.g. equal to or larger than 1 atom and equal to or smaller than 2 atom), and type of gas includes nitrogen gas, argon gas and inert gas.

The resistance component may be generated by gas flow.

In addition, a light-weight flat spring can also be used for increasing the vibration amplitude of the flat spring by an impulse generated at the time of collision.

Furthermore, for how the impact applying member is fallen, not only gravity but also a spring 2718 may be used as shown in FIG. 17.

The apparatus having the deformable member retained in the atmosphere of pressure gas has been described, but conversely, the deformable member can be retained in the atmosphere of reduced pressure so that the viscous resistance component is reduced. In such a case, the deformable member will create natural vibration (or vibration that can be considered substantially as natural vibration.

Therefore, the recoil period can be calculated by counting pulses generated by the natural vibration.

Figure 19:
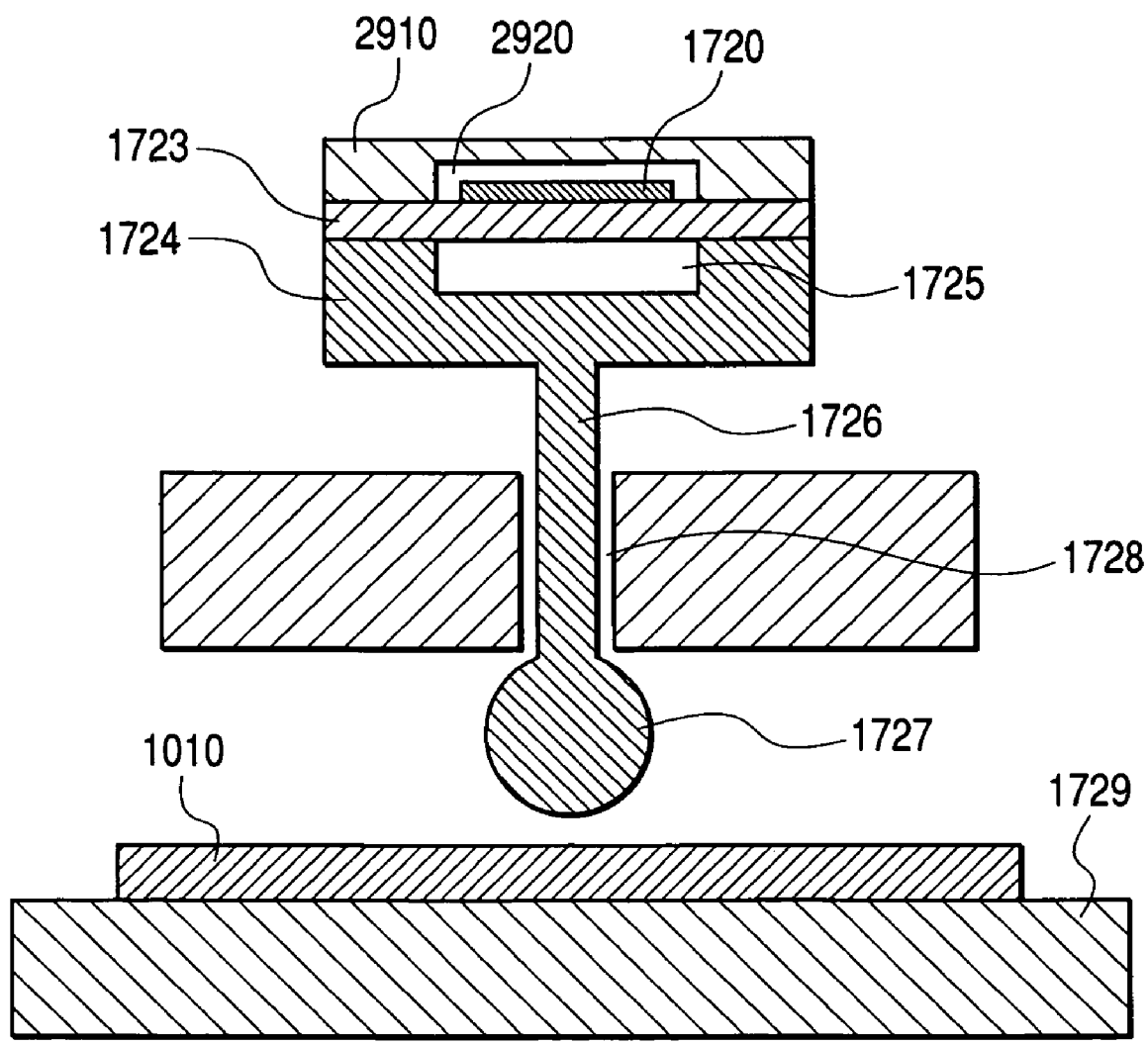
FIG. 19 illustrates the signal output apparatus according to the present invention.

For the atmosphere of reduced pressure, the level of pressure may be in the range of from $10^{-5}$ Torr to $10^{3}$ Torr, preferably from $10^{3}$ Torr to $10^{2}$ Torr, and vacuum pressure is also acceptable as a matter of course. An example of the impact applying member allowing the natural vibration to be created will be described with reference to FIG. 19. Components having functions same as those of the elements of the apparatus in FIG. 2 are given same numbers.

In this figure, reference numeral 1720 denotes the piezoelectric body serving as a sensor, reference numeral 1723 denotes the flat spring that has the piezoelectric body 1720 mounted thereon, reference numeral 1726 denotes the movable base portion for fixing the elastic deformable member (e.g. flat spring) 1723 on a pedestal, reference numeral 1725 denotes a groove portion formed on the movable base portion 1724 for enabling the flat spring 1723 to be deformed, reference numeral 1726 denotes a movable axis portion connected to the movable base portion 1724, and reference numeral 1727 denotes an impact portion having a hemispherical surface, which is connected to the front edge of the movable axis portion 1726 (of course, the surface is not limited to a curved surface as long as predetermined recoil is achieved).

In this figure, reference numeral 2910 denotes a sealing member for retaining in the atmosphere of reduced pressure the flat spring 1723 serving as a deformable member. An area 2920 surrounded by the sealing member and the flat spring 1723, and the groove portion 1725 are both under reduced pressure. Furthermore, it is preferable that the pressure in the area 2920 is identical to the pressure in the area 1725 in terms of natural vibration. Also, there may be a difference in pressure between both areas. Furthermore, in the drawing, electrodes and wirings provided on the both sides of the piezoelectric body 1720 are not shown.

The elastic deformable member (e.g. flat spring) 1723, the piezoelectric body 1720, the movable base portion 1724 and the movable axis portion 1726 and the impact portion 1727 constitute a united recoil body, and reference numeral 1728 denotes a bearing portion for promoting the uniaxial movement of the movable axis portion 1726, reference numeral 1010 denotes the sheet material (e.g. printing paper), and reference numeral 1729 denotes a platen that has the sheet material 1010 mounted thereon, and is collided against the impact portion 1727 with the sheet material 1010 therebetween.

Figure 20A:
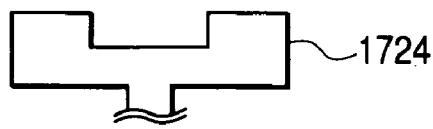
FIGS. 20A, 20B, 20C, 20D, 20E, 20F and 20G illustrate a method of manufacturing the signal output apparatus according to the present invention.
Figure 20B:
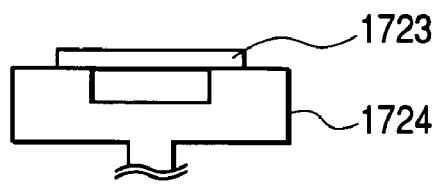
Figure 20C:
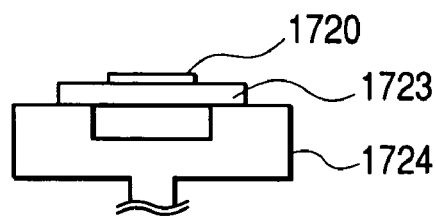
Figure 20D:
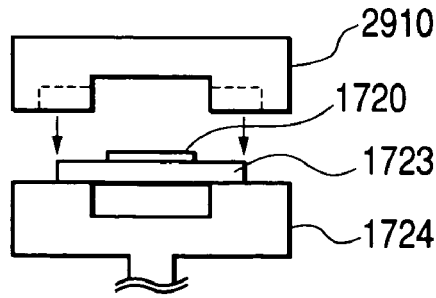
Figure 20E:
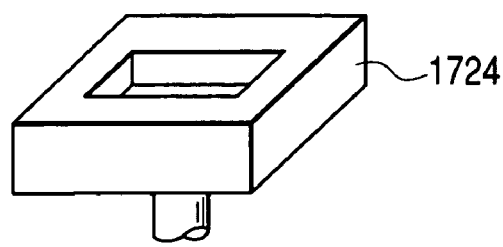
Figure 20F:
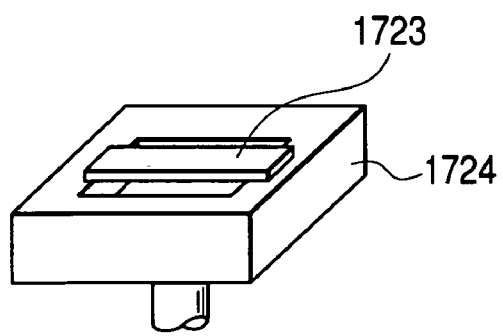
Figure 20G:
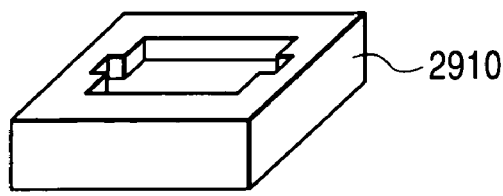

Furthermore, for retaining the flat spring 1723 in the atmosphere of reduced pressure, the impact applying member should be prepared in steps shown in FIGS. 20A to 20G. First, the movable base portion 1724 having a groove or recess area is prepared as shown in FIG. 20A, and the deformable member 1723 and the piezoelectric body 1720 are placed on the movable base portion under a predetermined atmosphere of reduced pressure (FIG. 20B) Furthermore, the piezoelectric body is placed on the deformable member in the figure, but it may be placed under the deformable member. Then, the sealing member 2910 and the movable base portion 1724 are bonded together through the deformable member 1723 under a predetermined atmosphere of reduced pressure (FIGS. 20C and 20D). For bonding them together, for example, anode bonding can be used. Furthermore, FIGS. 20E, 20F and 20G show the aspect of sealing spatially.

Figure 21:
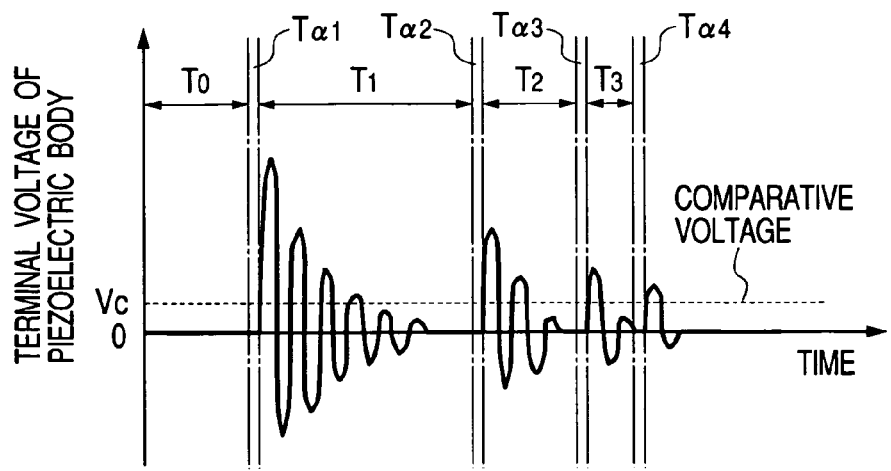
FIG. 21 shows an example of the output signal according to the present invention.

The aspect of collision will be described with reference to FIG. 21. In the configuration described above, as shown in FIGS. 22A and 22B, when the movable base portion is fallen from an altitude of H0, the impact portion 1727 is collided against the sheet material on the platen after a period of time T0, and the impact portion recoils through a period T.alpha.1 over which the sheet material is deformed (plastic deformation and elastic deformation), and rises into the space to an altitude H1 along the bearing portion accepting a uniaxial movement, and then starts to fall again, and collides against the sheet material 1010 again through a period of time T1 over which it stays in space, and the impact member recoils again through a period of time T.alpha.2 over which the paper is deformed, and as the recoil body (including piezoelectric body, elastic deformable member, movable base portion, movable axis and impact portion) undergoes gradual reduction in the recoil height while repeating the above operations, the elastic deformable member has its momentum changed by the impulse occurring at the time when the recoil body collides against the sheet material, namely the elastic deformable member is transited from the static state to the dynamic state to start vibrating as shown in FIGS. 22A and 22B, and thereafter the vibration has its amplitude gradually reduced with time due to attenuation by the viscous resistance of the flat spring vibration system, and the recoil body undergoes the process described above in which the collision and the fall are repeated, and finally falls onto the sheet material and stops.

In the repetitive process described above, the elastic deformable member occurring at the time when the impact portion collides against the sheet materials creates natural vibration.

This is because the periphery of the elastic deformable member is kept under an atmosphere of reduced pressure by the sealing member 2910 and the like. In repletion of collision and recoil, for the calculation of the recoil period, for example, how many periods of vibration are included in the period of time T1 may be counted (six periods in the case of FIG. 22A), or how many periods of vibration are included in the period of time T1+T2, the period of time T1+T2+T3 or the period of time until the member is substantially in the static state may be calculated. The type of sheet material can be detected based on the calculated value.

Since the piezoelectric current occurs in proportion to the deformation speed of the piezoelectric body, the piezoelectric body placed on the surface of the flat spring also create similar vibration in response to the vibration of the flat spring occurring at the time of collision, and the piezoelectric body creates tensile strain and compressive strain alternatingly with the vibration, and the piezoelectric current is changed into an alternating current due to the above strain created alternatingly. By picking up the alternating current as a voltage from the electrode terminal of the piezoelectric body, the terminal voltage shown in FIGS. 22A and 21 was obtained.

Figure 22A:
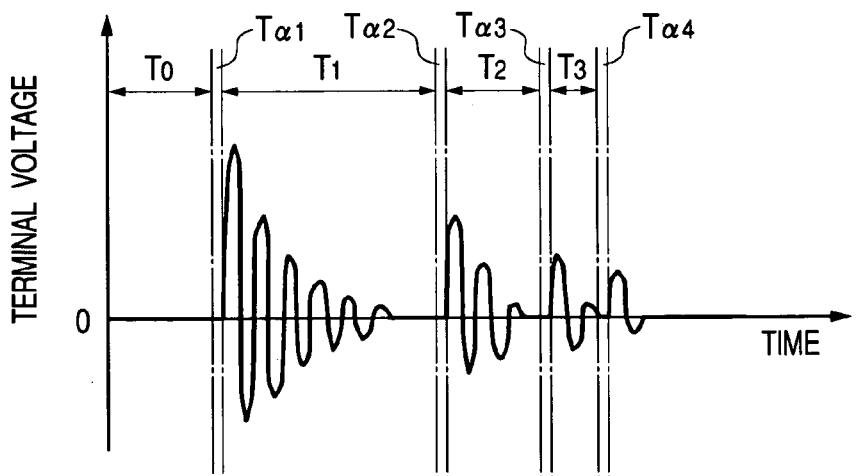
FIGS. 22A and 22B show examples of the output signal according to the present invention.
Figure 22B:
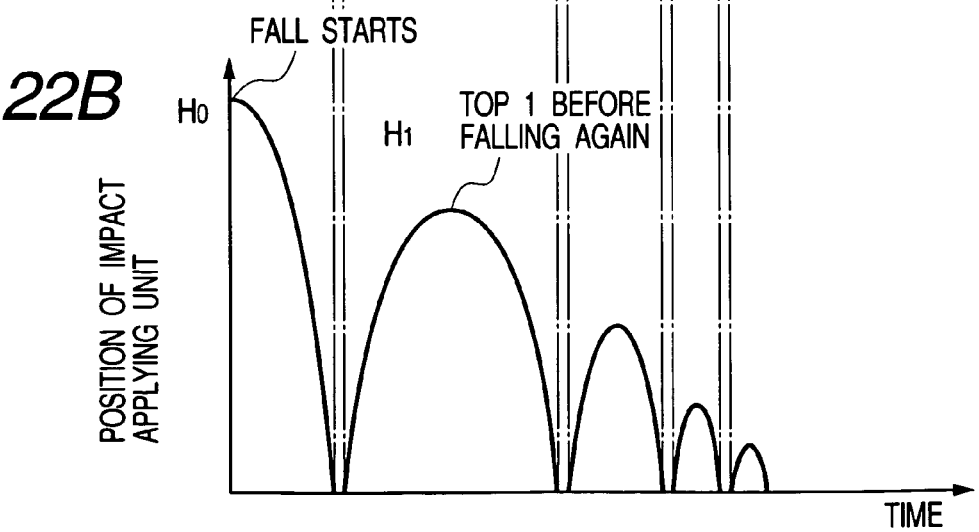

The number of the pulses after the collision is counted over the period of time T in this case, but it may be counted over only the period of time T1 as shown in FIGS. 22A and 22B, or over the period of time T1+T2.

Furthermore, the piezoelectric current is converted into voltage and used in this embodiment, but a change in piezoelectric current may be used to carry out detection.

In addition, in the vibration system of the elastic deformable member such as a flat spring, air resistance remaining in the periphery of the member, which occurs in proportion to the vibration velocity, acts to attenuate the vibration, and it is therefore desirable that the flat spring and piezoelectric body are placed in the atmosphere of reduced pressure to prevent attenuation of the amplitude of the natural vibration of the flat spring occurring at the time of collision, wherever possible.

Preferably, the vibration has increased amplitude, and has the amplitude reduced and eliminated before next collision occurs. By this operation, if a terminal voltage generated by the vibration amplitude of the flat spring 2 is selected by a comparator 2319 shown in FIG. 23 while the recoil body is rising into the space, the number of instances where the terminal voltage equal to or higher than the comparative voltage can be pulsed is increased, namely the number of pulses inputted to the counter can be increased, thus making it possible to detect accurately the recoil height determined from the number of pulses.

In addition, the vibration amplitude of the flat spring is increased due to the impulse occurring at the time of collision, and therefore the weight of the flat spring should be reduced.

Attenuation of the flat spring is caused by the viscous resistance of residual gases in the atmosphere of reduced pressure, but as a method for attenuating the vibration of the flat spring after the voltage is reduced to the comparative voltage or lower, for example, in addition thereto, an alternating voltage with the phase shifted by 180 (relative to the vibration amplitude of the flat spring may be applied, or a direct voltage may be applied to the piezoelectric body.

Needless to say, if collision and recoil are once repeated, and the level of attenuation of amplitude is small, it is preferable that means for temporarily stopping the vibration is secured in order to detect the type of sheet material for two or more pieces. For example, the amplitude may be forcibly attenuated by applying a null voltage to the piezoelectric body, or by applying thereto an inverse voltage. Alternatively, when the piezoelectric body exist on the compression side due to vibration, a voltage is applied to the piezoelectric body so that the piezoelectric body extends in the longitudinal direction, and on the other hand, when the piezoelectric body exist on the tension side, a voltage is applied so that the piezoelectric body contracts in the longitudinal direction. By such operations, the amplitude can be attenuated forcibly.

Furthermore, for how the impact applying member is fallen, not only gravity but also a spring 2718 may be used as shown in FIG. 17.

Another method for measuring the recoil period using the natural frequency of the elastic deformable member will now be described.

Figure 23:
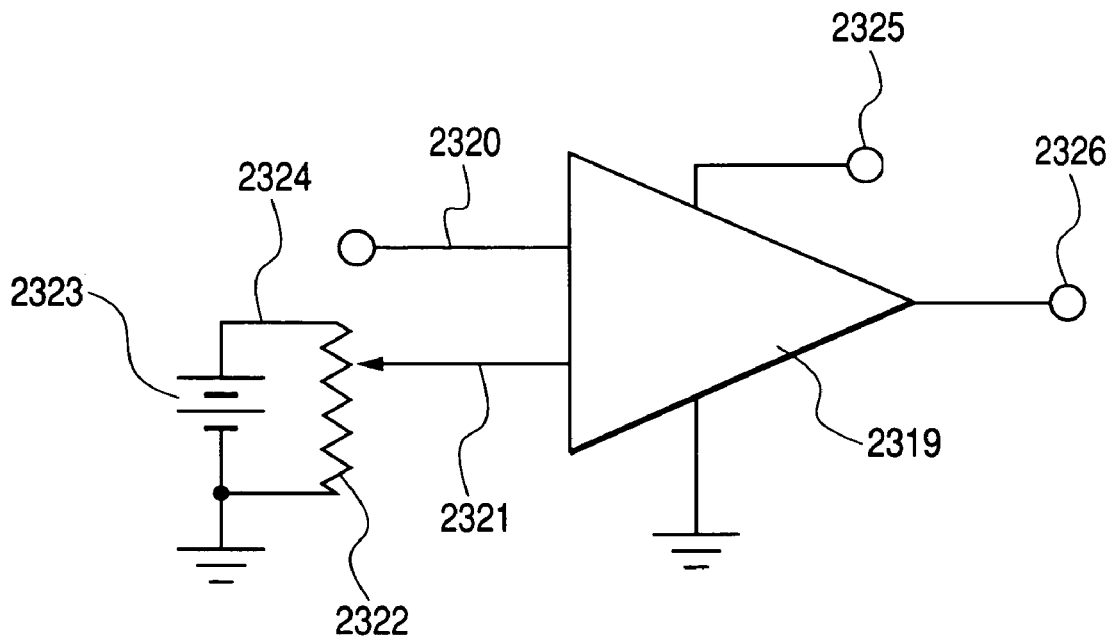
FIG. 23 is an example of a signal processing circuit according to the present invention.

Detection is carried out with an alternating change in terminal voltage of the piezoelectric body placed on the surface of the elastic deformable member shown in FIG. 22A, and the terminal voltage is introduced in the electric comparator 2319 shown in FIG. 23, and the terminal voltage higher than a predefined comparative voltage (see FIG. 21) is taken out from an output terminal 2326 of the comparator 2319.

Figure 24:
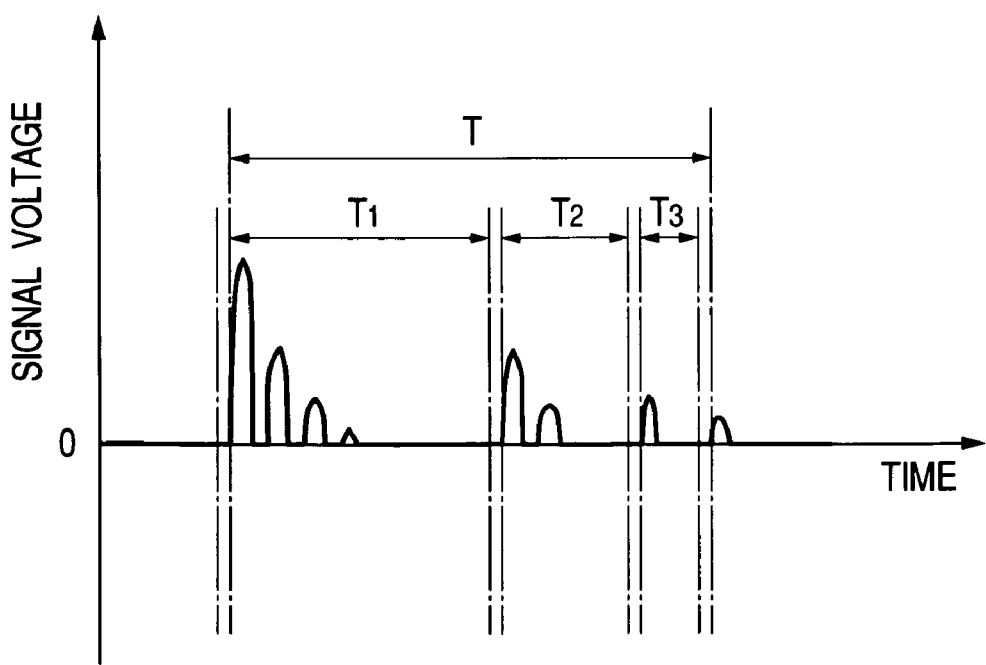
FIG. 24 shows an example of the output signal according to the present invention.

That is, the terminal voltage passing through the comparator may be processed into a signal voltage as shown in FIG. 24, and thereafter the signal voltage may be pulsed (not shown), and the pulse may be counted by a counter during a defined period of time after the collision (e.g. T, T1, T1+T2 or T1+T2+T3, or it may be defined as 1 second and the like as a matter of course). If taking advantage of the fact that the counted value varies depending on the type of sheet material, the type of sheet material can be determined. Furthermore, reference numeral 2319 denotes the electric comparator, reference numeral 2320 denotes an input terminal, reference numeral 2321 denotes a comparative voltage, reference numeral 2322 is resistor for making a setting of the comparative voltage 2321 by separation of resistance, reference numeral 2323 is a direct current power supply for taking out the comparative voltage 2321, reference numeral 2324 denotes a lead wire, reference numeral 2325 denotes a supply power source for the comparative circuit 2319, and reference numeral 2326 denotes the output terminal of the comparator 2319.

Alternating signal voltages generated at time T1, T2 and T3, respectively, are pulsed during a period of time T set as shown in FIG. 24 (longer than the period of time until the impact member falls and becomes at rest on the paper), and the recoil period is determined from the number of the pulses (the number of pulses occurring between the instant when the impact member starts to fall onto the paper and the instant when the impact member falls and becomes at rest on the paper), whereby the type of sheet is detected.

Furthermore, if an impact absorber is placed, vibration can be attenuated forcibly. The impact absorber includes, for example, a groove provided on the substrate, a magnet or a rubber.

Specific Example of Configuration of Type Determining Apparatus

Figure 12:
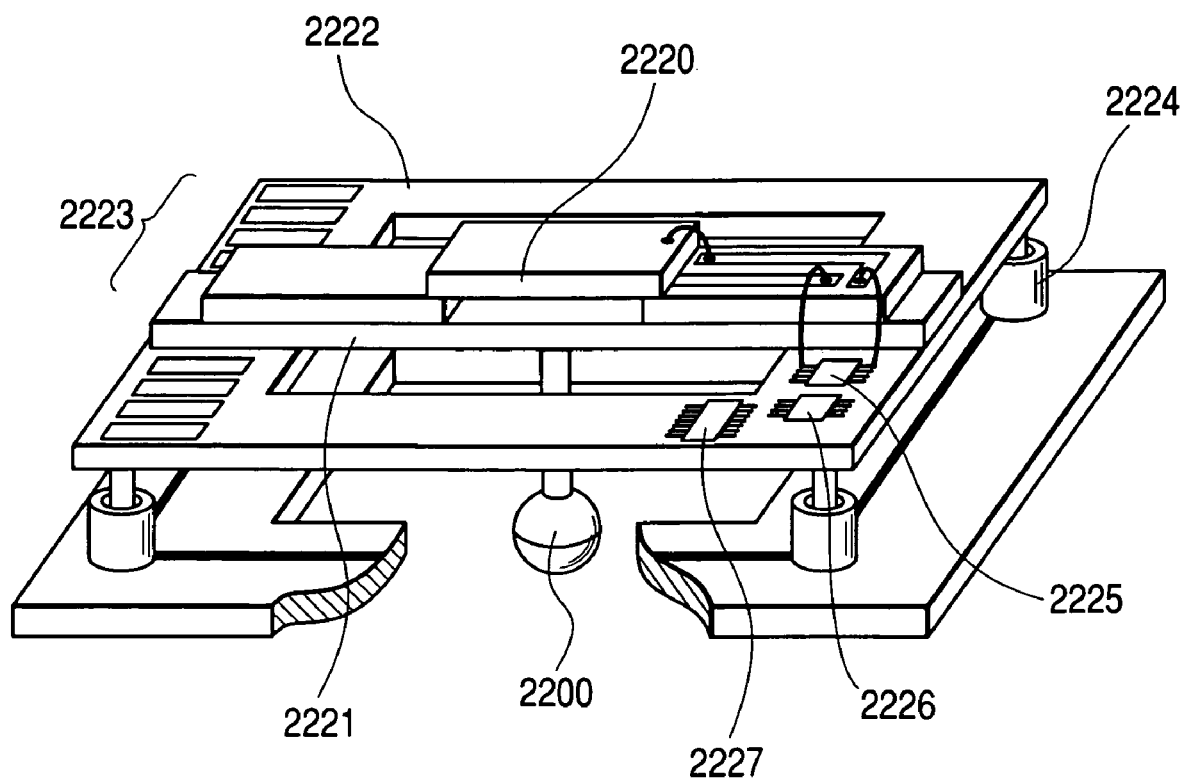
FIG. 12 illustrates the signal output apparatus according to the present invention.

An example of the configuration of a module (sensing unit) in which it is possible to apply a predetermined impact to the sheet member, and then output a signal by the impact will be described with reference to FIG. 12.

An impact applying unit 2200 is bonded to the elastic deformable member 2221, and a piezoelectric sensor 2220 is fixed to this elastic deformable member as a center beam with both ends of the length as fixed ends. The both ends of the piezoelectric sensor are fixed, whereby the elastic deformable member is significantly deformed at the time of application of impact/detection of impact, and thus a large amount of strain can be given to the piezoelectric sensor, and therefore detection sensitivity is enhanced.

This elastic deformable member 2221 is fixed on a Si substrate 2222. A voltage conversion circuit 2225, a filter circuit 2226 and an amplifier 2227 are provided as IC on this Si substrate.

Wirings drawn from the upper and lower electrodes of the piezoelectric sensor 2220 on the elastic deformable member 2221 are connected to the voltage conversion circuit 2225. An electric signal is outputted to the outside of the module from an output signal electrode 2223. Also, a mechanism involved in driving for applying an impact to the sheet member from the impact applying unit 2200 is provided, and in this embodiment, electromagnetic force is used for the mechanism. Specifically, a solenoid 2224 for driving rectilinearly a movable axis (movable iron core) made of magnetic material is used.

For application of impact, for example, a direct current is passed through the solenoid, whereby an electromagnetic force is generated to keep the impact portion from the medium (push action of the solenoid), and the current is discontinued, whereby the impact portion is released and fallen by gravity, so that the impact portion is collided against the recording medium to apply an impact. Alternatively, the impact portion is kept from the medium by means of a spring or the like (not shown), and then the impact portion is collided against the recording medium by pull action of the solenoid to apply an impact. For driving for applying an impact in this way, the elastic force of the elastic body, falling by gravity, displacement of the piezoelectric element and the like can be used in addition to the electromagnetic force, and some of these may be used in combination.

Figure 52:
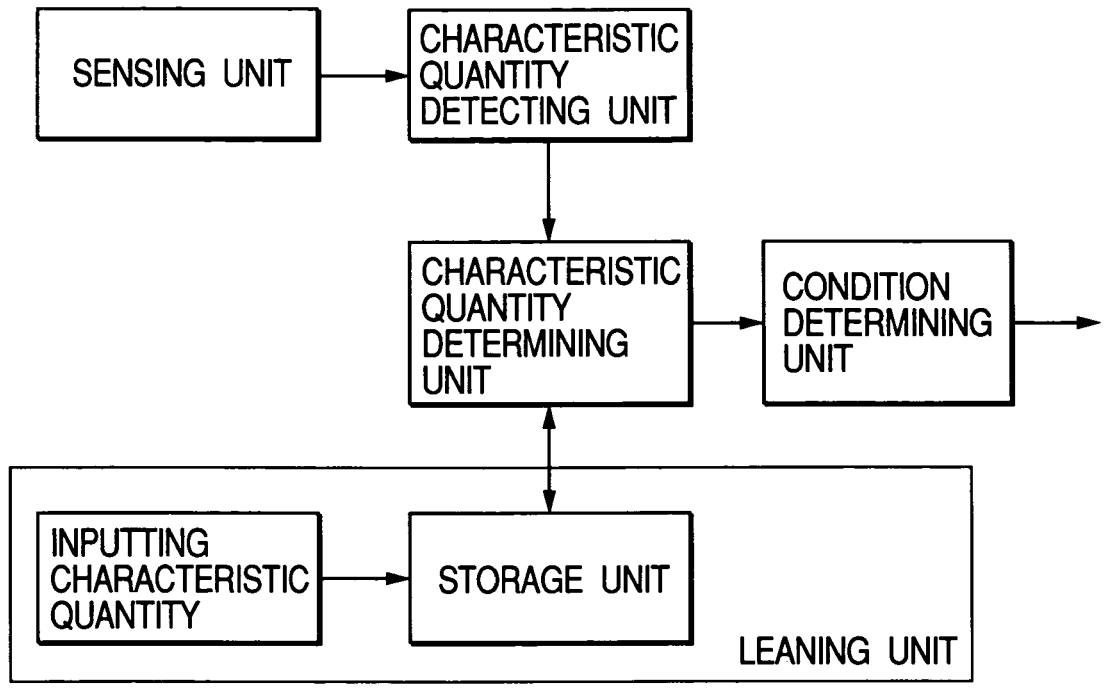
FIG. 52 is a flowchart of data processing of the output signal according to the present invention.

For detection of the impact, a strain is created in the piezoelectric sensor due to the deformation of the elastic deformable member by the impact received by the impact portion from the sheet material, and the strain is converted into a voltage signal and detected as a change in the voltage signal with time, and is deprived of undesired frequency-band noises by the filter 2226 as necessary, and is thereafter amplified by the amplifier 2227, and is then outputted as a signal. Furthermore, the method in which the signal from the sensing unit is used to determine the type of sheet material is shown in FIG. 52. The signal from the sensing unit is inputted to a characteristic quantity detecting unit. In the characteristic quantity detecting unit, the characteristic quantity different for each type of medium is extracted from the output signal. This characteristic quantity includes the number of peaks of the signal occurring until attenuation is reached, time required until attenuation is reached, the voltage value at the peak, the degree of variety of a plurality of peaks, and time intervals between a plurality of peaks.

Figure 53:
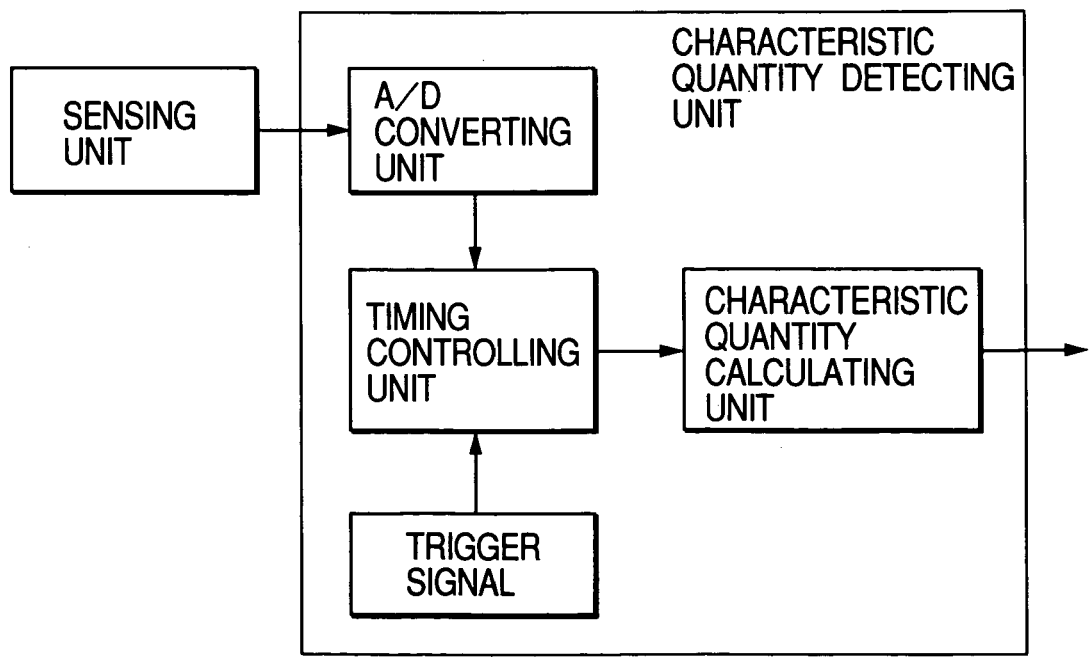
FIG. 53 is a flowchart of data processing of the output signal according to the present invention.

Specifically, in the characteristic quantity detecting unit, the signal from the sensing unit is converted into a digital signal by the A/D converting unit if it is an analog waveform signal, as shown in FIG. 53. In addition, a reference signal for voltage or time is inputted as a trigger signal, and the time and voltage for each peak is digitized based on the waveform converted into a digital signal in the timing controlling unit and the trigger signal. Then the characteristic quantity is extracted.

Thereafter, the characteristic quantity is determined in a characteristic determining unit, and the type of sheet material is determined in a condition determining unit. Furthermore, in the characteristic quantity determining unit, the data table stored in a storage unit is compared with the characteristic quantity sent from the characteristic quantity detecting unit to determine the characteristic quantity to be used in determination of the type. Here, a leaning unit is a unit in which the characteristic quantity prepared in advance is stored as a data table.

Third Embodiment

Apparatus and System having Capability of Determining the Type of Sheet Material Apparatuses that will be described in this embodiment include image forming apparatuses comprising the detection unit described above (printer, copier, facsimile, etc.), image readers (scanner, page reader), sheet material conveying apparatuses, sheet material number counting apparatuses, sheet material type classifying apparatuses, sheet conveying apparatuses, sheet feeders and sheet payload apparatuses (hereinafter, all these apparatuses may be described as "image forming apparatus, etc." in abbreviation form). The type of sheet material may be determined in the image forming apparatus, etc. or it may be determined by another external apparatus (e.g. computer) connected to the image forming apparatus, etc.

After the type of sheet material is determined, items to be controlled are controlled so that the most suitable setting for the sheet material is obtained.

Items to be controlled include, for example, the amount of ink to be discharged and the space between conveying rollers during conveyance of the sheet material, temperature conditions when the image is formed on the sheet material (e.g. temperature conditions at the time of fixation of toner) In addition thereto, the items to be controlled include conditions for conveying the sheet material (conveyance speed, pressure between conveying rollers, space between rollers), paper feed conditions for sorting and feeding paper (sorter), conditions for drying the sheet material after formation of images and conditions about staples.

Figure 54:
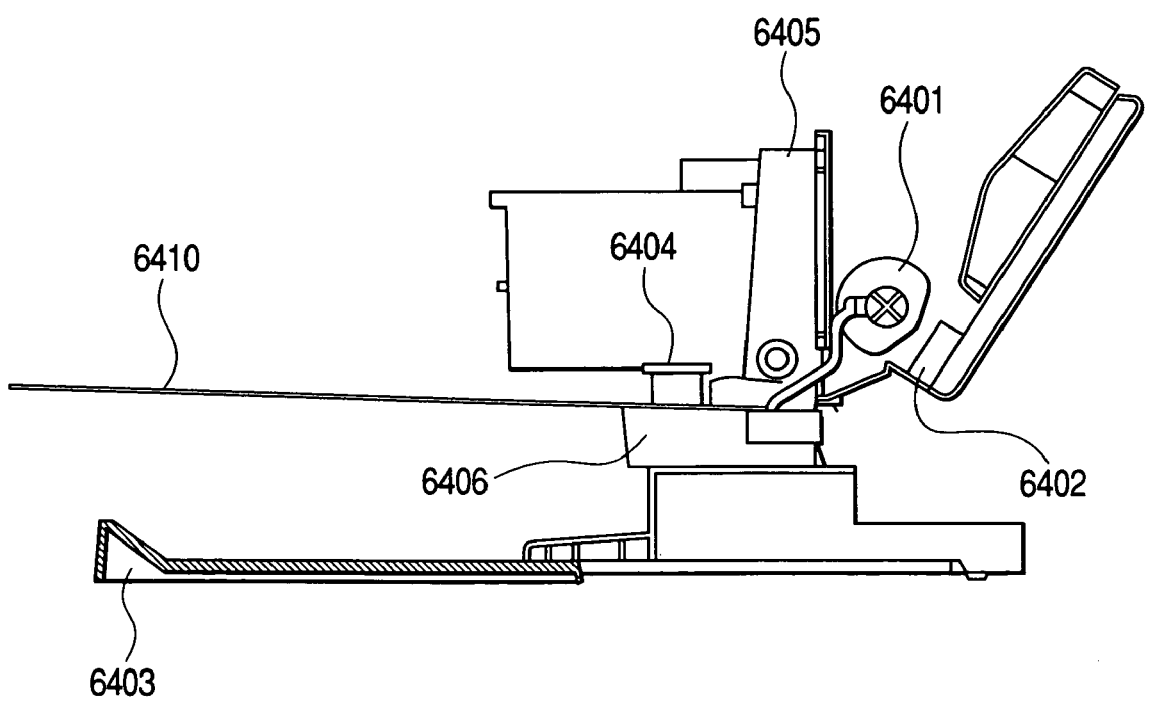
FIG. 54 illustrates the present invention.

Furthermore, whether or not printing is possible may be determined based on the signal from the detection unit. Also, an alarm (e.g. an alarm indicating that the print mode designated by the user or defined automatically does not match the type of sheet material) may be issued to the user based on the signal from the detection unit without setting conditions for the item to be controlled. Needless to say, a plurality of items to be controlled may be set so that they provide conditions suitable for the sheet material. For example, when the type of sheet material has been determined, conditions for conveying the sheet material may be controlled, and conditions for record heads (e.g. the amount of liquid to be discharged from the discharging head). Furthermore, for example, FIG. 54 shows a schematic sectional view of an ink jet printer. Reference numeral 6401 denotes a roller for feeding paper, reference numeral 6402 denotes a detection unit, reference numeral 6403 denotes a delivery tray, reference numeral 6404 denotes a printing head, reference numeral 6405 denotes a circuit portion, reference numeral 6406 denotes a conveyance mechanism portion, and reference numeral 6410 denotes a sheet material. The impact is applied, for example, using the roller 6401.

Control of the amount of ink to be discharged will be described in detail below.

After the type of sheet material is detected, the amount of ink to be discharged is controlled (adjusted) so that printing is performed in the optimal mode. The print mode is defined by the CPU placed inside or outside the image forming apparatus. Transmission and reception of data signals to and from the outside can be omitted if the CPU is placed inside. Needless to say, man may input the print mode from the external computer in consideration of the type. Thereby, the operation by man of sending information such as the type of sheet and the print mode for each printing paper can be omitted, thus making it possible to eliminate an undesirable situation in which printing is not carried out in the optimal mode due to a human error. It is possible to detect the type of sheet material and define the print mode for each piece of printing paper, or plurality of pieces of printing paper or for any number of pieces of printing paper. It is also preferable that whether or not the type of sheet material is detected and determined can be determined in advance in the image forming apparatus itself or from the external computer connected thereto.

Information on the type of printing paper and printing mode is sent from the computer connected to the image forming apparatus (e.g. printer) to the the image forming apparatus, thus making it possible to carry out printing based on the information sent.

The image forming apparatus according to the present invention comprises, for example, the signal output apparatus described above, image forming means for discharging an ink to a sheet material to form an image, and ink discharge controlling means for determining the type of the sheet material based on the signal from the signal output apparatus, thereby controlling the amount of ink to be discharged. The ink discharge-type printer mentioned herein is referred to as an inkjet printer, and is described in, for example, U.S. Pat. No. 6,276,776.

Also, the image forming apparatus according to the present invention comprises, for example, the signal output apparatus described above, image forming means for forming a toner image on a sheet material, fixing means for heat-pressing the toner image against the sheet material to fix the toner image on the sheet material, and temperature controlling means for determining the type of the sheet material based on the signal from the signal output apparatus, thereby controlling the temperature of the fixing means.

Also, the image forming apparatus according to the present invention comprises, for example, the signal output apparatus described above, image forming means for forming an image on the sheet material by a thermal head, and power controlling means for determining the type of the sheet material based on the signal from the signal output apparatus, thereby controlling the power supplied to the thermal head.

Fourth Embodiment

Information Output Apparatus

In this embodiment, the case where an impact is applied to the target other than sheet materials. Specifically, for the purpose of examining the state (e.g. the amount of residual ink and defect of the ink outlet) of a liquid container used in the image forming apparatus (e.g. inkjet printer), the impact is applied to the liquid container. The impact mentioned herein is an external force other than vibration by the piezoelectric element. For the method for applying the impact, the above method using gravity and a spring may be used.

Referring to FIG. 1, for example, the information output apparatus is such that the impact applying unit 1000 is collided against the liquid container 1010 to output information about the content of the liquid container by the detection unit 1020 mounted on the liquid container. Furthermore, the detection unit is not necessarily mounted on the liquid container itself as long as information about the state of the liquid container can be outputted. For example, this holds true with the case where an acoustic wave occurring by the impact is detected.

EXAMPLES

The present invention is described below in more detail with reference to Examples.

Signal Output Apparatus

Example 1

Figure 25:
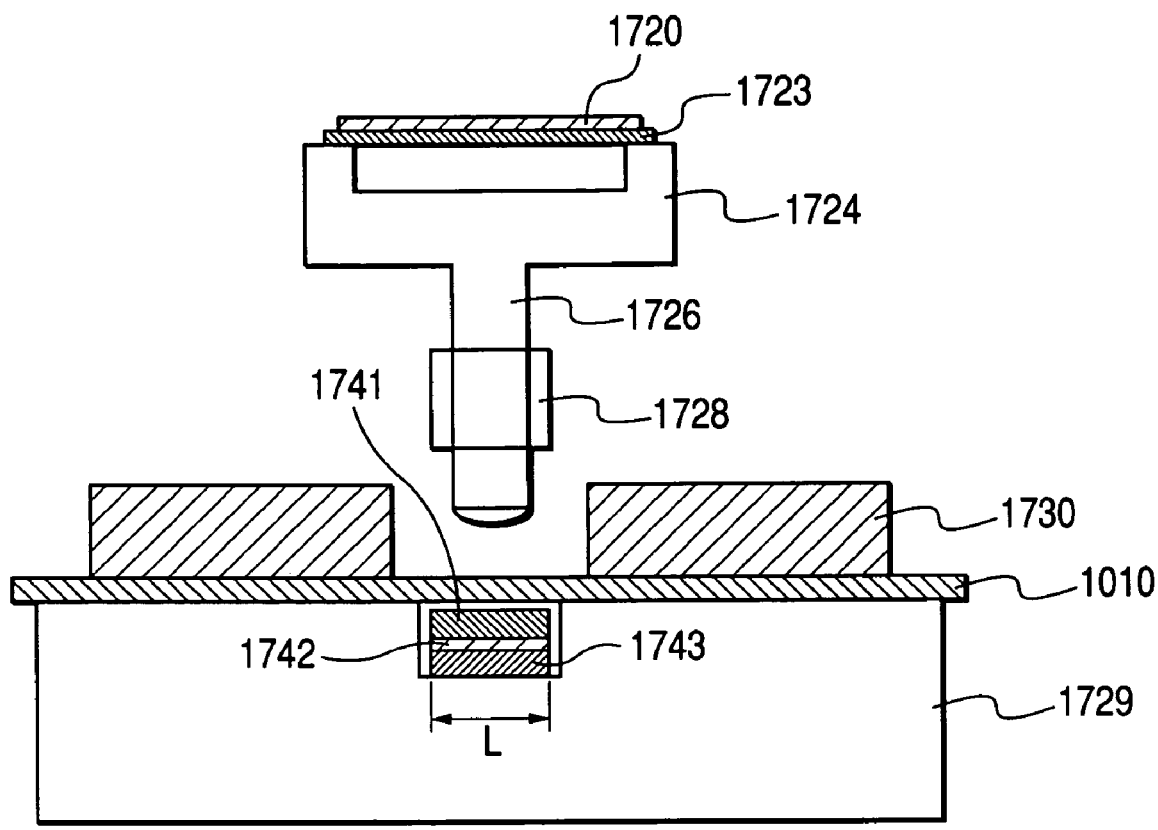
FIG. 25 illustrates the signal output apparatus according to the present invention.

A signal output apparatus using an impact applying unit and a detection unit shown in FIG. 25 will be described. Reference numeral 1720 denotes an upper piezoelectric element, of which material is PZT (titanic lead zirconate). Reference numeral 1723 denotes an elastic deformable member, of which material is a bronze plate. Reference numeral 1724 denotes an impact applying unit, and the diameter of a cylinder portion 1726 is 3.5 mm. The front edge of the impact applying unit has a curved surface. Reference numeral 1728 denotes a bearing portion, of which material is a fluorine resin having a small friction coefficient. Reference numeral 1730 denotes a paper holding portion, which holds paper with a force of 8 g/cm.sup.2.

Reference numeral 1010 denotes a paper, and reference numeral 1729 denotes a base material made of brass. The base material is provided with a recess, and an impact receiving material is provided in the recess. The impact receiving material has a three-layer structure. Reference numeral 1741 denotes a brass, reference numeral 1742 denotes a lower piezoelectric element (C91 manufactured by Fuji Ceramics Co., Ltd.), and reference numeral 1743 denotes a rubber vibration insulator. Furthermore, for the vertical positions of the surfaces of the base material 1729 and the impact receiving material 1741, the position of the impact receiving material is lower by about 0.1 mm. Also, the piezoelectric element was prevented from contacting the side face of the above described recess. An adjustment was made so that the impact applying unit would almost vertically collide against the paper. Furthermore, the weight of the impact applying unit was about 6.6 g. In the following step, an adjustment was made so that the distance of drop covered by the impact applying unit would be 2.5 mm. L in the figure represents a length of 5 mm.

Experiments were conducted to whether or not a signal could be outputted as a paper serving as the sheet material for each of the plain paper and the photo paper. Furthermore, LC 301 and PR 101 both manufactured by Canon Inc. were used as the plain paper and the photo paper, respectively.

Figure 26A:
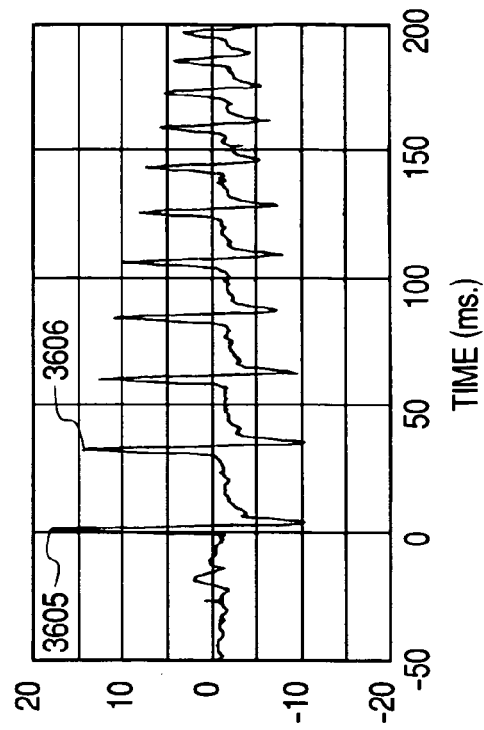
FIGS. 26A, 26B, 26C and 26D show examples of the output signal according to the present invention.
Figure 26C:
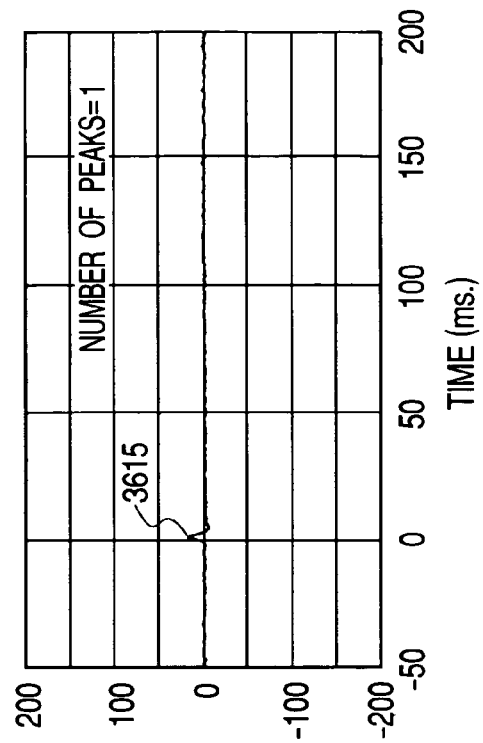
Figure 26B:
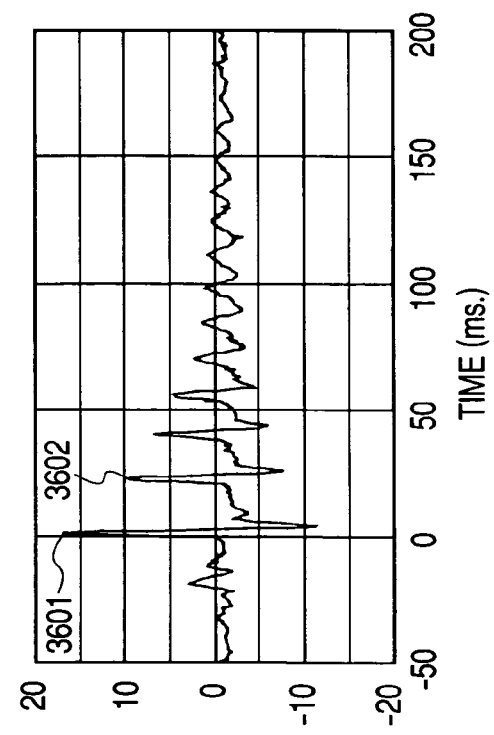
Figure 26D:
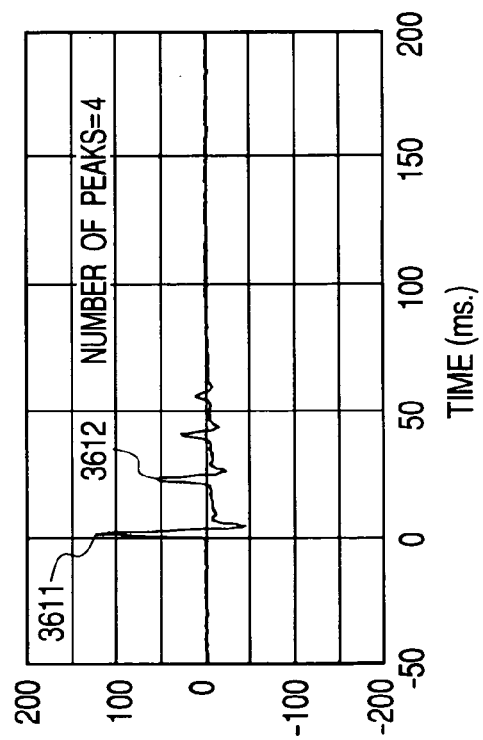

The results are shown in FIGS. 26A and 26D. FIG. 26A shows a signal waveform from the upper piezoelectric element when the impact is applied to the plain paper, and FIG. 26B shows a signal waveform from the lower piezoelectric element when the impact is applied to the plain paper. FIG. 26C shows a signal waveform from the upper piezoelectric element when the impact is applied to the photo paper, and FIG. 26D shows a signal waveform from the lower piezoelectric element when the impact is applied to the photo paper.

As shown in these figures, a signal output apparatus outputting a signal by the impact applied to the sheet material was obtained.

Furthermore, in this Example, the rubber is provided on the lower side of the lower piezoelectric element 1742, but the rubber may be provided on the both sides, or may not be provided as long as the signal can be detected. Also, the vertical position of the surface of the impact receiving material 1741 is lower than the vertical position of the surface of the base material 1729, but the converse is also possible. However, in the case where the vertical position of the impact receiving material is higher, the height should be kept at an appropriate level so as not to hinder the conveyance of the sheet material. Also, the size of the impact applying unit contacting the sheet material is preferably smaller than or equal to the size of the lower piezoelectric element. Also, in this Example, the width of the impact receiving material is smaller than that of the recess provided in the substrate, and therefore a gap is formed, but the gap may be filled with resin and the like. Also, the width of the recess provided in the substrate may be equalized with the width of the impact receiving material.

Example 2

Method for Determining the Type of Sheet Material

Whether or not the type of sheet material can be determined by the output signal obtained in the Example 1 was examined.

In this Example, the piezoelectric element is placed on both upper and lower sides of the sheet material, but it may be placed on only one side as a matter of course.

Using Output Signal from Upper Piezoelectric Element

For the peak value, there was almost no difference between signals 3601 and 3605 in the first collision, but there was a difference of about 5 mV between the signals 3602 (plain paper) and 3606 (photo paper) in the second collision, and therefore the type could be well determined.

For the number of peaks, the number of instances where a signal of 10 mV or greater was outputted was counted, the result was one time for the plain paper, and four times for the photo paper, and it was found that the type can be well determined by the number of peaks.

For the peak interval (recoil period), the time interval between the first collision and the second collision is observed. There was apparently a sufficient difference between the case of plain paper (interval between signals 3601 and 3602) and the case of photo paper (interval between signals 3605 and 3606). That is, it was found that the peak interval can also be used to determine the type of sheet material.

Using Output Signal from Lower Piezoelectric Element

For the peak value, there was a difference of about 100 mV between signals 3611 and 3615 in the first collision, and therefore the type could be well determined.

It was found that the number of peaks can also be used to determine well the type as apparent from FIG. 26B (the number of peaks=4) and FIG. 26D (the number of peaks=1).

For the peak interval (recoil period), the time interval between the first collision and the second collision is observed. There was apparently a sufficient difference between the case of plain paper (interval between signals 3611 and 3612) and the case of photo paper (interval between signals 3605 and 3606). That is, it was found that the peak interval can also be used to determine the type of sheet material.

As a matter of course, for improving the accuracy in determination of the type of sheet material, both the peal interval and peak value can be used to determine the type.

Example 3

The Number of Peaks

As one example of the present invention, a printing paper identifying apparatus used in the inkjet printer will be described based on the drawings.

It will be described with reference to FIG. 4. This figure is a schematic diagram of a paper delivery mechanism used for aligning the edge of the printing paper from a tray (not shown) in the inkjet printer. Reference numeral 1410 denotes a sheet member (printing paper in the case of this Example), reference numeral 1401 denotes a conveying roller (pinch roller), reference numeral 1403 denotes a guide for aligning the edge of the printing paper, reference numeral 1400 denotes a pinching guide for having the printing paper pinched, and reference numeral 1420 denotes an piezoelectric body.

Figure 5:
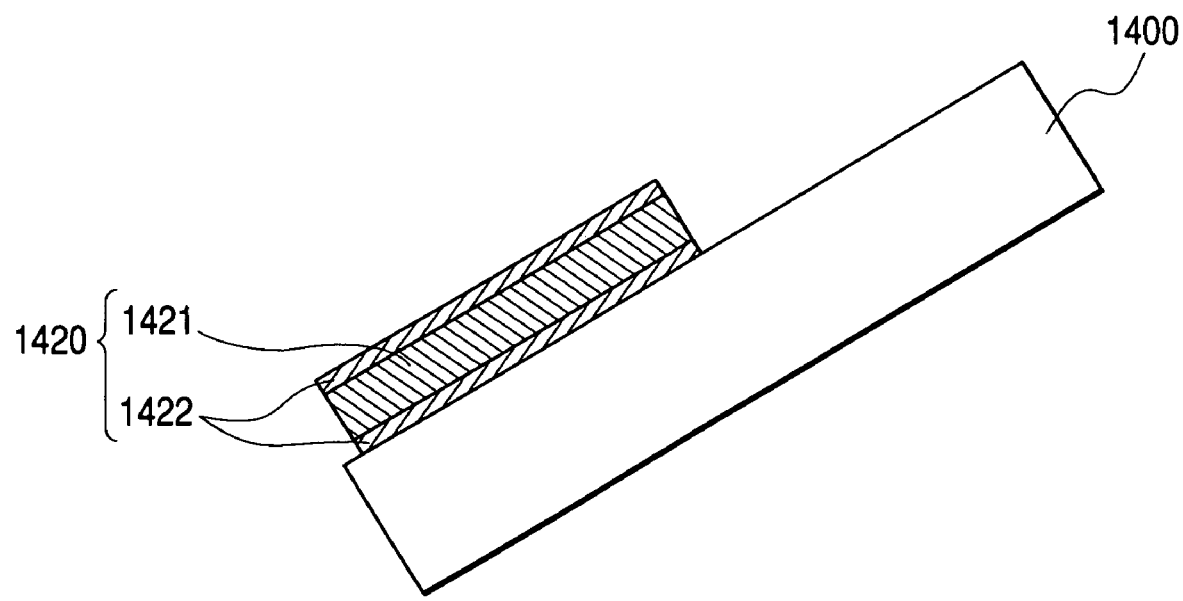
FIG. 5 illustrates the signal output apparatus according to the present invention.

FIG. 5 is a magnified view of the piezoelectric body 1420 and the pinching guide 1400. The piezoelectric body 1420 in this Example has a PZT (titanic lead zirconate) film vertically pinched by a platinum electrode 1422. The piezoelectric body had a size of 20 mm long, 7 mm wide, 0.3 mm thick.

Data before having the printing paper 1410 pinched (FIG. 13) is read in the processor as an initial state before the printing paper 1410 is fed from the tray to the printer in this Example.

Furthermore, the reading in the initial state may be omitted.

Figure 13:
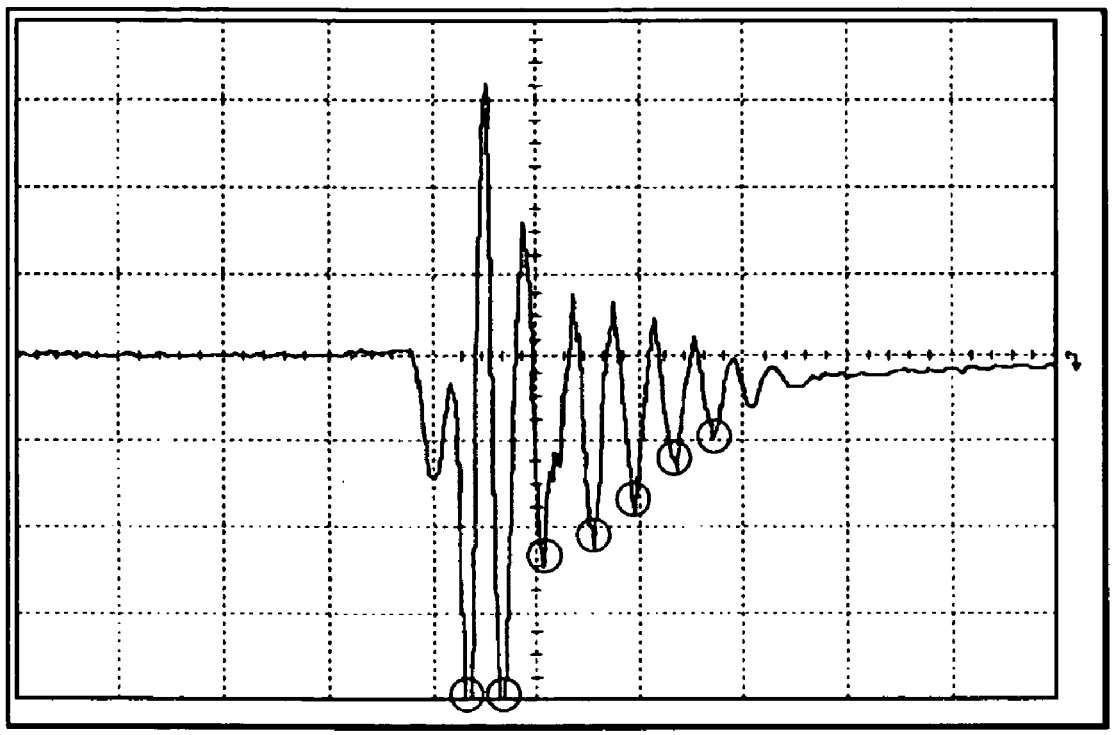
FIG. 13 shows an example of the output signal according to the present invention.

For the data at this time, values of 5V or greater in the output voltage on the negative side are analyzed on the time axis while ignoring the positive side (upper side) in FIG. 13.

As a result, about seven peaks were observed with the first peak of about 20 V, second peak of about 20V, third peak of about 10 V and fourth peak of about 10 V in the absence of printing paper. Thereafter, the printing paper 1410 (plain paper) is inserted into the edge guide 1403, and the pinching guide 1400 causes the printing paper 1410 to be pinched between itself and the pinch roller 1401.

Figure 9:
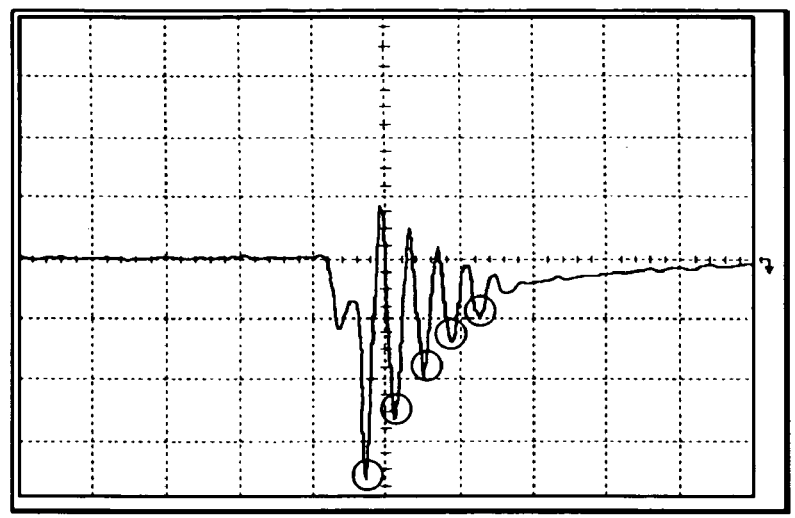
FIG. 9 shows an example of the output signal according to the present invention.

At this time, the printing paper 1410 is pressed (i.e. the impact is applied) by the pinch roller 1401, and a voltage is outputted from the piezoelectric body 1420 located near the edge of the pinching guide 1400 (FIG. 9). The output voltage has five peaks, and in the initial three peaks thereof, the first peak represents 18.5 V, the second peak represents 13.5 V, and the third peak represents 10 V.

This data is recorded as data for identifying the type of sheet. Similar experiments were conducted using the coated paper and the photo paper, and output data shown in FIG. 10 (the number of peaks=3) and output data shown in FIG. 11 (the number of peaks=2) were obtained, respectively.

In the processor, the signal voltage in the initial state with no printing paper 1410 and the number of peaks of the voltage outputted at the time of pinching the printing paper 1410 were stored in the data table in advance, thus making it possible to identify the sheet material by comparing the table with output data. Also, if the signal in the initial state is used, whether or not the printing paper is placed in a predetermined position can also be determined. Furthermore, the type of sheet may be determined by comparing voltage values at respective peaks, instead of determining by the number of peaks as described above. A period of time until attenuation is required can be calculated from the attenuation curve of waveform and compared to identify the sheet, or the sheet can be identified from the degree of difference between the first peak after application of impact and the subsequent second peak.

A computing apparatus connected to the printer carries out rendering suitable for the determined type of sheet for the print mode of inkjet, and the printer has the printing paper 1410 conveyed to the position opposite to the print head by the paper delivery mechanism to start printing.

If printing is carried out for a large number of sheets, the processor identifies the type of sheet and sends sheet type data to the computing apparatus in the printer by carrying out processing similar to that described above when printing is carried out for one sheet. This is because for normal printing, it takes about 3 seconds to do printing for one sheet if the level is about 20 ppm.

Also, in this Example, the pinching guide 1400 is used as a pinch roller, but different configurations are possible. For example, the pinching guide may be provided separately on the pinch roller axis.

Also, (VA−VB)/VA, in which VB represents an output voltage when the sheet is pinched, and VA represents a voltage in the initial state, and VB is compared with the value of VA, may be used. In this case, data no longer depends on the variation of the initial state. Furthermore, in the image forming apparatus, there are cases where the sheet material is stopped for detection of edges, and at this time the impact is preferably detected.

Example 4

Peak Value

Figure 27:
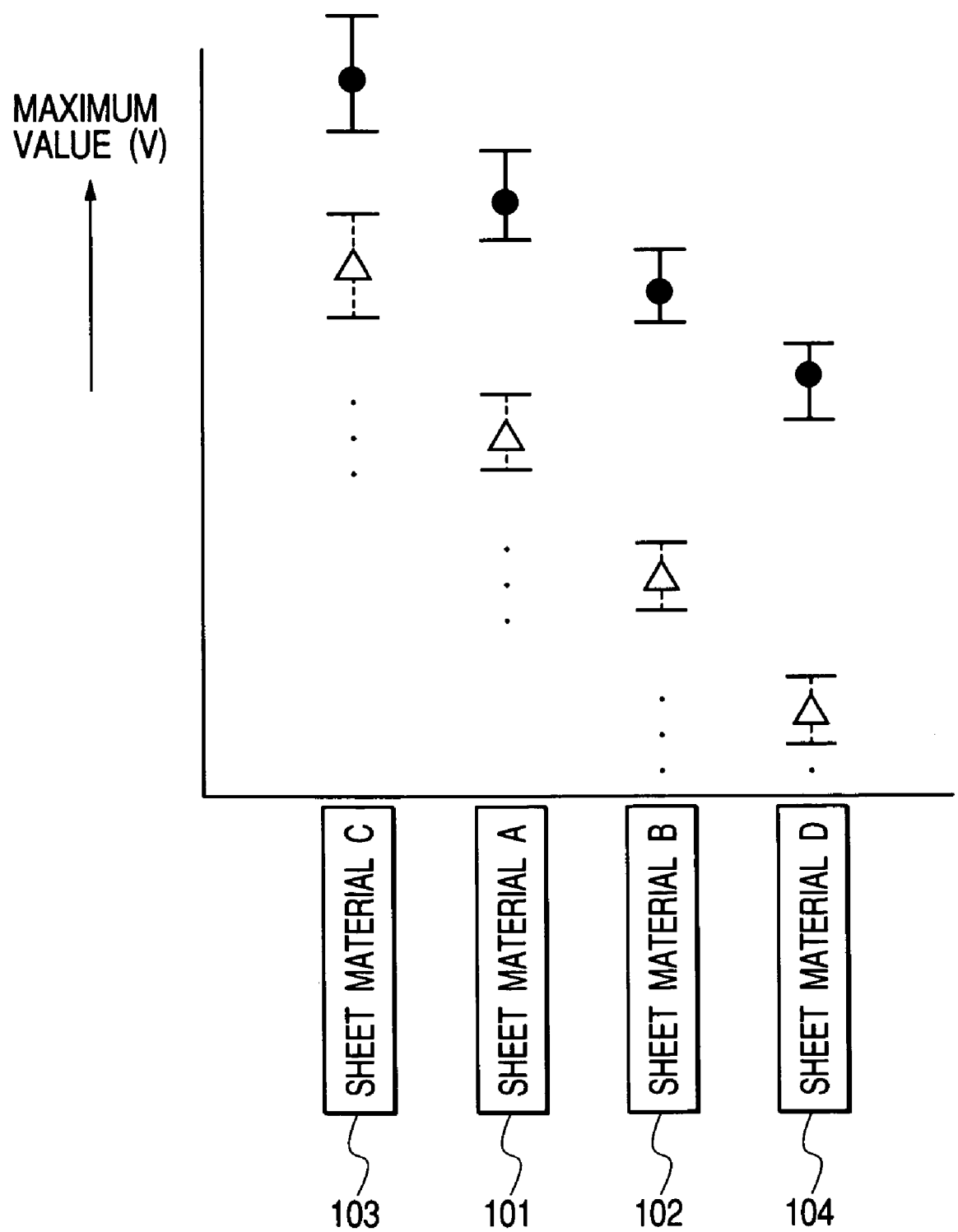
FIG. 27 illustrates the present invention.

When the impact applying unit comprising the piezoelectric element was collided against the sheet material, and the signal waveform from the piezoelectric element was used to plot the nth maximum value (corresponding to the signal generated at the time of the nth collision (n represents an integer number greater than 1), the results shown in FIG. 27 were obtained. Furthermore, the maximum values of signals by the nth collision and the (n+1)th collision are marked with a black circle and a triangle, respectively. It was found that the range of the nth maximum value varies depending on the type of sheet material, thus making it possible to determine the type of sheet material from the maximum value. This will be described specifically below.

Figure 29:
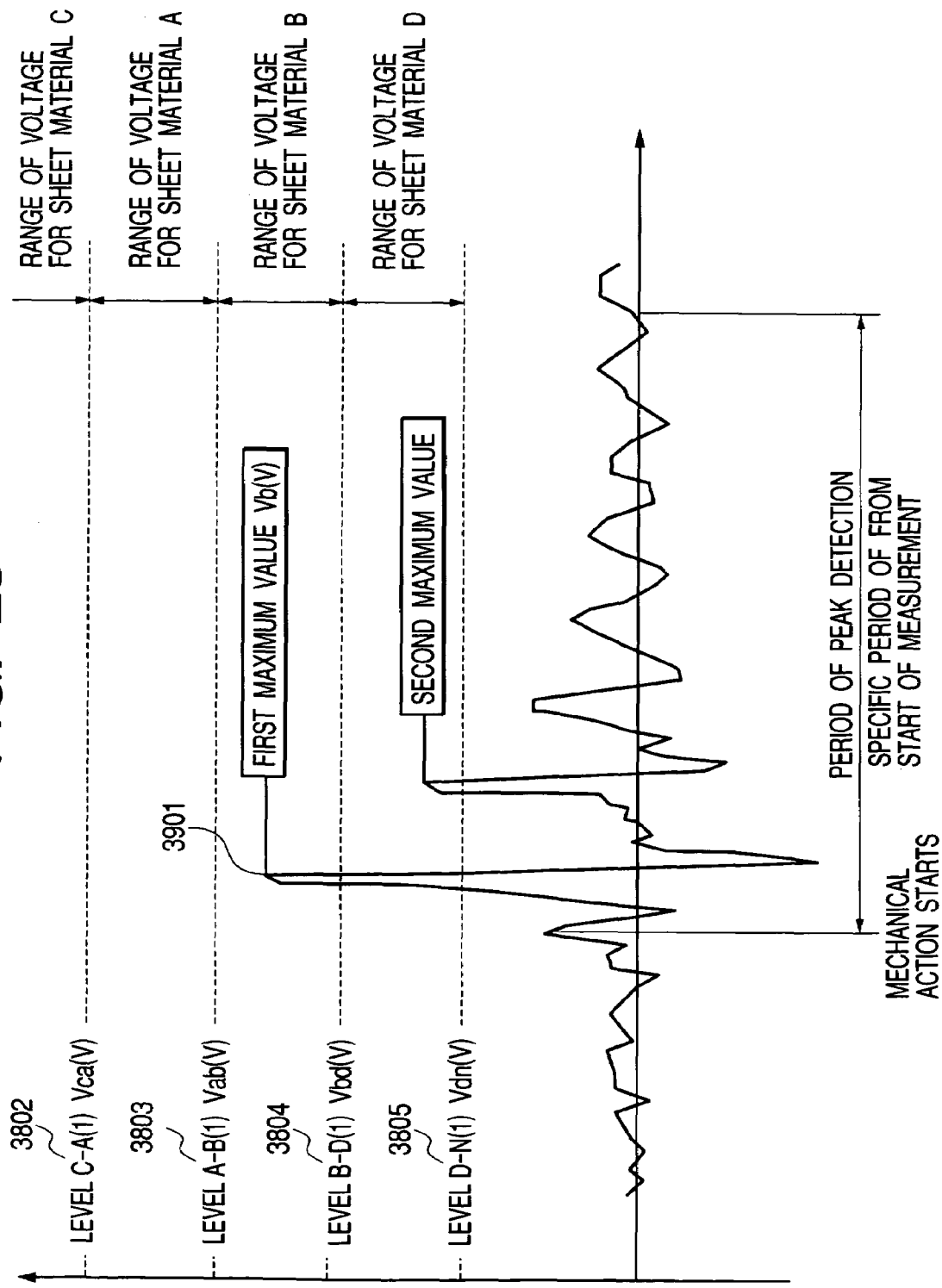
FIG. 29 shows an example of the output signal according to the present invention.
Figure 30:
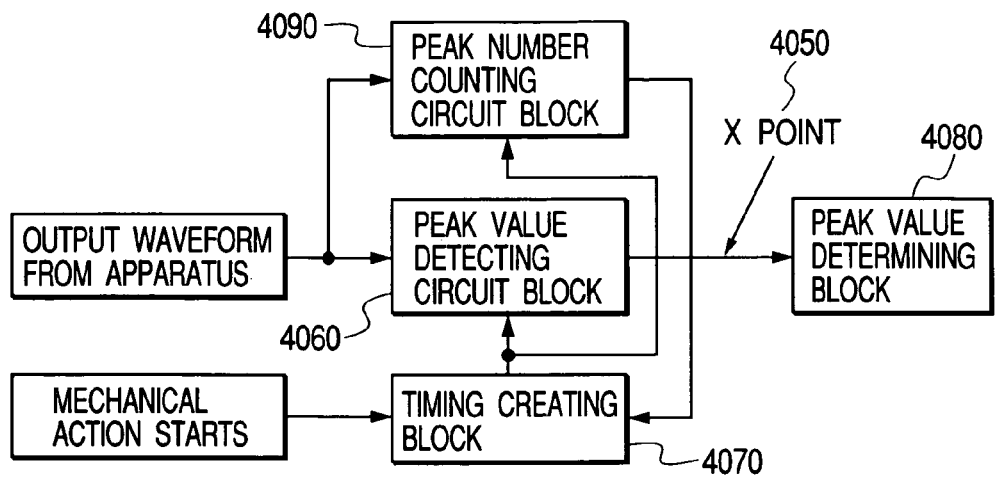
FIG. 30 shows the circuit configuration according to the present invention.

This will be described with reference to the example of output waveforms from the piezoelectric element of the sheet type detecting apparatus (FIGS. 28 and 29) and the example of the block of the circuit for determining the type of sheet from the first maximum value (FIG. 30). The impact was applied in the same way as Example 1 described above.

Figure 28:
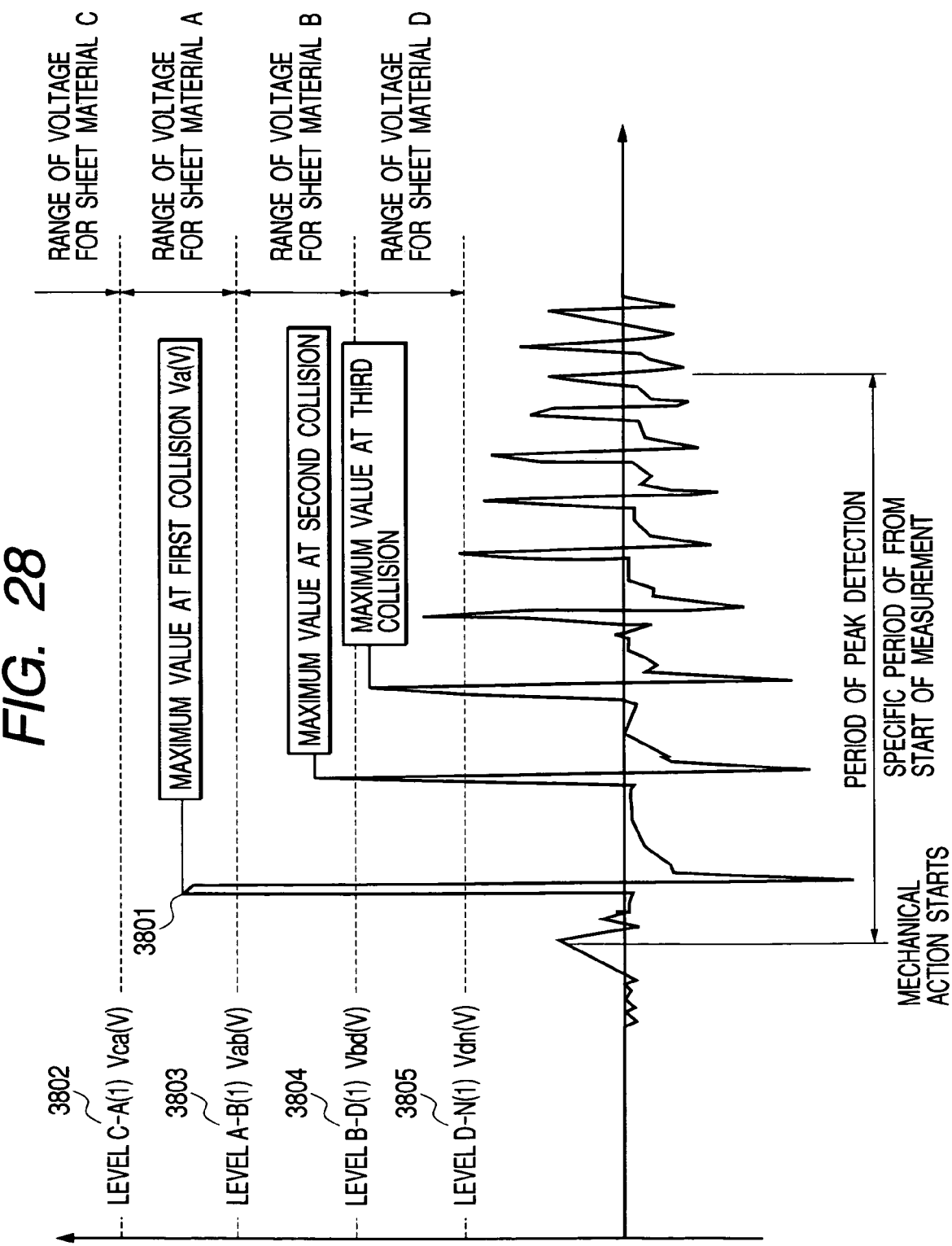
FIG. 28 shows an example of the output signal according to the present invention.

Signal waveforms of different first maximum values as shown in FIG. 28 (waveform of sheet material A) and FIG. 29 (waveform of sheet material B) are obtained from the piezoelectric element of the sheet type detecting apparatus due to the difference of sheet materials.

The output waveform from the signal output apparatus is inputted to a peak value detecting circuit block 4060 shown in FIG. 30 to obtain as a peak value the maximum value during the detection.

The value obtained by peak value detecting circuit block 4060 is inputted to a peak value determining block 4080 to determine the type of sheet material. In this figure, reference numeral 4090 denotes a peak number counting circuit block, and reference numeral 4070 denotes a timing creating block.

In the case of sheet material A, a waveform output A shown in FIG. 28 is obtained. Va3801 in the waveform represents the maximum value of the output signal at the time of the first collision. In the case of the sheet material B, a waveform output B shown in FIG. 29 is obtained. Vb3901 in the waveform represents the maximum value of the output signal at the time of the first collision.

In FIGS. 28 and 29, Vca3802, Vab3803, Vbd3804 and Vdn3805 represent threshold levels for determining the maximum value at the time of the first collision. Such threshold levels are stored in advance.

Which range of the threshold levels covers the maximum value obtained from the output signal waveform is determined by the comparator, whereby the type of sheet material can be determined.

When the impact is applied to a sheet material whose type is unknown, and the maximum value of the signal generated by the first collision is equal to or larger than the level of Vca3802, the sheet material is determined as sheet material C. It is determined as sheet material A when the maximum value equals to a level between Vca3802 and Vab3803, it is determined as sheet material B when the maximum value equals to a level between Vab3803 and Vbd3804, and it is determined as sheet material D when the maximum value equals to a level between Vbd3804 and Vdn3805.

Figure 31:
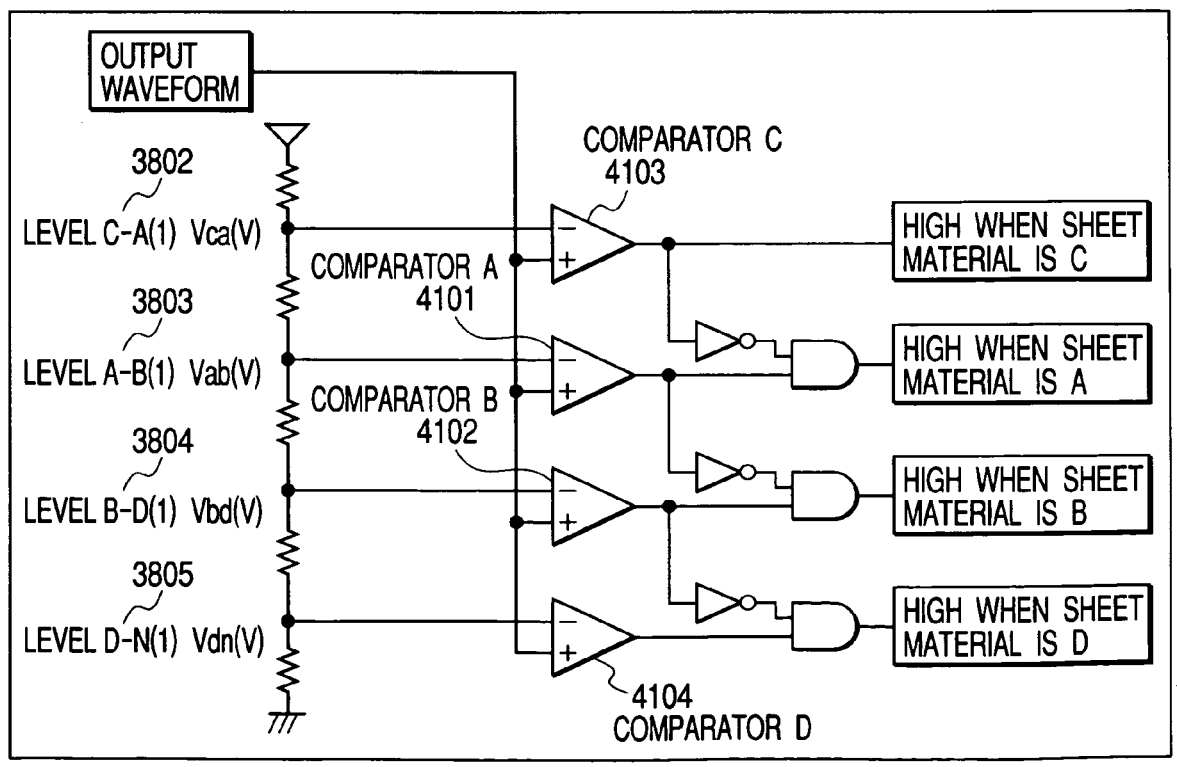
FIG. 31 shows the circuit configuration according to the present invention.

Therefore, in the case of the waveform output A shown in FIG. 28, the maximum value voltage equals the level of Va3801, and the output of the comparator A4101 in FIG. 31 is at High level, and thus the sheet material is determined as sheet material A in consideration of the condition of Vca3802>Va3801.

In the case of the waveform output B shown in FIG. 29, the maximum value voltage equals the level of Vb3801, and the output of the comparator B4102 is at High level, and thus the sheet material is determined as sheet material B in consideration of the condition of Vab3803>Vb3901.

Furthermore, for the peak value determining block shown in FIG. 31, the signal of Low is outputted from the comparator C, and the signals of High are outputted from the comparators A, B and D, when the sheet material is sheet material A.

Furthermore, for obtaining the nth maximum value, the number of peaks is counted by the peak number detecting block 4090, and operations of the peak value detecting circuit block 4060 are controlled by the timing creating block 4070 to detect the peak only during the period over which the nth maximum value is generated.

At this time, a threshold for the nth maximum value voltage according to the type of sheet material is defined.

Also, the maximum value obtained from the peak detection may be A/D-converted to determine the type of sheet material from the resulting digital value using a microcomputer.

Example 5

Ratio of Peak Values

The impact applying unit was collided against the sheet material, and the ratio between the signals from the piezoelectric element of the impact applying member generated in the nth collision and the (n+.alpha.)th collision (.alpha. represents an integer number greater than 1) (ratio between the nth maximum value and the (n+.alpha.)th maximum value (a represents an integer number greater than 1) was examined for each sheet material.

Figure 32:
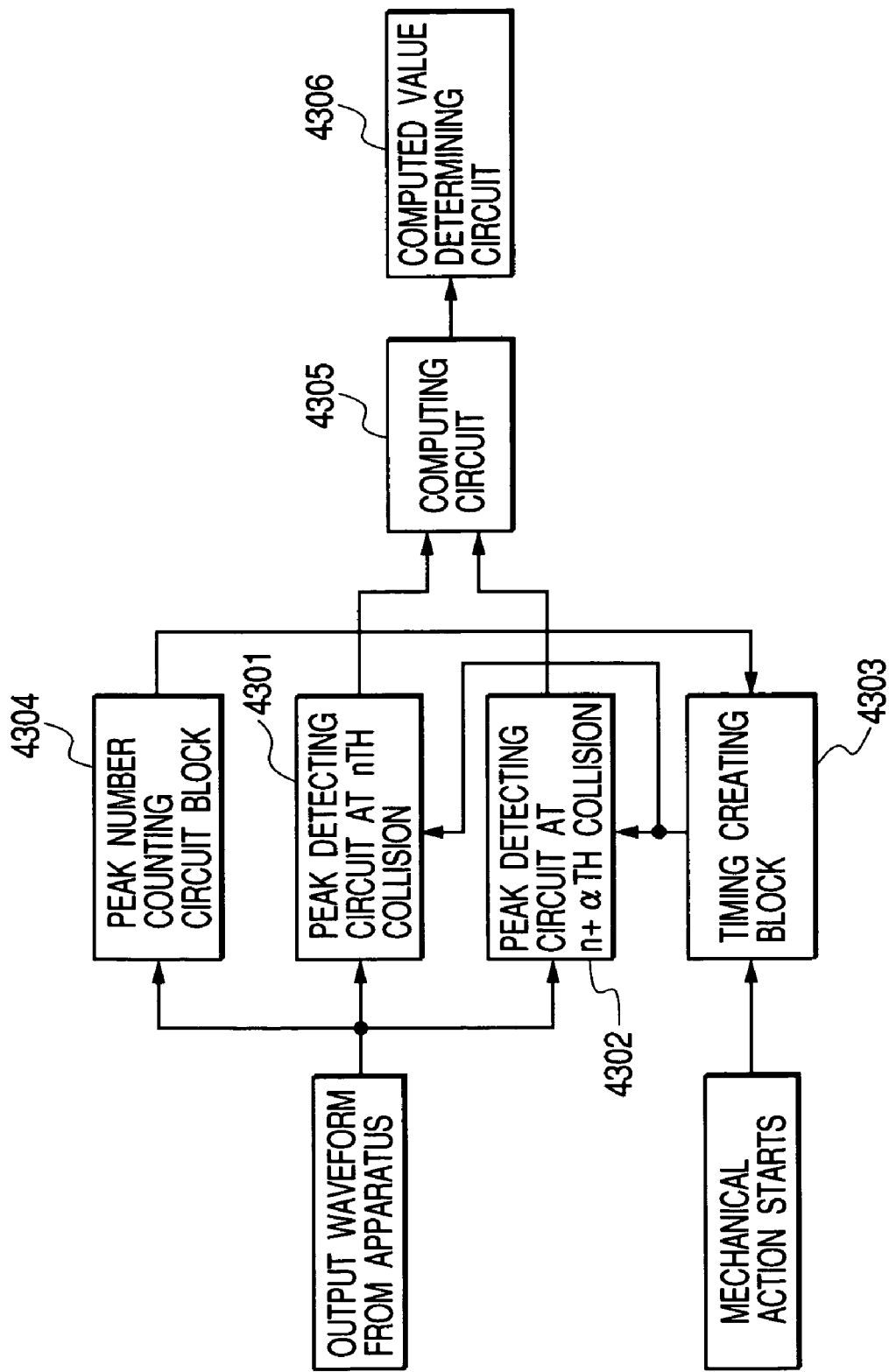
FIG. 32 shows the circuit configuration according to the present invention.

As a result, the distribution of values varied depending on the type of sheet material, and it was thus found that the type of sheet can be determined from the value. A method of determining the type of sheet material by using the ratio of peak values is shown in FIG. 32.

The output signal wavelength from the signal output apparatus is inputted to a peak detecting circuit 4301 and a peak detecting circuit 4302 operating in timing of nth collision and (n+.alpha.) th collision, respectively.

A timing creating circuit block 4303 uses the count obtained from a peak number counting circuit 4304 to create timing in which the peak detecting circuit is operated, and provides the timing to the peak detection circuit 4301 at the time of the nth collision and the peak detecting circuit 4302 at the time of the (n+.alpha.)th collision.

For the nth maximum value and the (n+.alpha.)th maximum value being the outputs of the peak detecting circuits 4301 and 4302, respectively, the ratio between the maximum values is calculated in a computing circuit block 4305, and the type of sheet material is determined from the value of the ratio in a computed value determining circuit 4306.

Also, the maximum value obtained from the peak detection may be A/D-converted to determine the type of sheet material from the resulting digital value using a microcomputer.

Example 6

Use of Two Types of Peak Values

Figure 33:
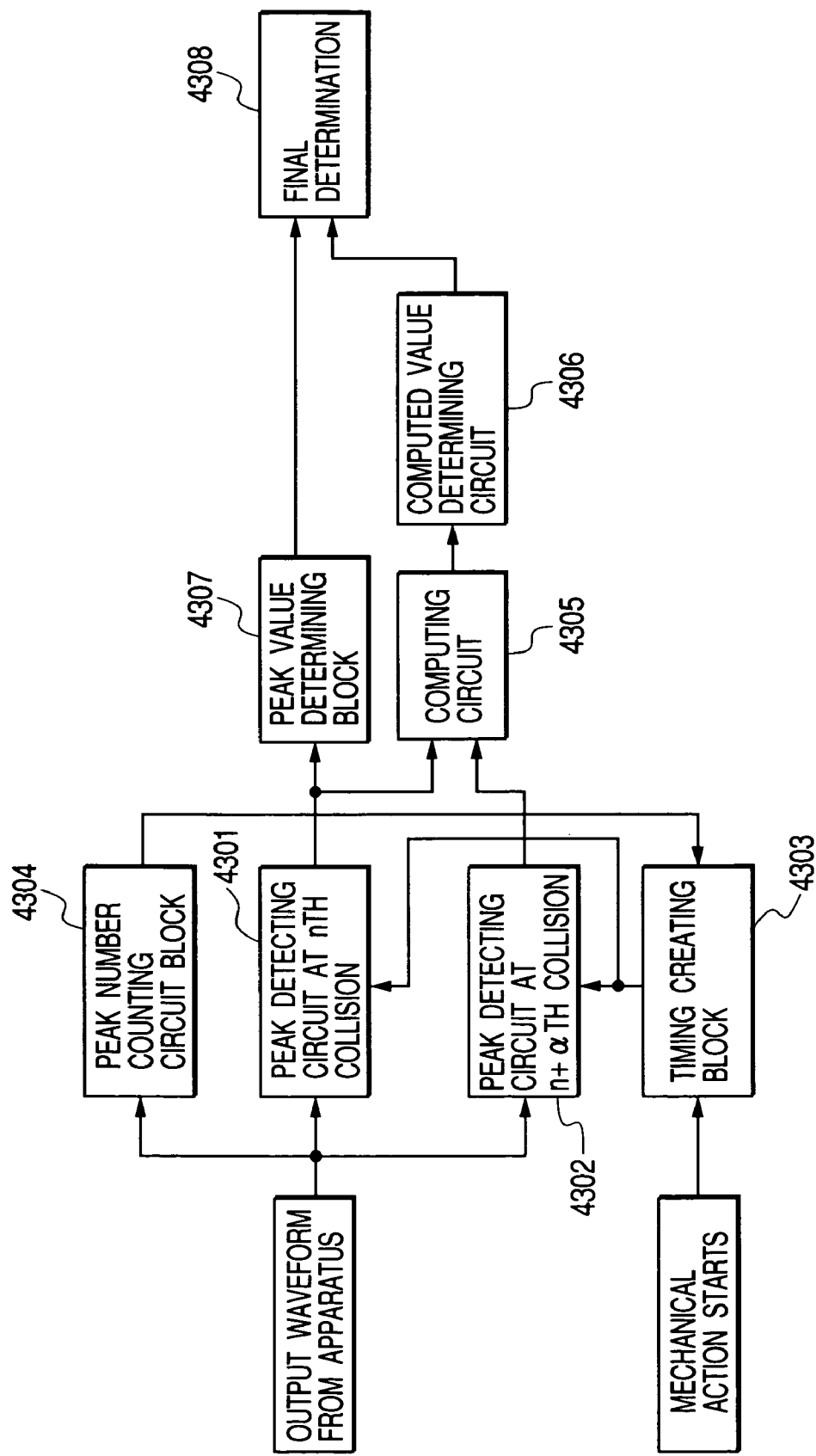
FIG. 33 shows the circuit configuration according to the present invention.

FIG. 33 is a block diagram in which the type of sheet material is determined using information by the signal generated in the nth collision (n represents an integer number greater than 1) (nth maximum value), and information by the amount of change of the signals generated in the nth collision and the (n+.alpha.)th collision (a represents an integer number greater than 1) (nth maximum value and (n+.alpha.)th maximum value).

The output signal wavelength from the signal output apparatus is inputted to a peak detecting circuit 4301 and a peak detecting circuit 4302 operating in timing of nth collision and (n+.alpha.)th collision, respectively.

The nth maximum value being the output is inputted to a peak value determining circuit 4307, and is simultaneously inputted to the computing circuit block 4305 together with the (n+.alpha.)th maximum value. The result of determination of the sheet material in the peak value determining circuit 4307 is inputted to a final determination block 4308.

Also, the result of determination using the value of ratio by the computing circuit block 4305 is inputted to the final determination block 4308, and a final determination is made in the block 4308 using the two determination results.

Also, the maximum value may be A/D-converted for digital processing by a microcomputer.

Example 7

Use of Average of nth Peak Values

Figure 34:
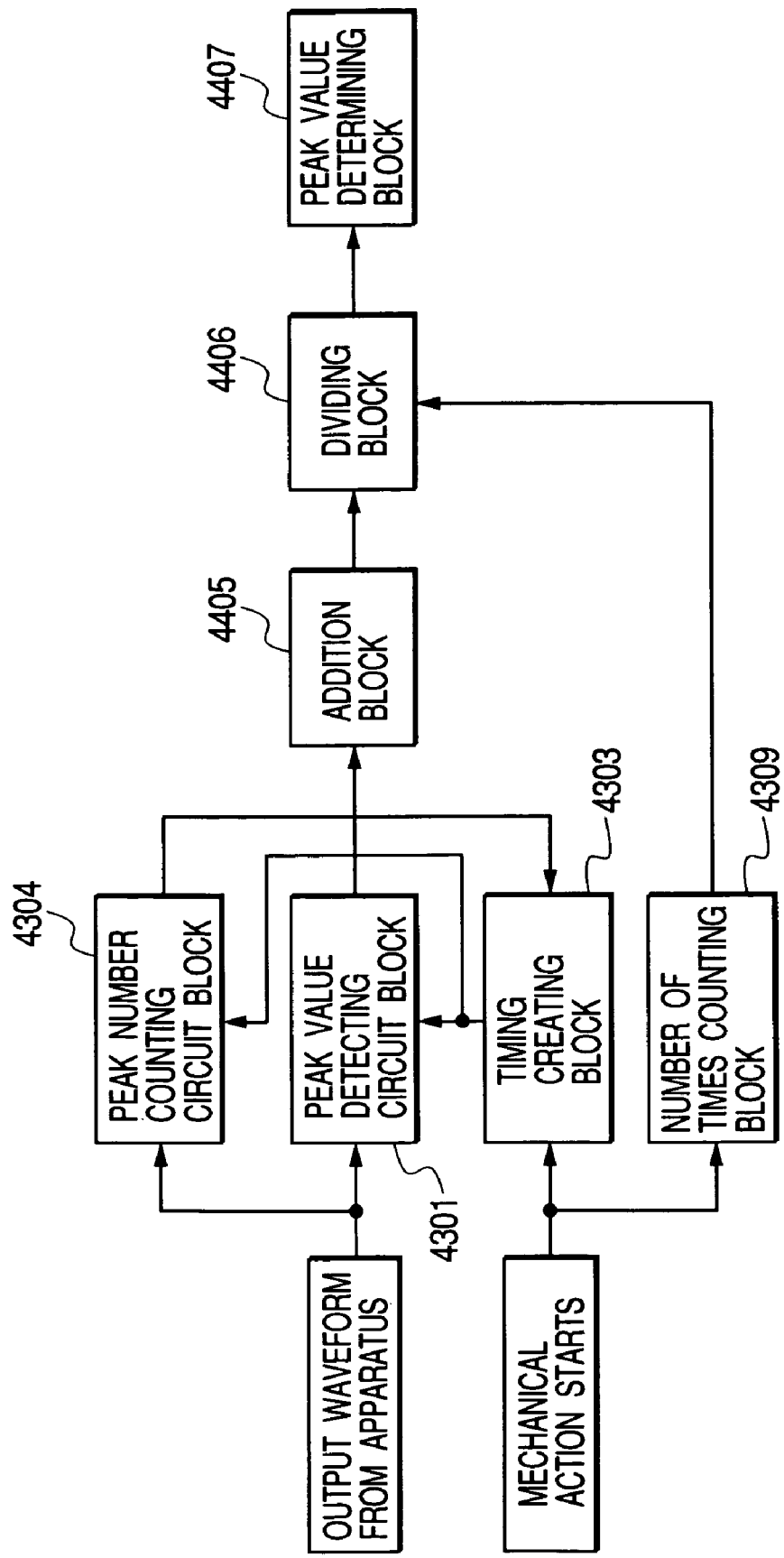
FIG. 34 shows the circuit configuration according to the present invention.

FIG. 34 shows an example in which the nth maximum value generated in the nth collision in Example 4 is measured over m times, and the measured values are averaged, followed by determining the type of sheet in the peak value determining block. The measurement is repeatedly conducted over predetermined m times, and the maximum value is added one after another by the number of measurements in an addition block 4405, and the resulting value is divided by the number of measurements m in a dividing block 4406, and the average value is determined in a peak value determining block 4407, whereby the type of sheet is determined. Numeral 4409 denotes number of times counting block.

Example 8

Detection by a Plurality of Circuits

Figure 35:
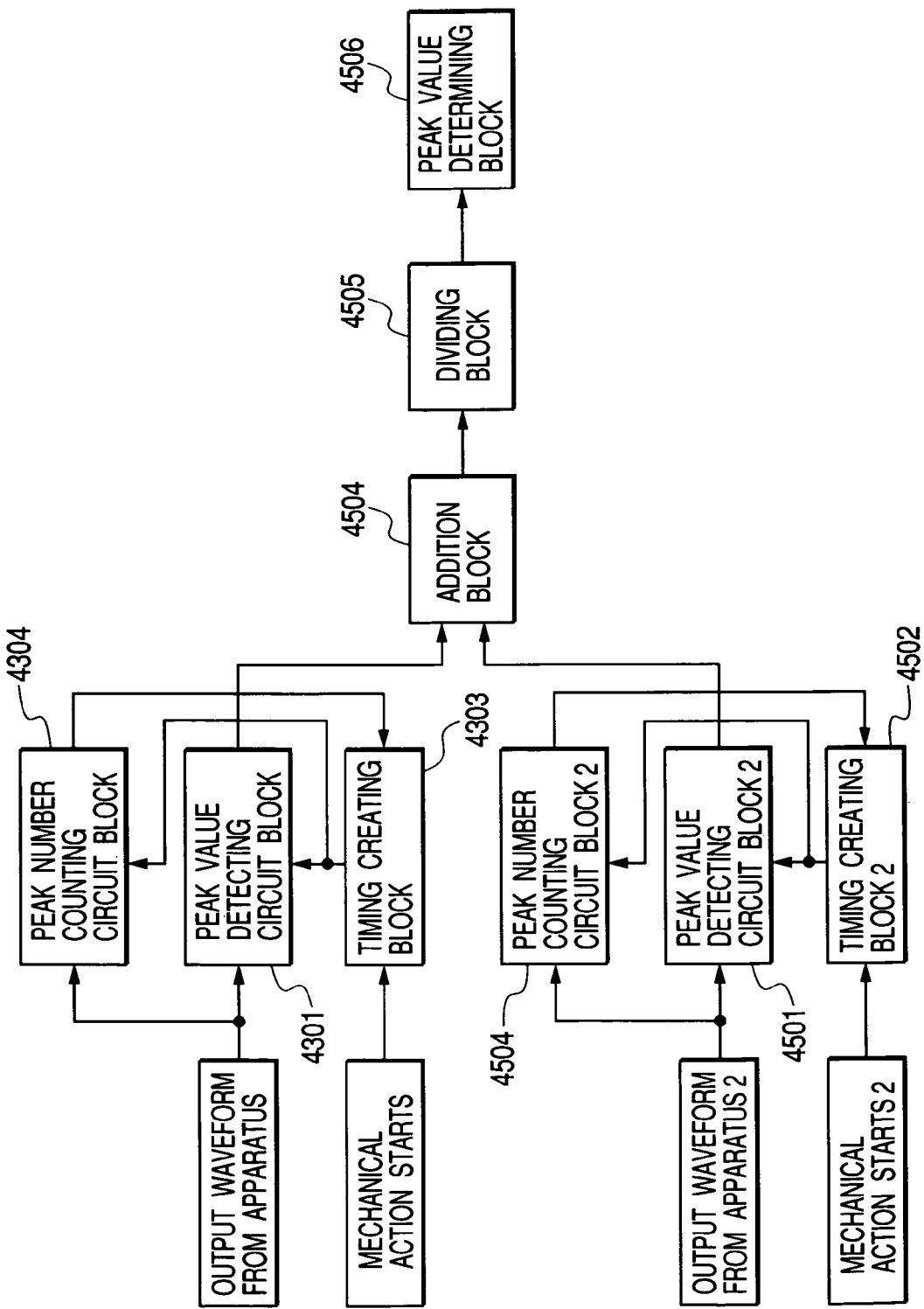
FIG. 35 shows the circuit configuration according to the present invention.

An example of using a circuit in which two signal output apparatuses are provided, and the nth maximum values are obtained from the outputs from the respective piezoelectric elements of the apparatuses is shown in FIG. 35. The maximum values obtained from the respective output signals are added together in an addition circuit block 4504, and the resulting value is averaged in a dividing circuit block 4505, and the type of sheet material is determined in a peak value determining circuit block 4506. Reference numerals 4504, 4501 and 4502 denote a peak number counting circuit block 2, a peak value detecting circuit block 2 and a timing creating block 2, respectively.

Example 9

Recoil Period

Figure 36:
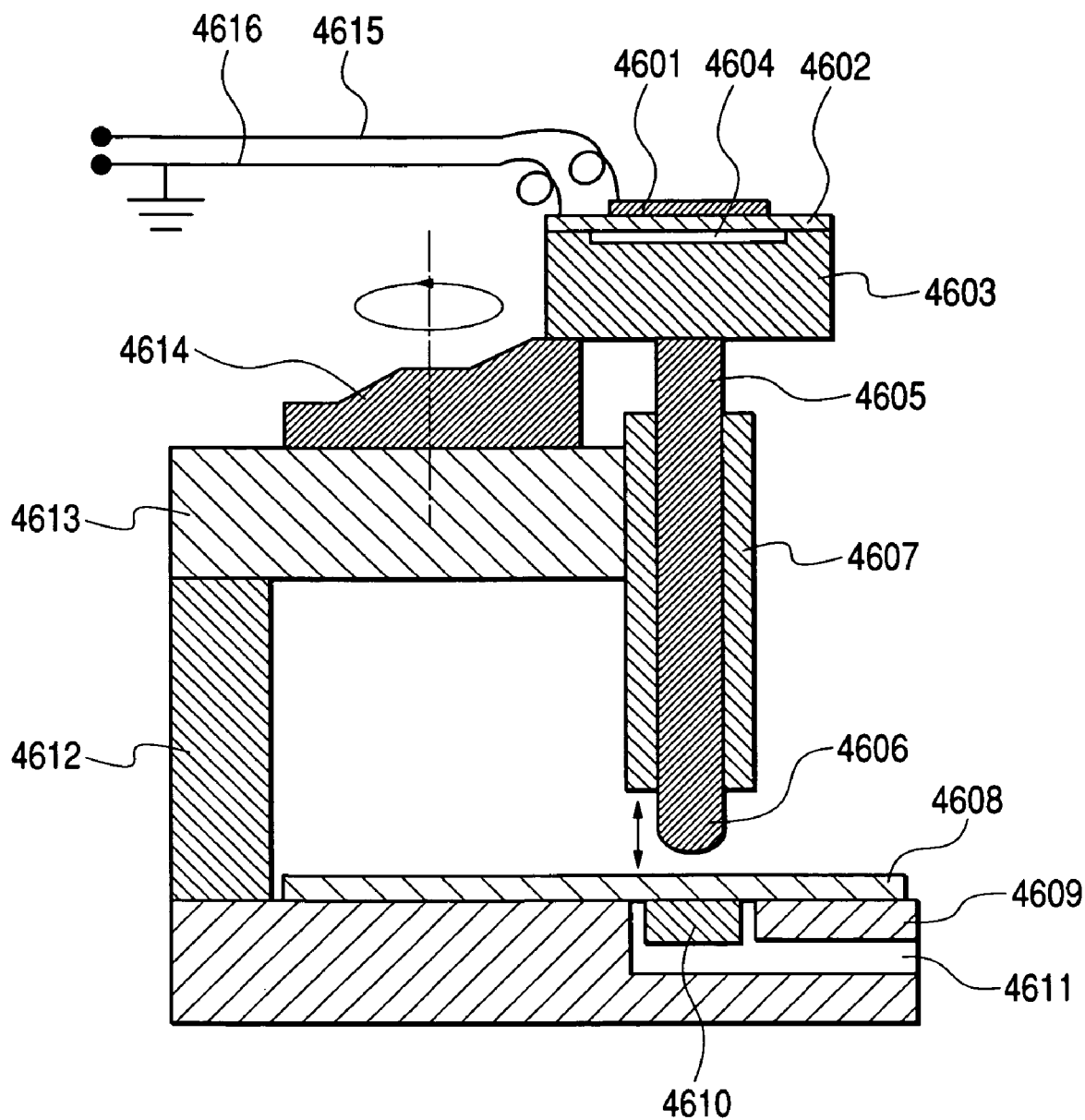
FIG. 36 illustrates the signal output apparatus according to the present invention.

FIG. 36 is a schematic sectional view of an impact applying unit that is suitably used in the present invention. Reference numeral 4601 is a piezoelectric body serving as a sensor, reference numeral 4602 denotes a flat spring with the piezoelectric body mounted thereon, reference numeral 4603 denotes a movable base portion for fixing the flat spring on a pedestal, reference numeral 4604 denotes a groove portion formed in the movable base portion 4603 for enabling deformation and displacement of the flat spring 4602, reference numeral 4605 denotes a movable axis portion connected to the movable base portion 4603, and reference numeral 4606 denotes an impact member having a hemispherical surface, which is connected to the front edge of the movable axis portion 4605.

Reference numeral 4607 denotes a bearing portion for promoting the uniaxial movement of the movable axis portion 4605, reference numeral 4608 denotes a sheet material as a printing paper, reference numeral 4609 denotes a platen for mounting the sheet material 4608, reference numeral 4610 denotes an impact receiving portion that is collided against the impact member 4606 with the sheet material 4608 therebetween, reference numeral 4611 denotes a vacuum port for bringing the sheet material 4608 into intimate contact with the platen 4609 and the impact member 4610 by means of reduced pressure, reference numeral 4612 denotes a frame, reference numeral 4613 denotes a frame, and reference numeral 4614 denotes a cam portion located above the frame 4613 for lifting the movable base portion 4603, and then allowing the movable base portion 4603 to fall. Reference numerals 4615 and 4616 are lead wires electrically connected to a positive electrode and a negative electrode of the piezoelectric body 4601, respectively.

Then, in the above configuration, the movable vase portion 4603 is first separated from the platen 4609 and moved upward until a certain height is reached by rotating the cam 4614, and in this state, the sheet material 4608 is placed on the platen 4609, followed by further rotating the cam portion 4614, whereby the movable base portion 4603 is fallen from the height to cause the impact member 4606 to collide against the sheet material 4608.

By the collision, the impact member 4606 recoils on the sheet material 4608 above the impact receiving portion 4610, and the flat spring 4602 undergoes a change in momentum by the impulse occurring at the time of collision to start vibrating from the static state, and due to the vibration, the piezoelectric body 601 mounted on the flat spring 4602 generates a piezoelectric current by rapid deformation, and thereafter the vibration is rapidly attenuated due to viscous resistance. As a trigger at the time of collision, the piezoelectric current is picked up as a voltage from the both ends of the lead wires 4615 and 4616.

In this Example, for increasing the viscous resistance, the flat spring 4602 united with the piezoelectric body 4601 is contained in an atmosphere of pressure gas (not shown), and flow resistance of the gas is generated by the vibration of the flat spring, whereby the vibration is attenuated.

The sheet type detecting apparatus was used to detect the type of sheet for the CF301 printing paper (manufactured by Canon Inc.) and the Recycle PPC printing paper (manufactured by Canon Inc.), wherein as shown in FIGS. 37A and 37B, a period of time between the trigger occurring at the time of the first collision and the trigger occurring at the time of the fifth collision was measured to compare the both types of sheets, and the experimental result was obtained showing that the time interval between the collisions for the CF301 printing paper was longer (200 [ms]), and on the other hand, the time interval between the collisions for the Recycle PPC printing paper was 165 [ms], which was shorter by 35 [ms]. That is, the duration of stay in air caused by the collision, namely the recoil period of the CF301 printing paper was longer than that of the Recycle PPC printing paper. It was thus found that the recoil period depends on the type of sheet.

Then, recoil periods corresponding to the above types of sheets were prepared in advance as a data table, and the above described experiment was carried out for each type of sheet, and as a result, it was possible to discriminate between the CF301 and the Recycle PPC adequately.

Example 10

Figures 38A, 38B:
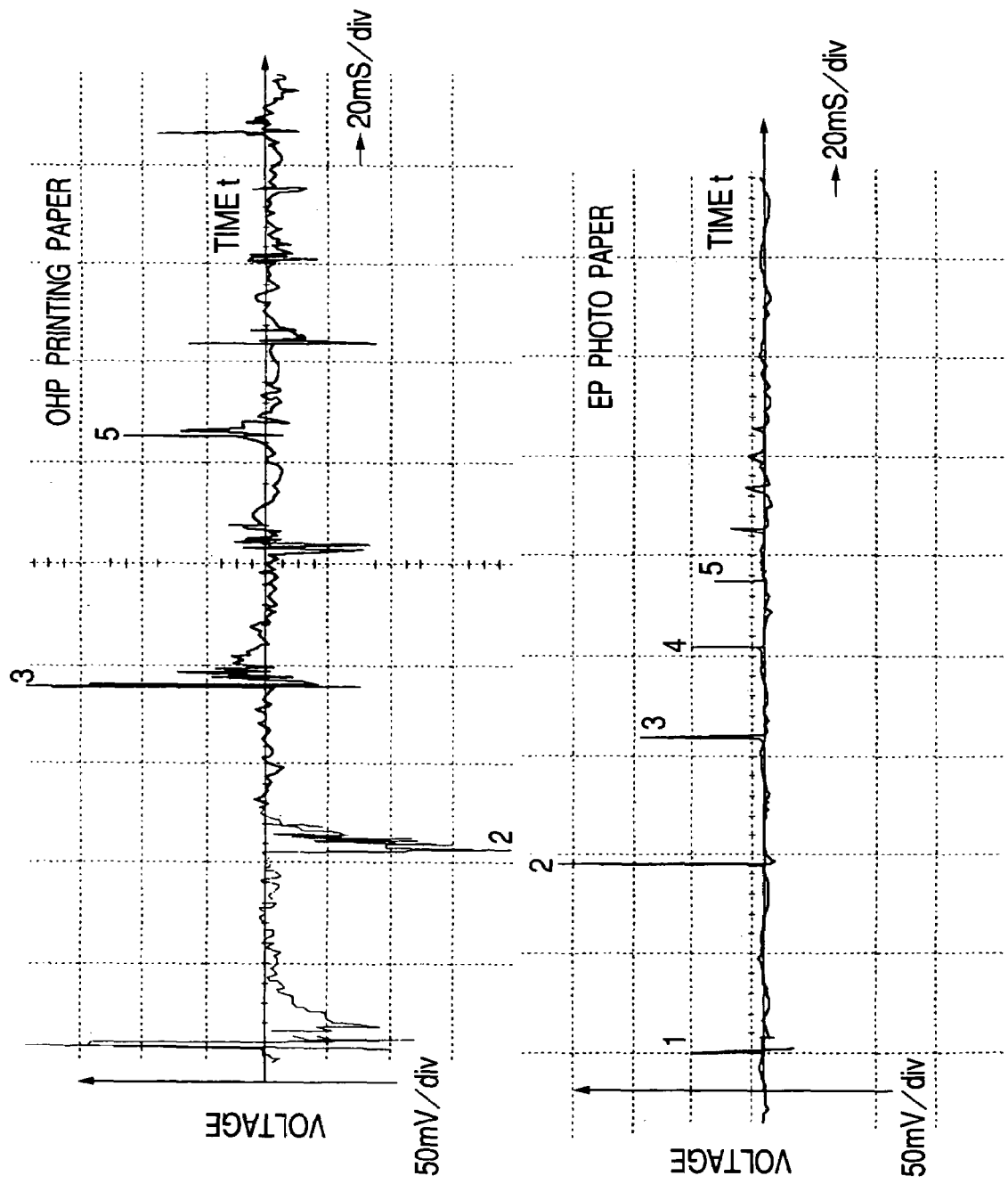
FIGS. 38A and 38B show examples of the output signal according to the present invention.

In addition, an apparatus similar to that described in Example 9 was used to measure a period of time required for five collisions for the following papers. As shown in FIGS. 38A and 38B, for detecting the type of sheet for the OHP printing paper (Kokuyo Co., Ltd.) and the EP photo printing paper (Canon Inc.), a comparison was made between the papers, and the experimental result was obtained showing that in the period of time between the trigger occurring at the time of the first collision and the trigger occurring at the time of the fifth collision, the time interval between the collisions for the OHP printing paper was longer by 26 [ms] (the value for the OHP was 118 [ms], and the value for the EP photo paper was 92 [ms]).

Then, in the same way as described above, the ratios of the square of the time interval between two sequential collisions of five collisions for the above types of sheets was compared to one another, and as a result, the difference in ratio between the types of sheet was clear, and the ratio was almost the same for the same type of sheet.

In this Example, the ratio for the OHP was 0.68, and the ratio for the EP photo paper was 0.50.

Furthermore, as described previously, the period of time can also be measured by generating a pulse using the trigger occurring for each collision, and counting the number of signal pluses obtained by the electric AND circuit of the pulse and a known external pulse.

Furthermore, the AND circuit is used in this Example, but the NAND circuit may also be used.

Brass is used for the impact receiving portion 4610 in this Example, but other substances of high Young's modulus and increased hardness may be used, and for example, iron, nickel, chrome, tungsten and molybdenum are preferable, or alloys or oxides thereof may be used, or aluminum oxide, silicon oxide, silicon nitride and zircon oxide may be used, or ceramics thereof may be used, or glass or polymeric materials may be used.

In this Example, the viscous resistance of the flat spring vibration system is increased to generate only the trigger signal at the time of the collision, and in order to attenuate natural vibration of the flat spring, the flat spring united with the piezoelectric body is contained in an atmosphere of pressure gas to enrich viscous resistance components with the flow of the gas occurring at the time when the flat spring vibrates, but instead thereof, for example, a bladed body for increasing air resistance may be used for the flat spring vibration system.

Furthermore, in the present invention, nitrogen gas is used as the gas, but instead thereof, for example, an inert gas such as argon gas may be used.

Figure 39:
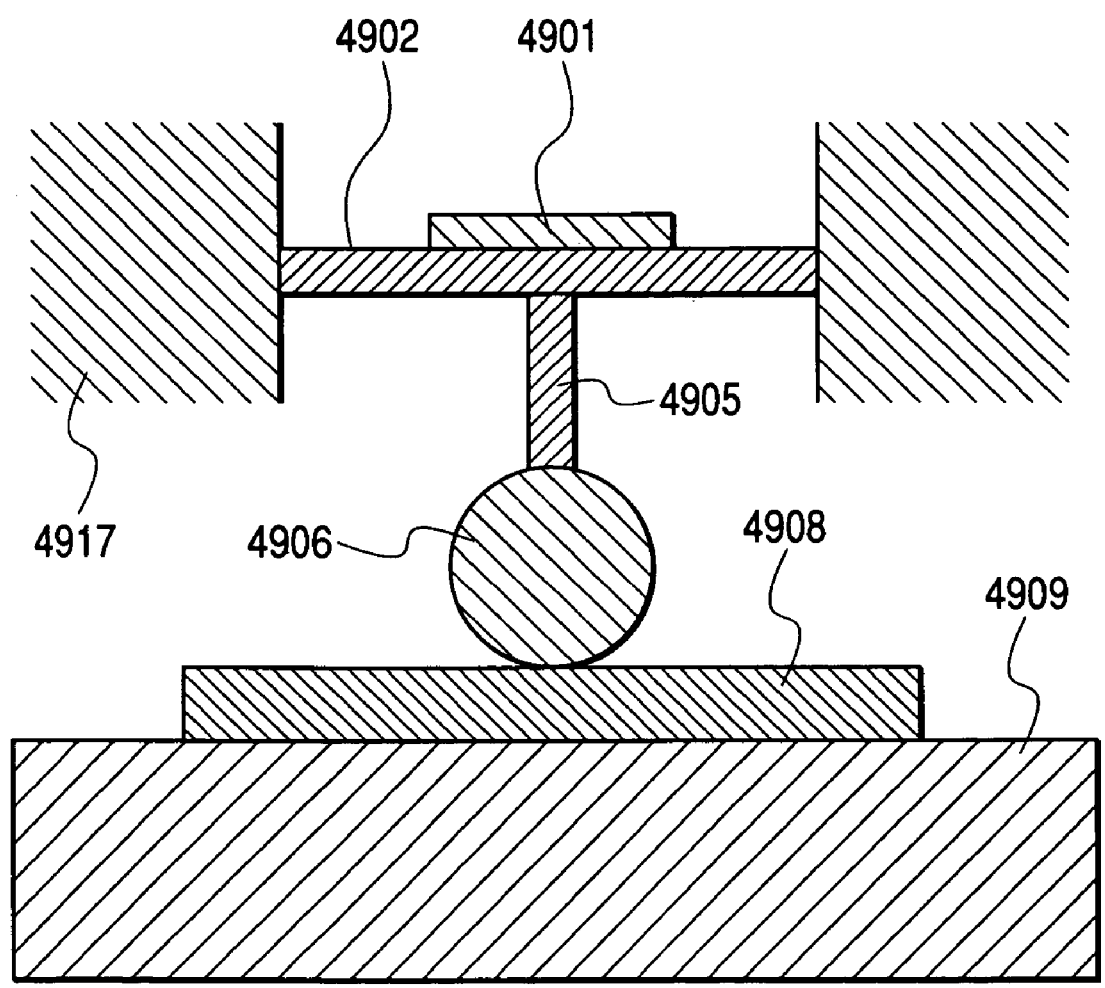
FIG. 39 illustrates the signal output apparatus according to the present invention.
Figure 40:
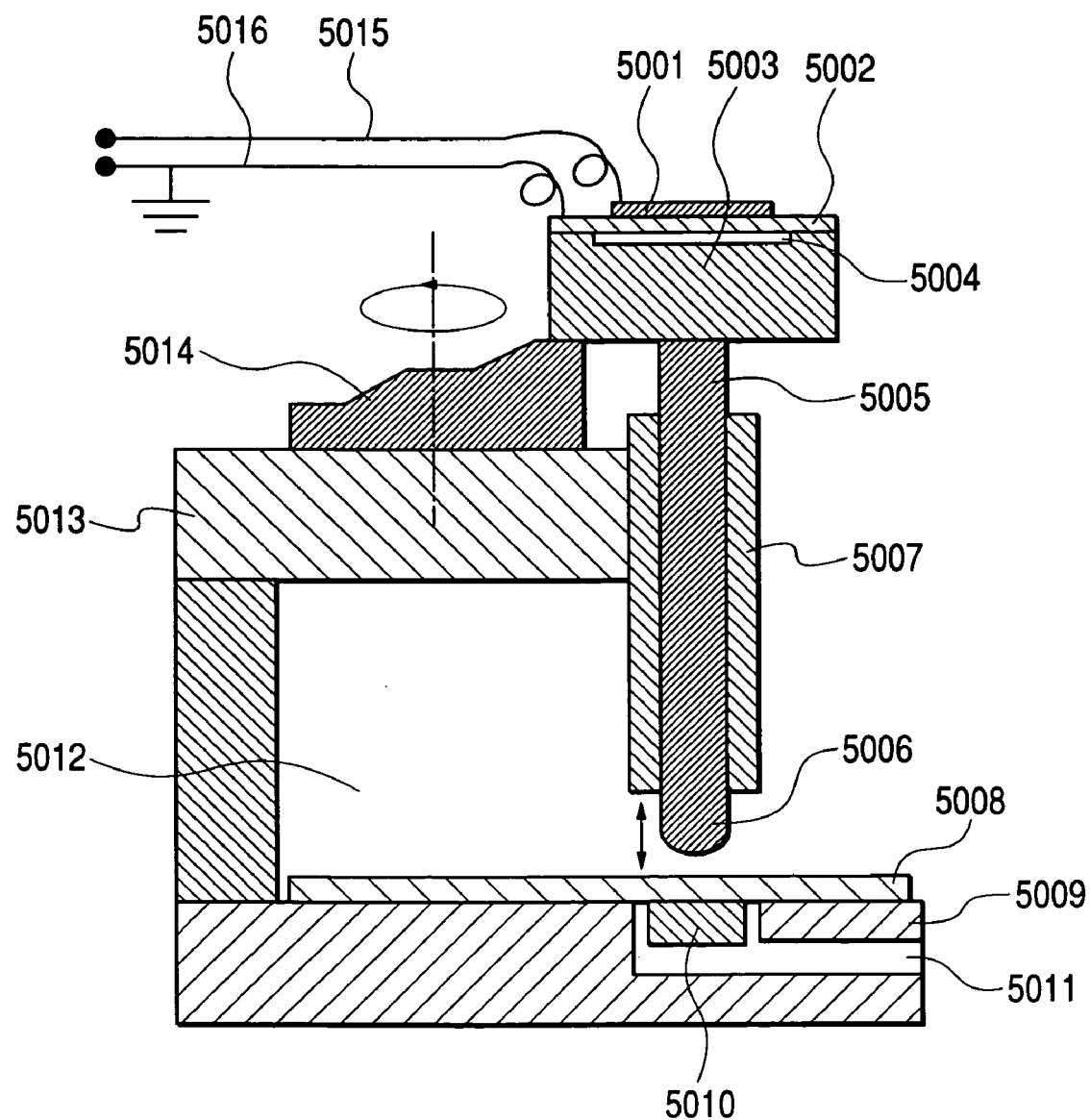
FIG. 40 illustrates the signal output apparatus according to the present invention.

In addition, in the present invention, gravity is used as means for having the impact member collided against the sheet material, but instead thereof, for example, the method may be used in which a flat spring 4902 is fixed to a fixed end 4917, and the flat spring 4902 is lifted by a cam mechanism (not shown), whereby deformation energy is accumulated in the flat spring 4902, and thereafter the flat spring 4902 is detached from the cam to have the impact portion 4906 collided against the sheet material 4908 by means of the accumulated energy of the flat spring 4902 detached from the cam, as shown in FIG. 39.

Furthermore, the flat spring 4902 may be a coil spring. If the spring is used, the impact member 4906 can be collided against the back surface of the sheet material 4908 opposing to gravity, thus making it possible to detect the type of sheet at the back surface of the sheet material 4908.

Example 11

An example using FIGS. 40, 41A and 41B, 42 and 43 will be described.

Reference numeral 5001 is a piezoelectric body serving as a sensor, reference numeral 5002 denotes a flat spring with the piezoelectric body mounted thereon, reference numeral 5003 denotes a movable base portion for fixing the flat spring 5002 on a pedestal, reference numeral 5004 denotes a groove portion formed in the movable base portion 5003 for enabling deformation and displacement of the flat spring 5002, reference numeral 5005 denotes a movable axis portion connected to the movable base portion 5003, and reference numeral 5006 denotes an impact member having a hemispherical surface, which is connected to the front edge of the movable axis portion 5005, and therefore the movable base portion 5003, the movable axis portion 5005 and the impact member 5006 constitute one united body, and reference numeral 5007 denotes a bearing portion for promoting the uniaxial movement of the movable axis portion 5005, reference numeral 5008 denotes a sheet material as a printing paper, reference numeral 5009 denotes a platen for mounting the sheet material 5008, reference numeral 5010 denotes an impact receiving portion that is collided against the impact member 5006 with the sheet material 5008 therebetween, reference numeral 5011 denotes a vacuum port for bringing the sheet material 5008 into intimate contact with the platen 5009 and the impact member 5010 by means of reduced pressure, reference numeral 5012 denotes a frame, reference numeral 5013 denotes a frame, and reference numeral 5014 denotes a cam located above the frame 5013 for lifting the movable base portion 5003, and then allowing the movable base portion 5003 to fall. Reference numerals 5015 and 5016 are lead wires electrically connected to a positive electrode and a negative electrode of the piezoelectric body 5001, respectively. Furthermore, a sealing member is actually provided (not shown) so that the vibration of the flat spring created by the impact is not rapidly attenuated while the natural vibration is developed in the flat spring.

Then, in the above configuration, the movable vase portion 5003 is first separated from the platen 5009 and moved upward until a certain height is reached by rotating the cam 5014, and in this state, the sheet material 5008 is placed on the platen 5009, followed by further rotating the cam portion 5014, whereby the movable base portion 5003 is fallen from the drop height to cause the impact member 5006 to collide against the sheet material 5008. By the collision, the impact member 5006 recoils on the sheet material 5008 above the impact receiving portion 5010, and the flat spring 5002 undergoes a change in momentum by the impulse occurring at the time of collision to start vibrating from the static state, namely start a natural vibration, and tensile strains and compressive strains occur alternatingly on the surface of the flat spring due to the natural vibration.

Tensile strains and compressive strains also occur in the piezoelectric body placed on the surface of the flat spring 5002, thus making it possible to detect an alternating voltage equivalent to the natural vibration of the flat spring 5002 from the lead wires 5015 and 5016 electrically connected to the both poles of the piezoelectric body.

Furthermore, in the present invention, the electric signal equivalent to the natural vibration of the flat spring 5002 is picked up from the piezoelectric body 5001 as a voltage, but it may be picked up as a piezoelectric current, namely as a current.

In this Example, the flat spring 5002 and the piezoelectric body 5001 are contained in an atmosphere of reduced pressure with the air replaced with argon gas (not shown) to curb attenuation of the natural vibration of the flat spring. Preferably, the atmosphere of reduced pressure is adjusted so that the attenuation of the amplitude of the natural vibration started after the collision is minimized, and the electric signal from the piezoelectric body is attenuated to a level equal to or lower than the set voltage of the comparator by the time when the next collision occurs.

Figure 42:
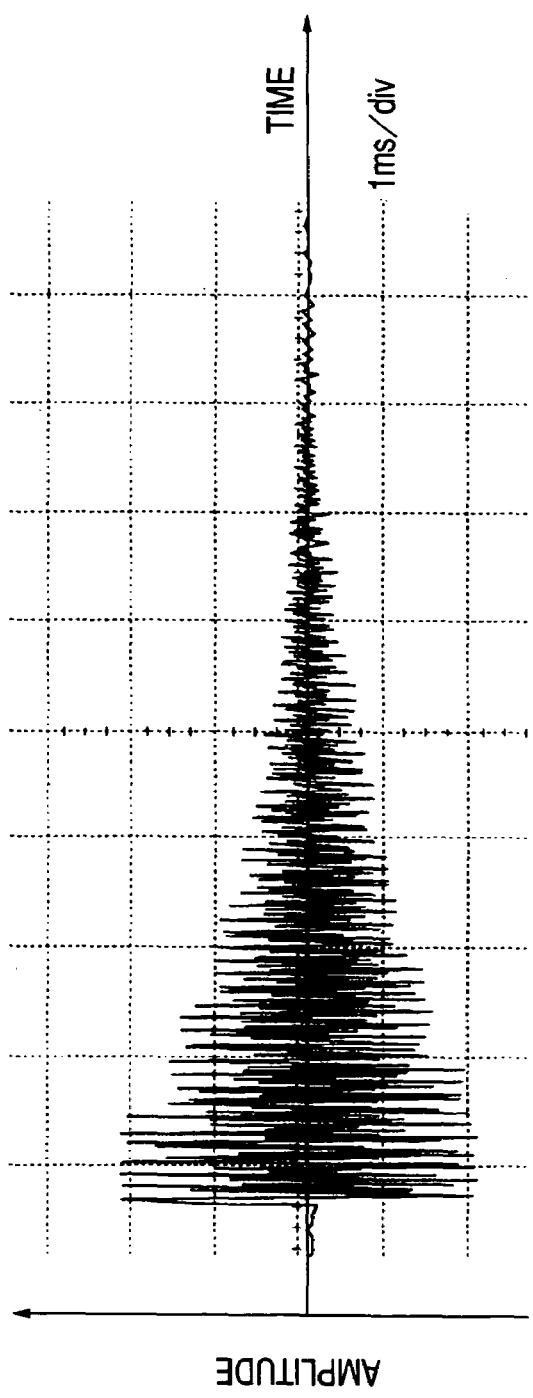
FIG. 42 shows an example of the output signal according to the present invention.

The impact member 5006 was fallen from the drop height and collided against the impact receiving portion 5010 using a sheet type detector, and an attenuation curve of natural vibration of the flat spring 5002 as shown in FIG. 42 was obtained.

Figure 43:
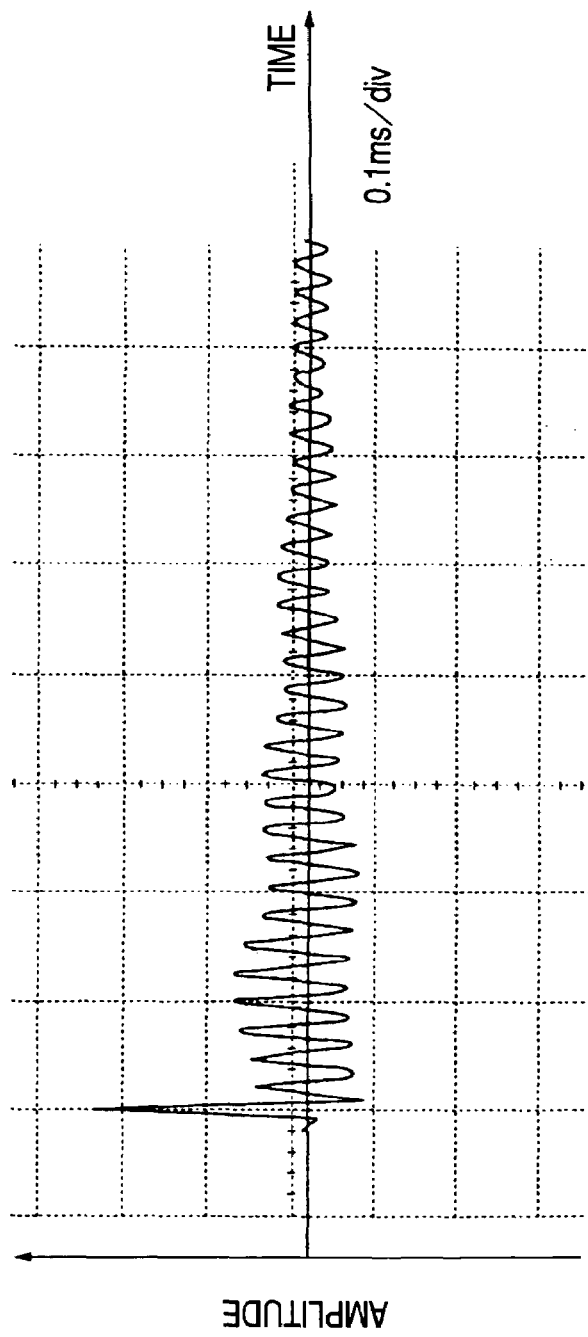
FIG. 43 shows an example of the output signal according to the present invention.

The time axis was further reduced, and an attenuated vibration curve shown in FIG. 43 was obtained, and the frequency of natural vibration calculated from this figure was 7.7 kHz, which was slightly small compared to the theoretical value of 8.1 kHz, but was generally an appropriate frequency of natural vibration.

Figure 41A:
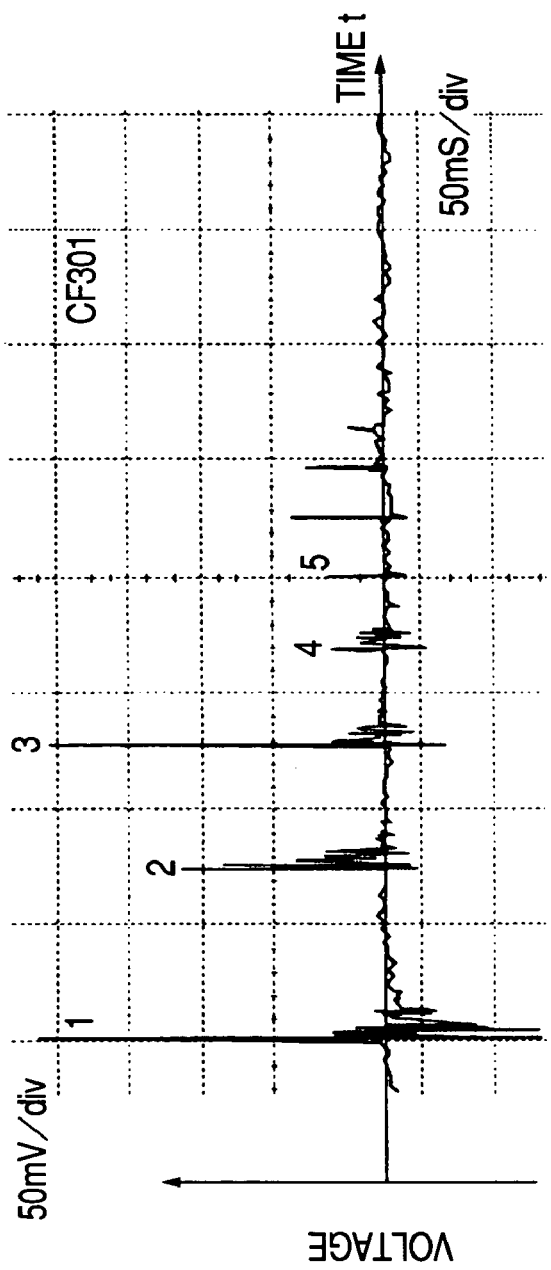
FIGS. 41A and 41B show examples of the output signal according to the present invention.
Figure 41B:
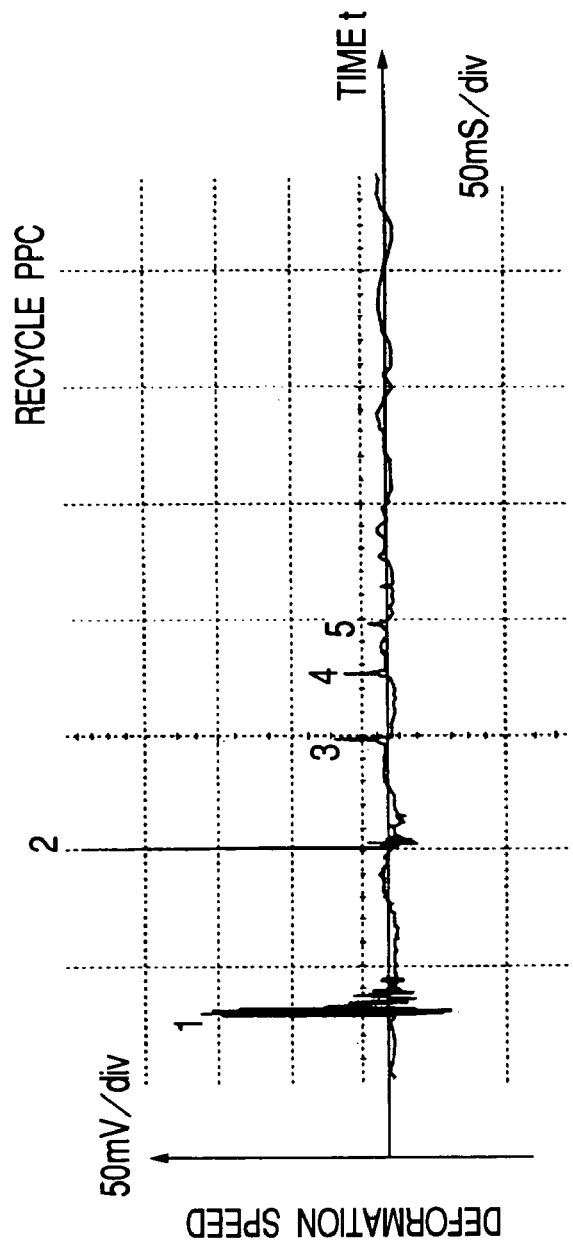

The sheet type detecting apparatus was used to detect the type of sheet for the CF301 printing paper (manufactured by Canon Inc.) and the Recycle PPC printing paper (manufactured by Canon Inc.), wherein as shown in FIGS. 41A and 41B, the voltage signal equivalent to the frequency of natural vibration of the flat spring from the piezoelectric body during the time period of 0.25 seconds after the first collision was inputted to the comparator, and the voltage signal larger than a comparative voltage defined arbitrarily (0.05 V in the case of this Example) was pulsed, and the number of pulses was counted by a counter, and as a result, the counted number of pulses of CF301 was larger than that of Recycle PPC by 150 pluses. That is, the experimental result of examining the counted number of pulses showed that the recoil period for the CF301 paper is greater than that for the Recycle PPC paper. In other words, it was found that the recoil period depends on the type of sheet.

Example 12

Figure 44:
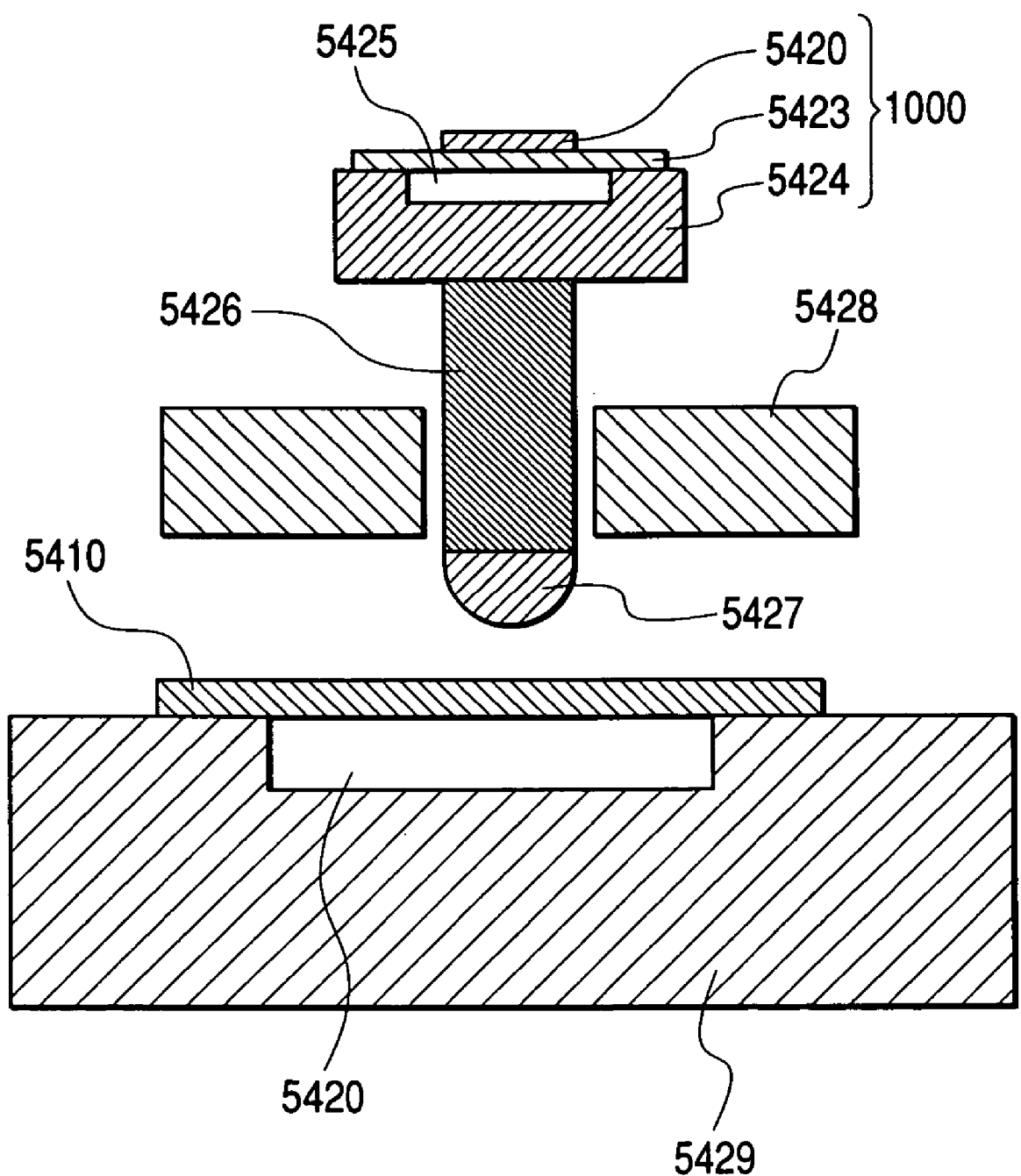
FIG. 44 illustrates the signal output apparatus according to the present invention.

This Example will be described with reference to FIGS. 44, 45 and 46. Reference numeral 5420 is a piezoelectric body serving as a sensor, reference numeral 5423 denotes a flat spring with the piezoelectric body 5420 mounted thereon, reference numeral 5424 denotes a movable base portion for fixing the flat spring on a pedestal, reference numeral 5425 denotes a groove portion formed in the movable base portion 5424 for enabling deformation and displacement of the flat spring, reference numeral 5426 denotes a movable axis portion connected to the movable base portion 5424, and reference numeral 5427 denotes an impact portion having a hemispherical surface, which is connected to the front edge of the movable axis portion 5426.

The spring 5423, the movable base portion 5424, the movable axis portion 5426 and the impact portion 5427 constitute one united recoil body, and reference numeral 5428 denotes a bearing portion for promoting the uniaxial movement of the movable axis portion 5426, reference numeral 5410 is a sheet material as a printing paper, and reference numeral 5429 denotes a platen for mounting the sheet material. Reference numeral 5420 denotes a groove provided in the platen 5429, reference numeral 5411 denotes a hole provided in the bottom of the platen 5429, reference numeral 5412 denotes a cavity portion provided in the platen 5429, reference numeral 5413 denotes a absorber placed in the groove 5420, reference numeral 5415 denotes an input spring for supplying energy for causing the impact portion 5427 to collide against the sheet material 5410, reference numeral 16 denotes a spring fitting portion connected to the platen 5429.

Then, in the above configuration, when the recoil body is fallen from an altitude of H0 (not shown), the impact portion 5427 is collided against the sheet material 5410 on the platen 5429 after a period of time T0, and due to the deformation associated with the deformation (plastic deformation and elastic deformation) of the sheet material caused by the collision, and the vibration of the platen 5429 occurring by the collision of the impact portion 5427 against the platen 5429 with the sheet material 5410 therebetween, the original input energy (potential energy at the time of falling in this case) is attenuated, and after the collision, the recoil body rises into space due to residual energy.

Then, the recoil body falls again, and in the process of repeating operations similar to those described above, the piezoelectric current generated in the piezoelectric body by the rapid strain deformation of the piezoelectric body 5420 mounted on the flat spring 5423 caused by the impulse occurring at the time of the collision is detected at the time interval at which the impact portion 5427 collides against the sheet material 5410, whereby the type of sheet is detected.

In the Example, by providing the grove 5420 in the platen 5429, the type of sheet material 5410 can be effectively detected because the vibration created in the platen 5429 at the time of collision, namely the absorption of energy by the vibration depends on the rigidity of the sheet material 5410.

Here, the absorption of energy by the absorber 5413 varies depending on the type of the sheet material 5410, and the absorption of energy decreases as the rigidity of the sheet material increases, and the adsorption of energy increases as the rigidity decreased.

Figure 47A:
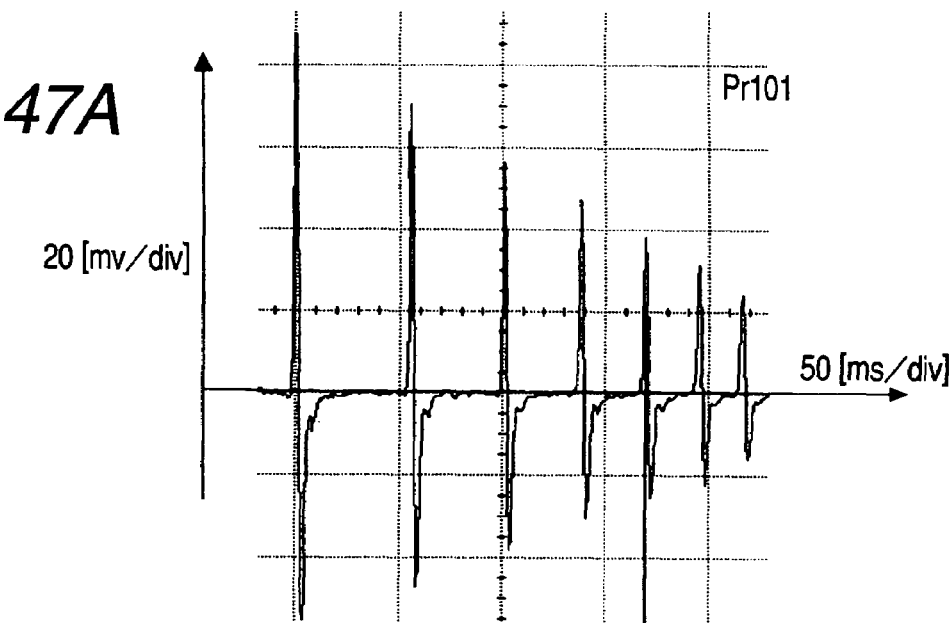
FIGS. 47A and 47B show examples of the output signal according to the present invention.
Figure 47B:
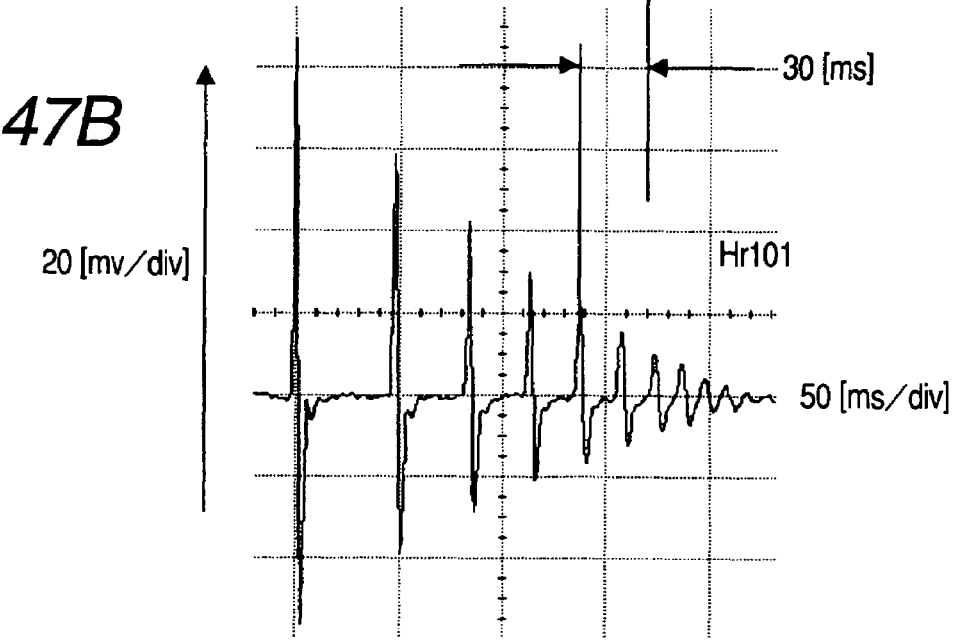

In this Embodiment, when the type of sheet was detected for the Pr 101 printing paper (manufactured by Canon Inc.) and the Hr101 printing paper (manufactured by Canon Inc.), there was a difference of 30 [ms] between these two papers in time interval between the first recoil and the fifth recoil as shown in FIGS. 47A and 47B, and thus the type could be clearly determined.

Figure 45:
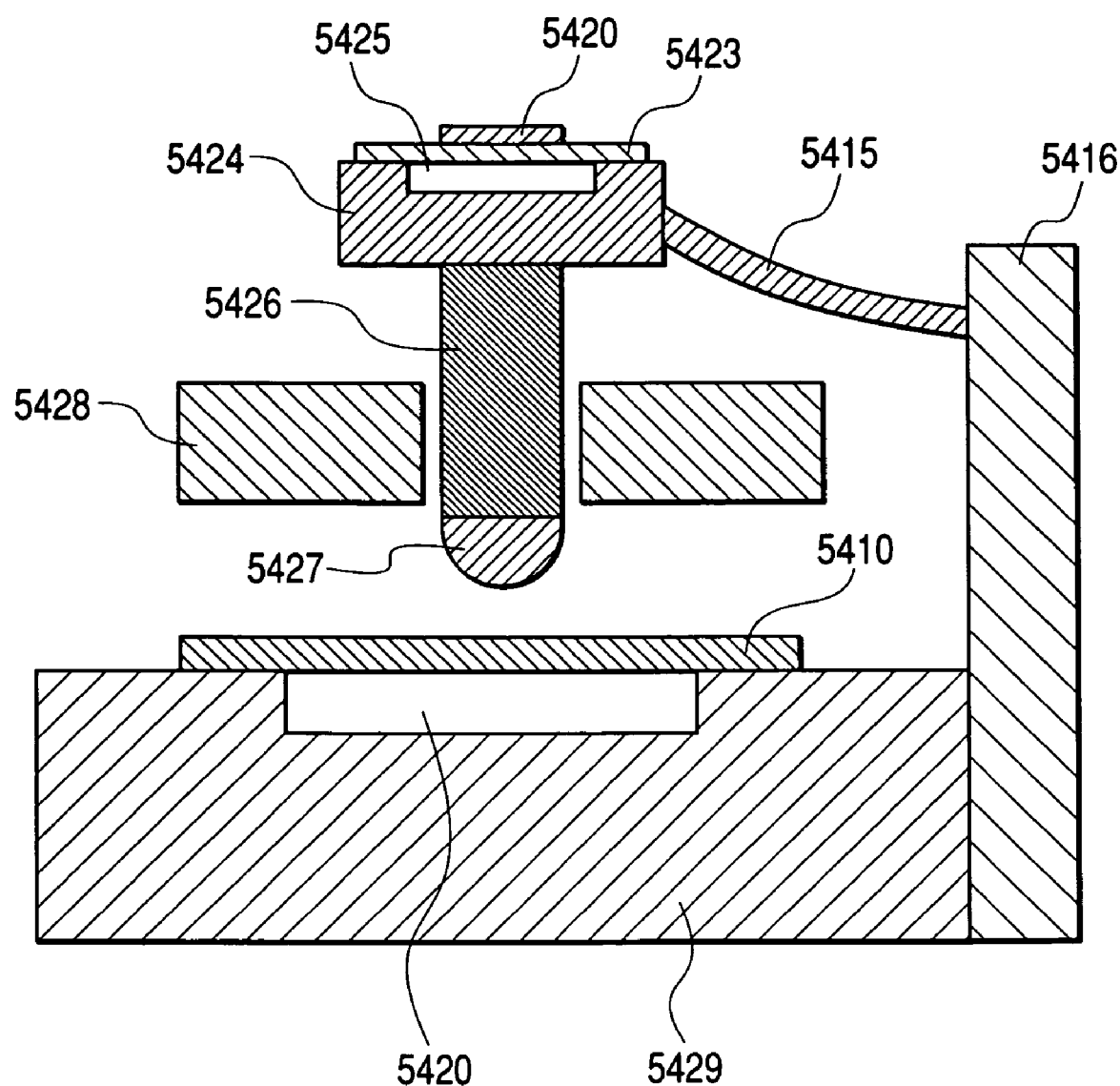
FIG. 45 illustrates the signal output apparatus according to the present invention.

The recoil body is fallen by means of gravity in this Example, but the recoil body may be collided against the sheet material 5410 by means of input energy of the flat spring 5415 shown in FIG. 45.

Figure 46:
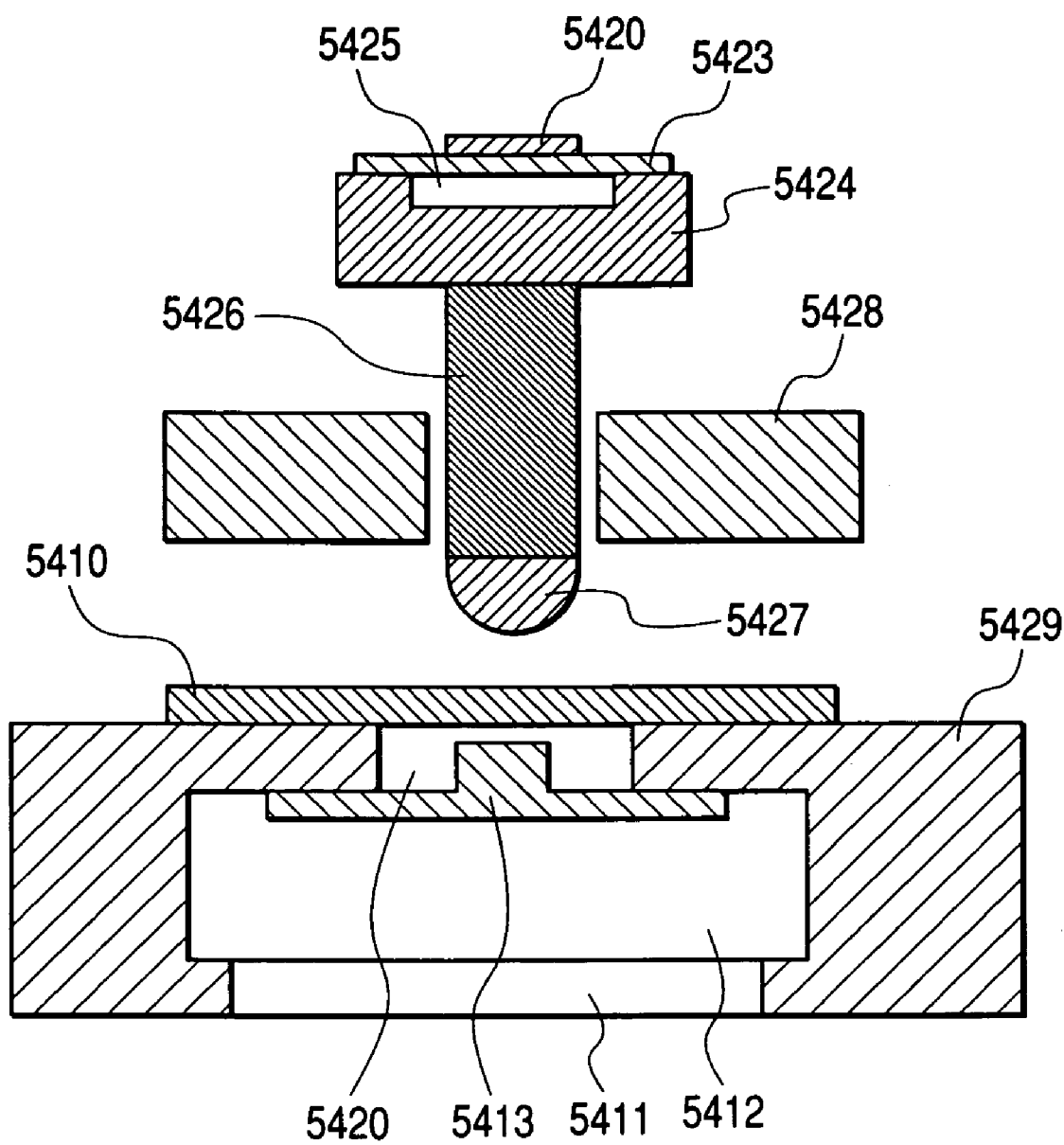
FIG. 46 illustrates the signal output apparatus according to the present invention.

In addition, even if as shown in FIG. 46, the absorber 5413 is provided in the grove portion 5420 of the platen, and the recoil body is collided against the absorber as another aspect, the energy absorption occurs as in the case where a groove is provided in the platen as described above. The flat spring 5415 shown in FIG. 45 may further be incorporated in the configuration shown in FIG. 46.

Furthermore, in this Example, a sintered PZT piezoelectric body is used as the sensor, phosphor bronze is used for the flat spring, stainless steel (SUS32) is used for the impact portion, hollow glass is used as the bearing portion, and an aluminum material is used as the platen, and a groove having a diameter of 5 mm and a depth of 0.2 mm is provided as the groove. In addition, Fe is used for the impact portion, but instead thereof, for example, a metal material, a ceramic material and a polymer material may be used, and Fe, Al, brass and carbon steel may preferably be used, or magnetic Fe, Ni, Co and Gd may be used, or alloys and ceramics thereof may be used. For example, Fe, Co., Ni, Gd and alloys or ceramics thereof may be used. An Fe based magnet containing Si is used in this Example, but an electromagnet may be used. In addition, phosphor bronze is used as the flat spring, but other materials having elasticity and spring properties are also acceptable, and instead thereof, for example, a Be—Cu alloy and stainless steel (SUS) may be used. The PZT piezoelectric body is used as the sensor 1, but instead thereof, for example, ZnO and barium titanate may be used.

In addition, as an aspect other than the above Example, a piezoelectric body 5901 serving as a sensor and a flat spring 5902 are provided in the groove 5420, and elastic energy is accumulated in the input spring 5415 connected to the spring fitting portion 5416, kinetic energy generated by releasing the elastic energy (accumulation and release of energy in the input spring are not shown) is given to the recoil body composed of the connected movable axis portion 5426 and impact portion 5427, and the recoil body collides against the sheet material 5410 with the sheet material 5410 as printing paper being therebetween, and the sheet material 5410 is deformed at the time of the collision, and the flat spring 5902 is also deformed in association with the deformation of the sheet material 5410, and therefore the original elastic energy is reduced due to the consumption of the deformation energy, and the recoil body goes away from the sheet material 5410 with residual energy. In the process of repeating the above operations, the input spring has original energy gradually reduced, and finally falls onto the sheet material. In the process of the above operations, the flat spring 5902 starts moving with the impulse occurring at the time of the collision, and at the same time, the piezoelectric body 5901 is deformed, and the piezoelectric current generated by deformation of the piezoelectric body 5901 is detected as a voltage.

That is, the time of the collision is measured using the trigger of voltage generated in the piezoelectric body. Then, as in the case of the above Example, by measuring the time interval of the collision depending on the rigidity of sheet material using the trigger, the type of sheet material can be detected.

Example 13

Figure 49:
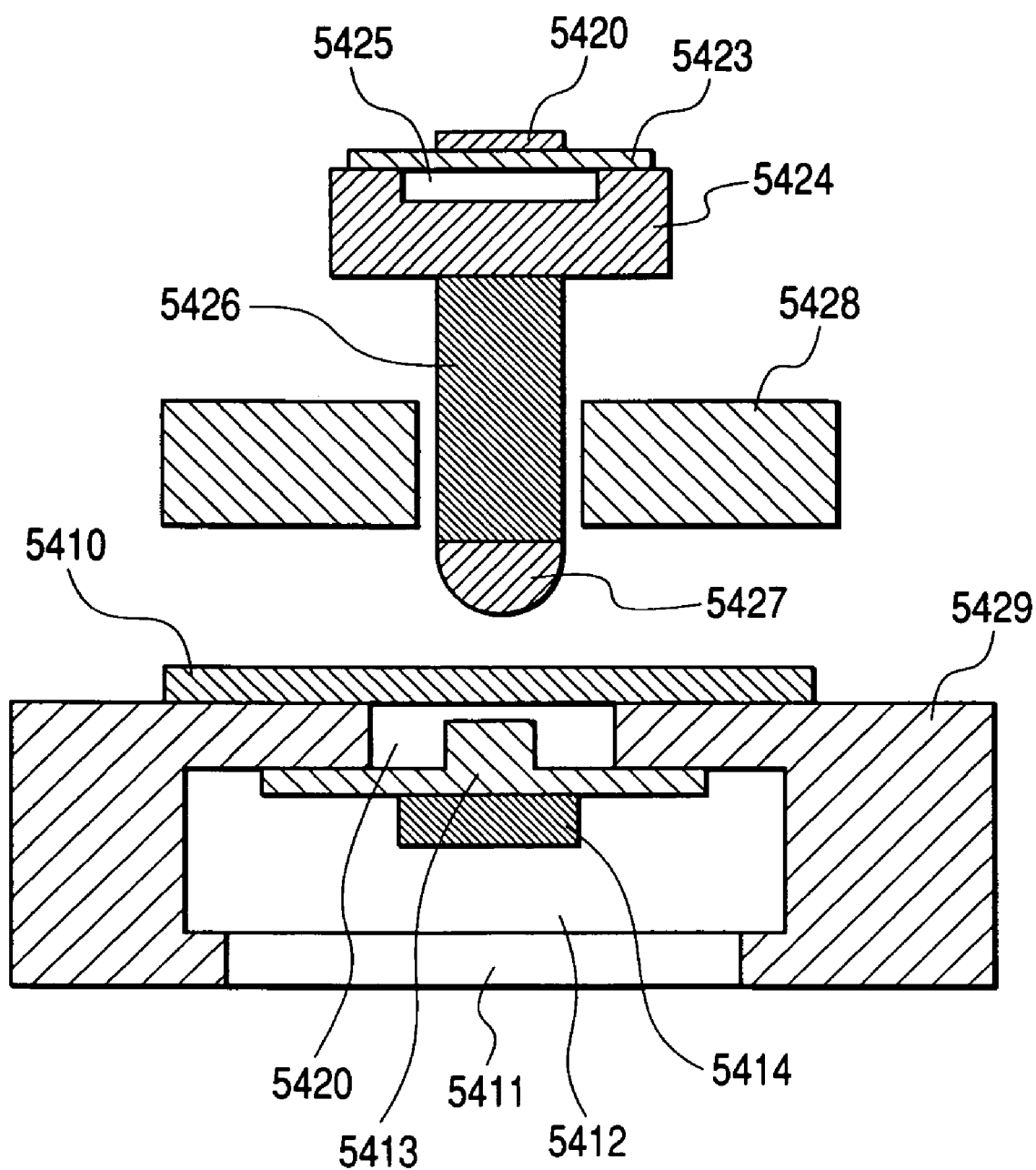
FIG. 49 illustrates the signal output apparatus according to the present invention.

This Example will be described with reference to FIG. 49. Same numbers are given for portions same as those in FIG. 46. Reference numeral 5413 denotes an absorber placed in the groove 5420, and reference numeral 5414 denotes a magnet.

Figure 48:
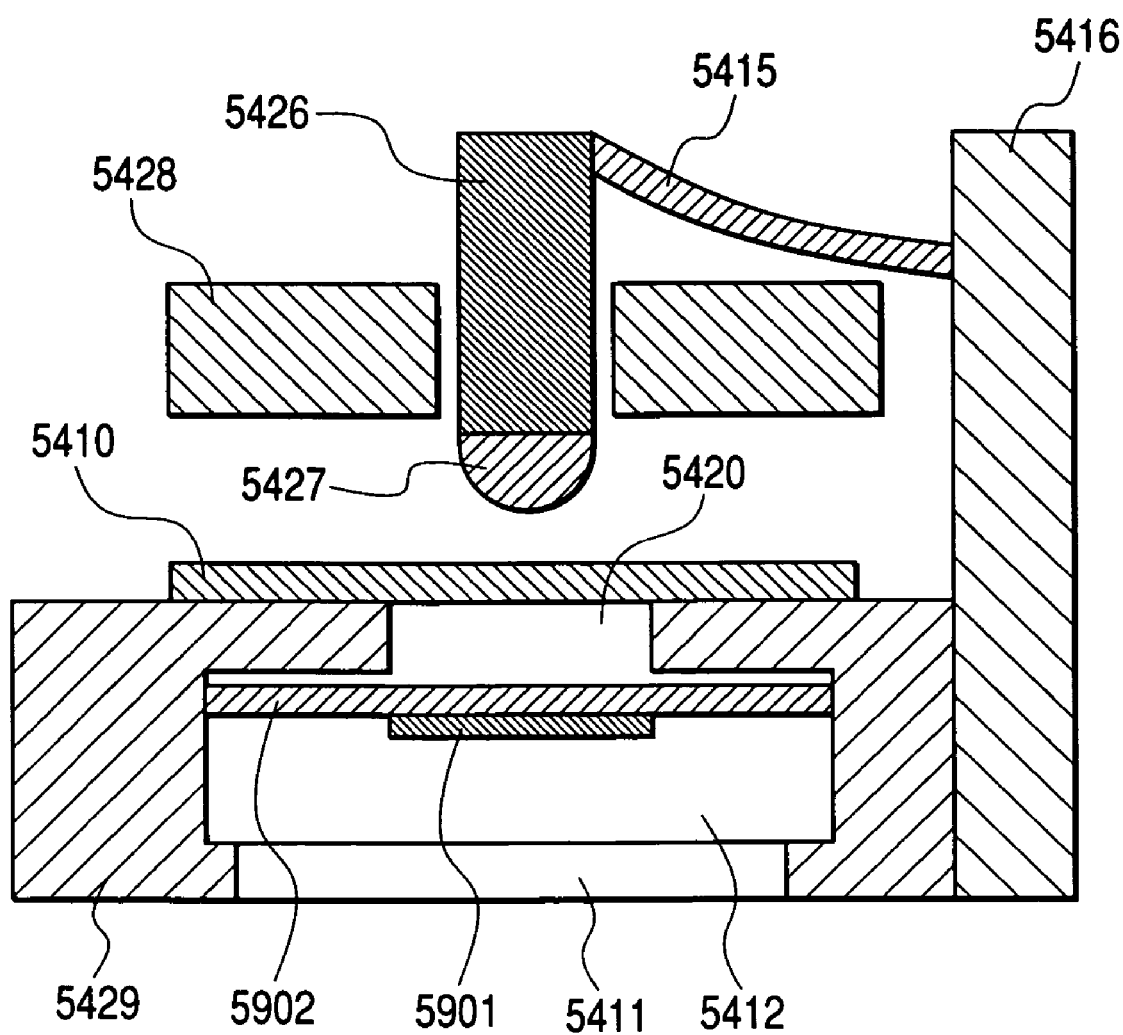
FIG. 48 illustrates the signal output apparatus according to the present invention.

Either gravity or the flat spring 5415 (FIG. 48) may be used for collision of the impact portion 5427 against the sheet material.

In this Example, attractive forces are exerted between the recoil body and the magnet 5414. The impact portion at the front edge of the recoil body approaches close to the magnet 5414, and at this time, inter-magnetic material attractive forces are exerted between the recoil body and the magnet.

Thus, the recoil body gradually goes away from the magnet and the sheet material to rise into space with residual energy, in the teeth of the inter-magnetic material attractive force.

In this Example described above, the length of the approach distance from the recoil body to the magnet of the impact portion depends on the rigidity of the sheet material, and therefore by providing the magnet 5414 in the groove of the platen, the inter-magnetic material attractive force decreases as the rigidity increases, and conversely, the inter-magnetic material attractive force increases as the rigidity decreases. Thus, the height reached by the recoil body rising into space after the collision for the sheet material having high rigidity than that for the sheet material having low rigidity, and consequently, there is a difference in time interval of the collision of the recoil body between sheet materials. That is, the time interval increases as the rigidity of sheet material increases.

In this Example described above, the type of printing paper can be detected by measuring the time interval in the case where a magnet is placed in the groove.

Figure 50A:
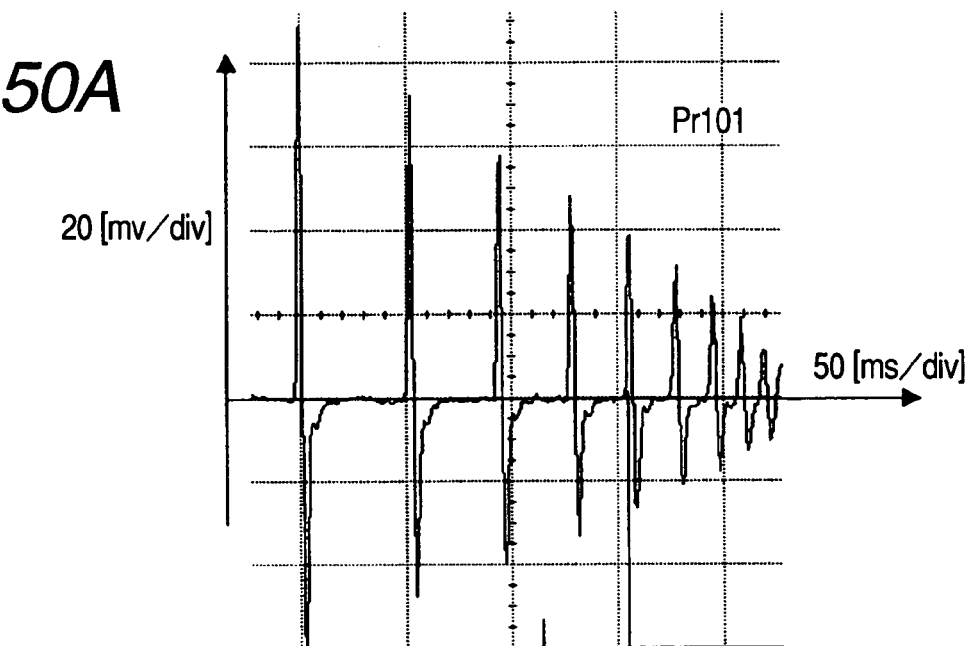
FIGS. 50A and 50B show examples of the output signal according to the present invention.
Figure 50B:
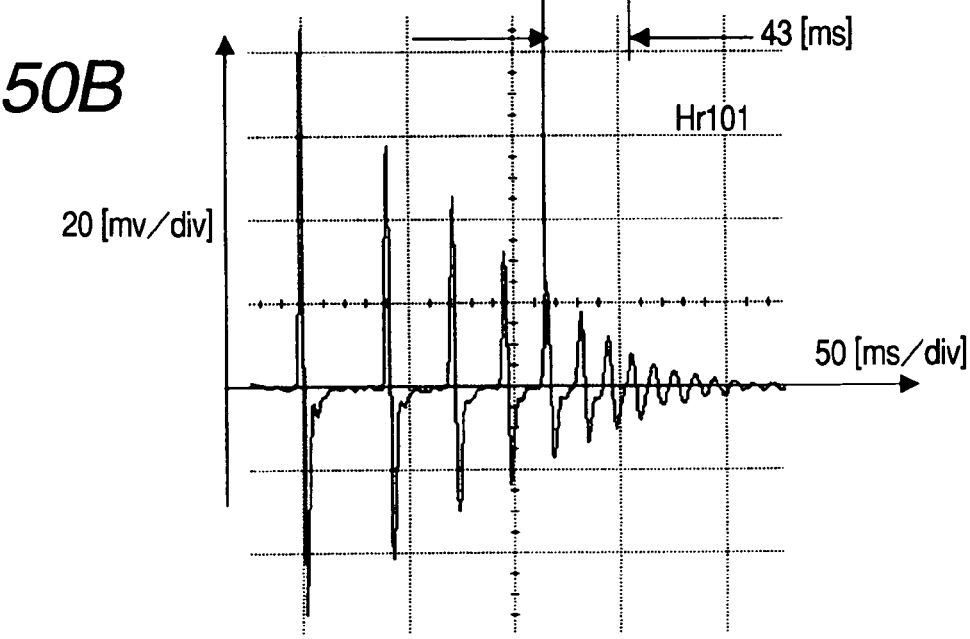

In this Embodiment, when the above method and apparatus were used to the type of sheet for Pr 101 and Hr101, there was a difference of 43 ms between these two papers in time interval between the first recoil and the fifth recoil as shown in FIGS. 50A and 50B, and thus the type could be clearly determined.

In this Example described above, a magnet with magnetic flux of 470 (Gauss) is used as the magnet, and a groove 10 having a diameter of 5 mm and a depth of 0.2 mm is provided, and the recoil body with weight of 7 (gr.multidot.f) is fallen from the height of 7 mm using mild steel as the impact portion.

Furthermore, a groove having a diameter of 5 mm and a depth of 0.2 mm is used, but instead thereof, a groove having a shape or dimension enabling the sheet material to undergo deformation depending on the rigidity of sheet material at the time of the collision may be used.

Figure 51:
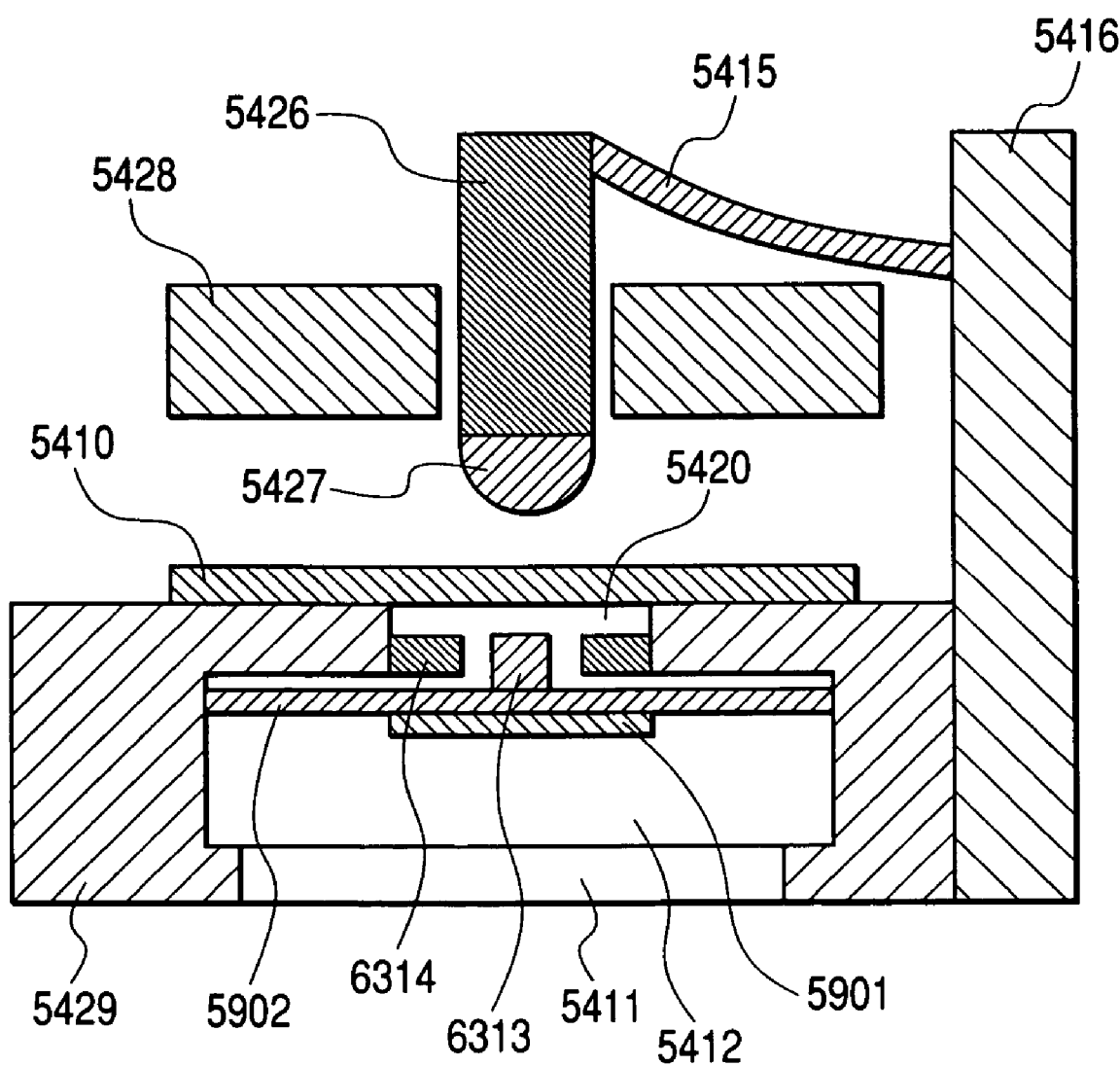
FIG. 51 illustrates the signal output apparatus according to the present invention.

In addition, as another aspect, the piezoelectric body 5901 acting as a sensor, the flat spring 5902, an absorber 6313 and a magnet 6314 may be provided in the groove 5420 as shown in FIG. 51.

According to the signal output apparatus according to the present invention, information about the type of sheet material can be outputted even if information such as number codes is not previously assigned to the sheet material.

Example 14

Figure 55:
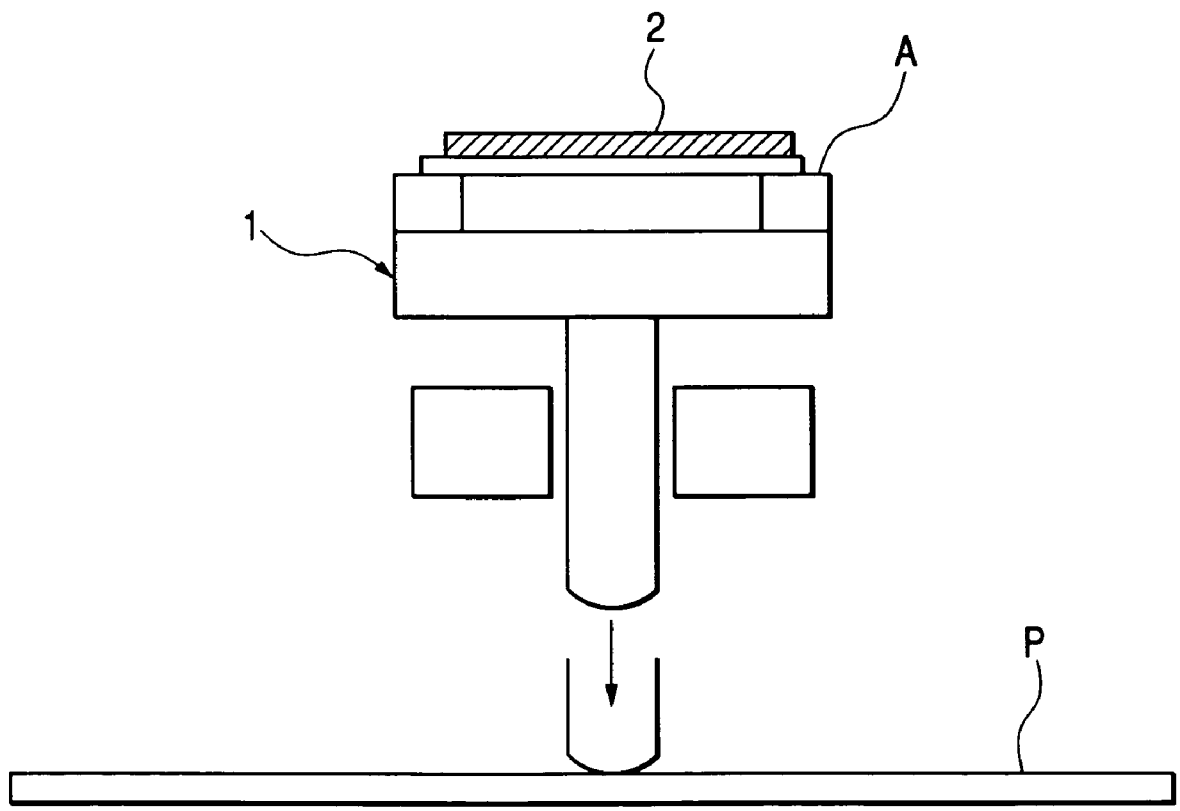
FIG. 55 illustrates an example of the apparatus for determining the type of sheet of the present invention.
Figure 56A:
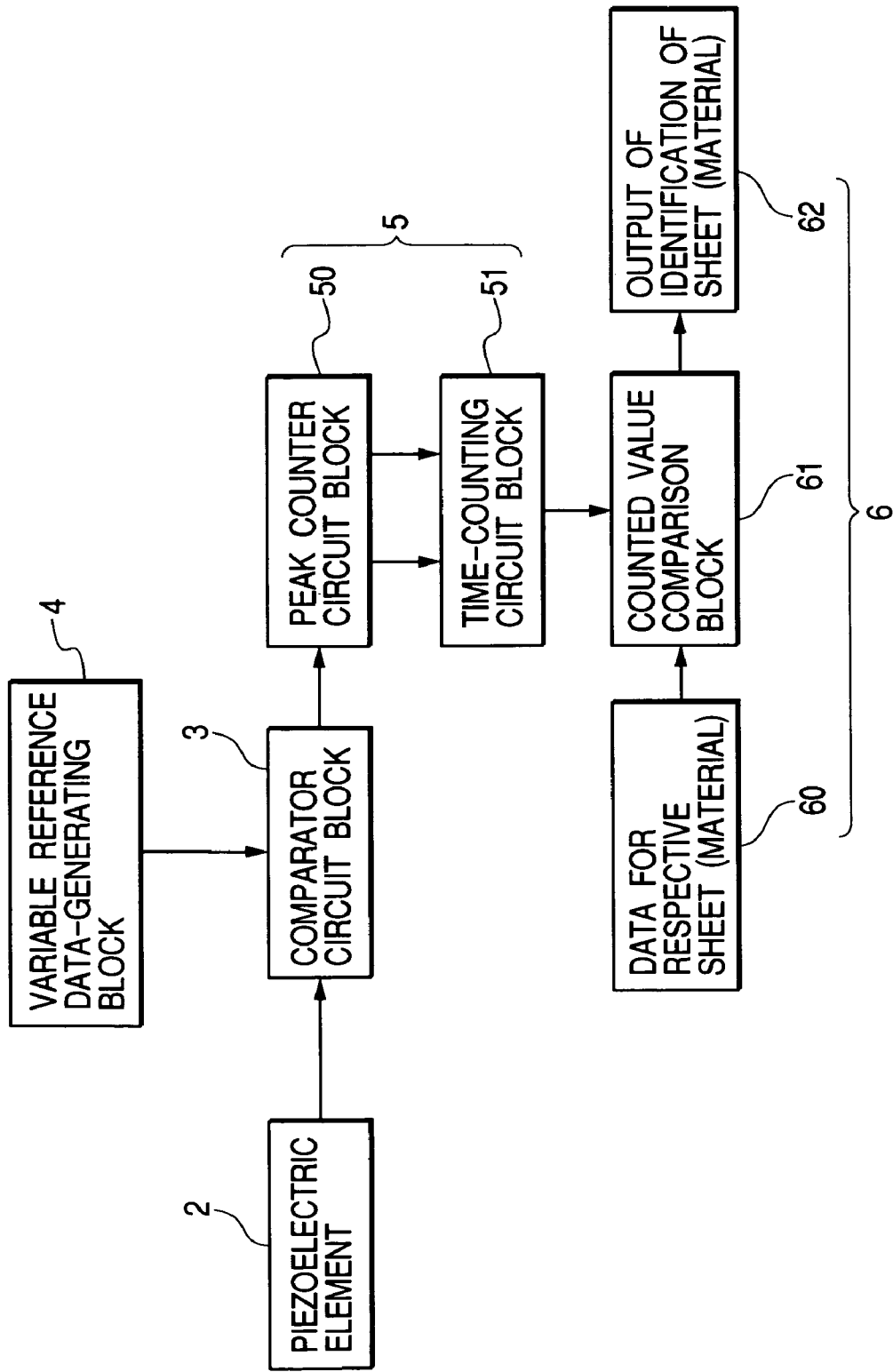
FIGS. 56A and 56B show a block diagram showing an example of constitution of the apparatus for determining the type of sheet of the present invention.
Figure 56B:
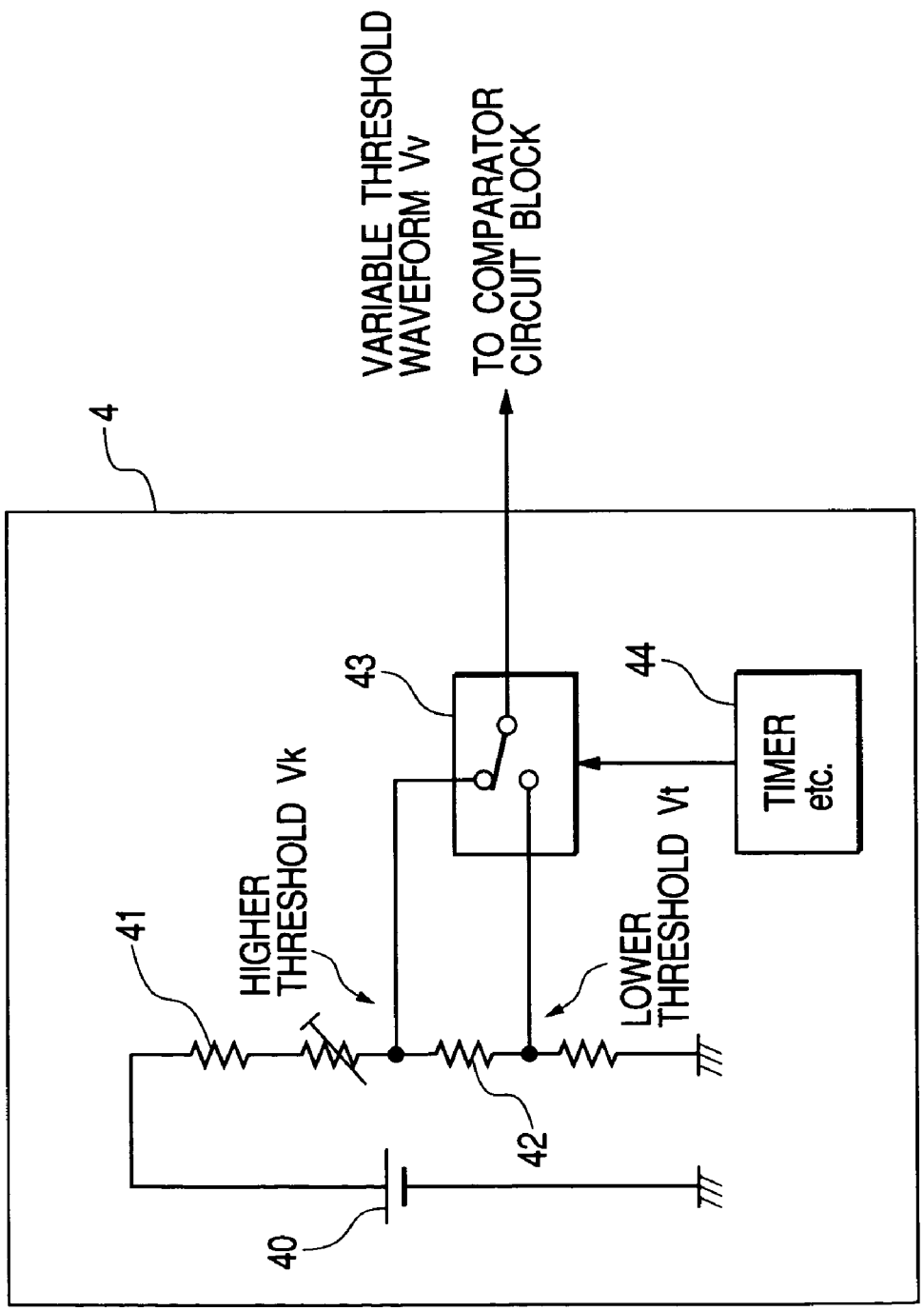
Figures 57A, 57B, 57C:
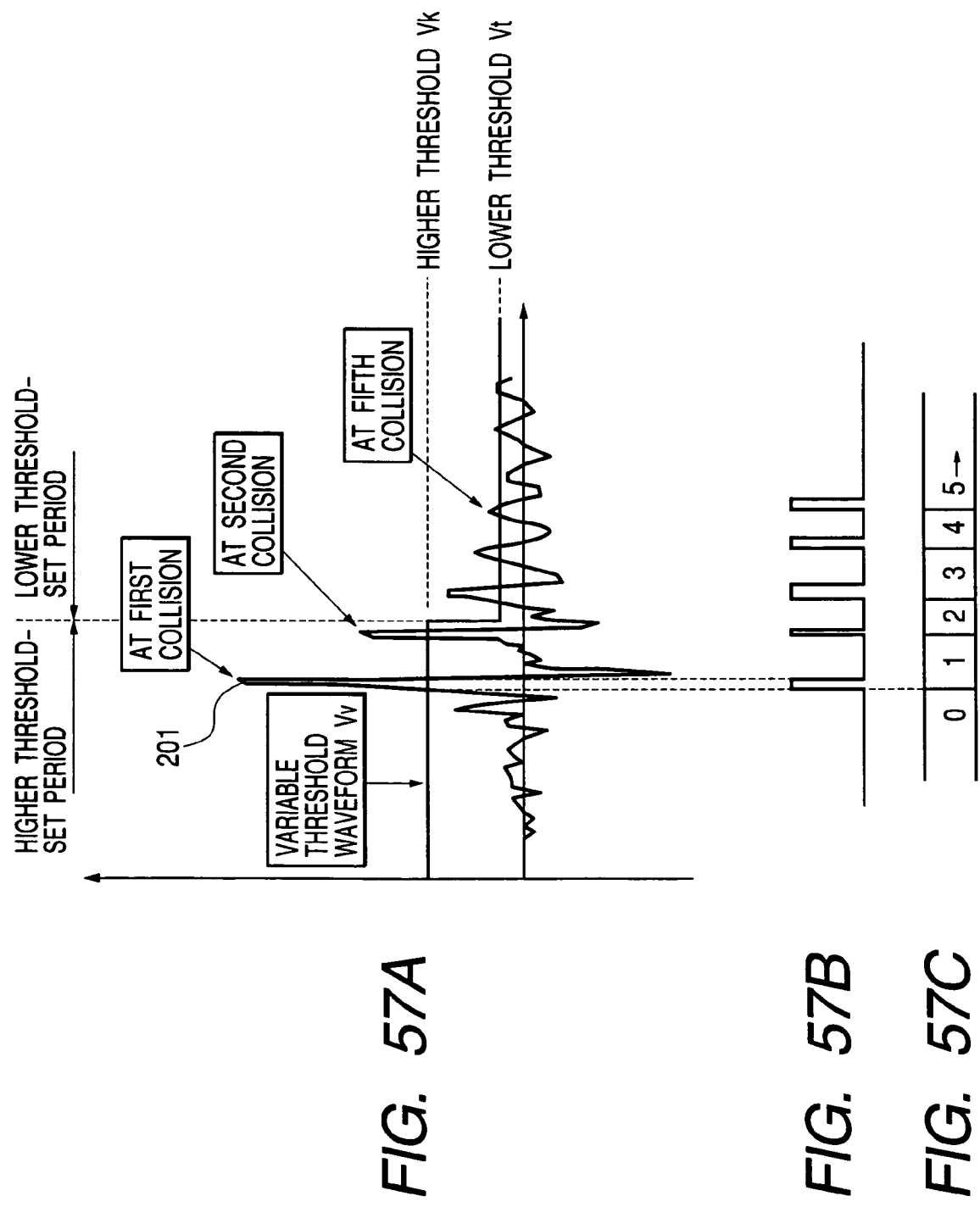
FIG. 57A is a waveform chart showing comparison of a signal outputted from a piezoelectric element with a threshold value.
FIG. 57B shows a waveform chart of the pulse outputted on the basis of the comparison.
FIG. 57C shows detection of the pulse intervals.

In this Example, a apparatus for determining the type of sheet as shown in FIGS. 55 and 56A and 56B is prepared, and the threshold is changed in two levels with lapse of time (symbol Vv in FIG. 57A).

In FIGS. 55 and 56A, the numerals denotes the following: 1, an impacting member to be rebounded on a sheet material P; 2, a piezoelectric element (sensor) attached to impacting member 1; 3, a comparator circuit block (pulse-generating means) which generates output (binary output) of "high" when output signal 201 is higher than a threshold Vv and generates output of "low" when output signal 201 is lower the threshold Vv; and 4, variable reference data-generating block (threshold setting means) for supplying a reference threshold voltage to the comparator circuit block 3. This variable reference data-generating block 4, as shown in FIG. 56B, has power source 40, resistance 41 for deciding high threshold Vk and low threshold Vt, switch 43 for switching the threshold level, and circuit 44 for operation of switch 43. In FIG. 56A, the numerals denotes the following: 50, a circuit for counting the times of output "high" from the comparator circuit block; 51, a time-counting circuit block for measuring the time (recoil period) between a first predetermined sequential order of rebounding and a second predetermined sequential order of rebounding; 60, a data table between predetermined orders of times for the types of the sheet material (i.e., data table memorizing the rebounding periods for various types of sheets); 61, a counted value comparison block for comparing the measurement time of the time-counting block and sheet type data in data table 60; and 62, a circuit block for identifying the sheet material based on the comparison results obtained by counted value comparison block 61.

The method for identifying a type of a sheet material is explained below.

When impact applying unit 1 is allowed to fall onto sheet material P and is rebounded therefrom, the output signal (201 in FIG. 37A) from piezoelectric element 2 is sent to comparator circuit block 3. On the other hand, to the comparator circuit block 3, a predetermined initial threshold (fixed value) is inputted from threshold-changing circuit block 4. From comparator circuit block 3, a pulse is inputted (only when the outputted signal from the piezoelectric element exceeds threshold Vv) to peak counter circuit block 50 (FIG. 57B). This threshold Vv is changed to a lower threshold Vt after the initial high threshold Vk is kept for a certain time as shown in FIG. 57A. Therefore, the first peak and the second peak are compared with the higher threshold Vk, and the third and subsequent peaks are compared with the lower threshold Vt. Thereby a pulse is outputted at every collision of impact applying unit 1 against sheet material P. Even if the output signal from piezoelectric element 2 has the waveform shown by reference numeral 202 in FIG. 58A, pulses are outputted.

The binary pulse obtained by the comparator is counted by peak counter circuit block 50, and the count number is outputted (FIG. 56A). Time counter circuit block 51 starts the counting from a predetermined count number, and stops the counting to obtain a recoil period. This measured time interval is compared with the preliminarily determined data for the sheet material types by the counter value comparison block, whereby the type of the sheet material is identified.

The threshold value may be generated by a microcomputer processing circuit utilizing an A/D converter.

Example 15

In this Example, the threshold for comparison of the signal waveform on the second or later collision is computed from the maximum voltage and the minimum voltage at the preceding collision, and is changed stepwise.

Figure 59:
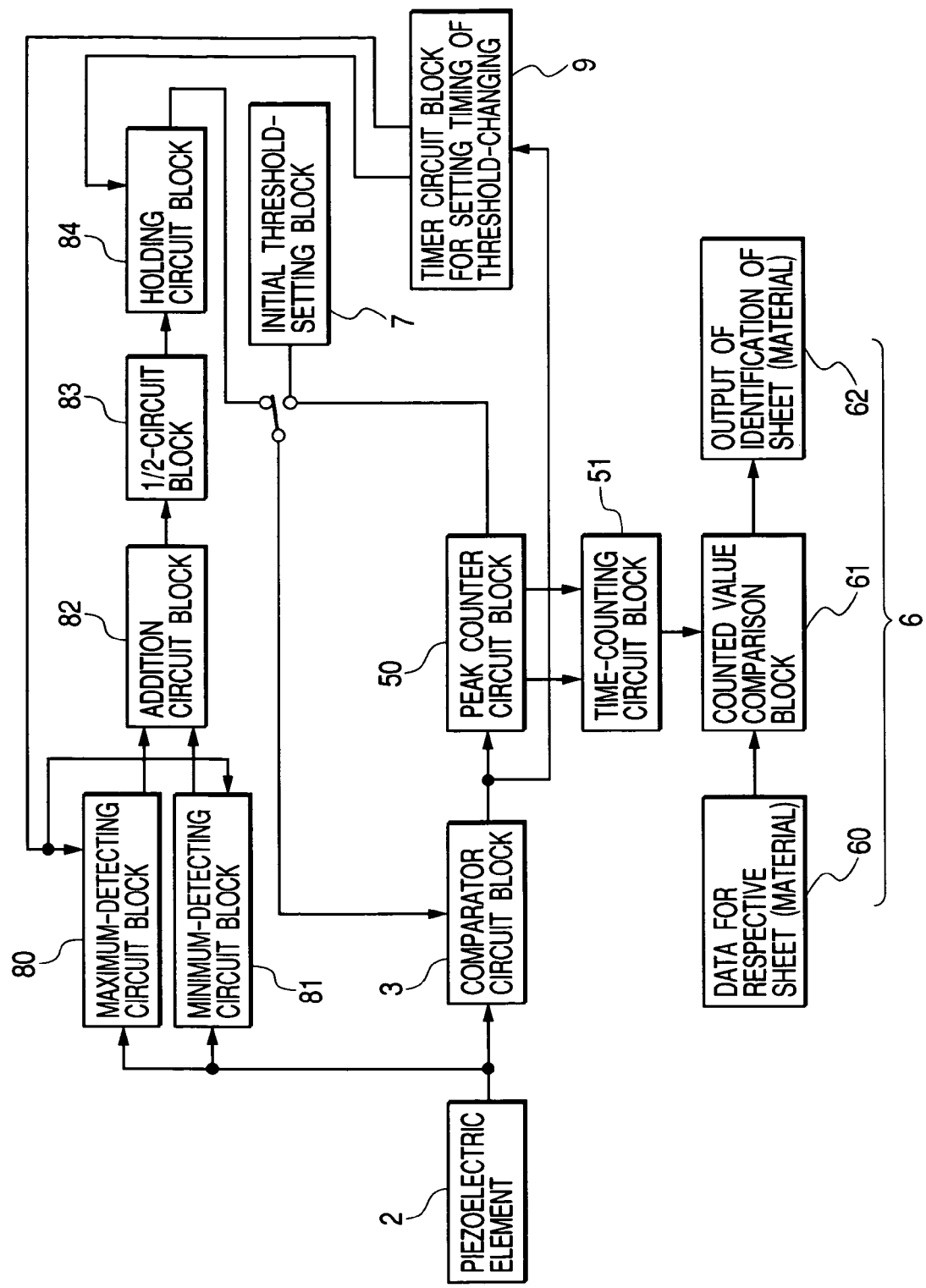
FIG. 59 is a block diagram showing an example of constitution of the apparatus for determining the type of sheet of the present invention.

In this Example, a apparatus for determining the type of sheet is prepared as shown in FIG. 59. In FIG. 59, the reference numerals denotes the following: 80, a maximum-detecting circuit block for detecting a maximum of the output signal from piezoelectric element 2; 81, a minimum-detecting circuit block for detecting a minimum of the output signal from piezoelectric element 2; 82, an addition circuit block for adding the maximum and the minimum; 83, a ½-circuit block for computing the average of the maximum and the minimum by dividing the output from addition circuit block 82 by 2; 84, a holding circuit block for holding the average of the maximum and the minimum; 9, a timing circuit block for setting a detection timing in maximum-detecting circuit block 80 and minimum-detecting circuit block 81 respectively and setting a holding value set-timing in holding circuit block 84; and 7, an initial threshold-setting block for setting a threshold for the first collision in comparator circuit block 3. This threshold is selected only for the first collision.

Figures 60A, 60B, 60C:
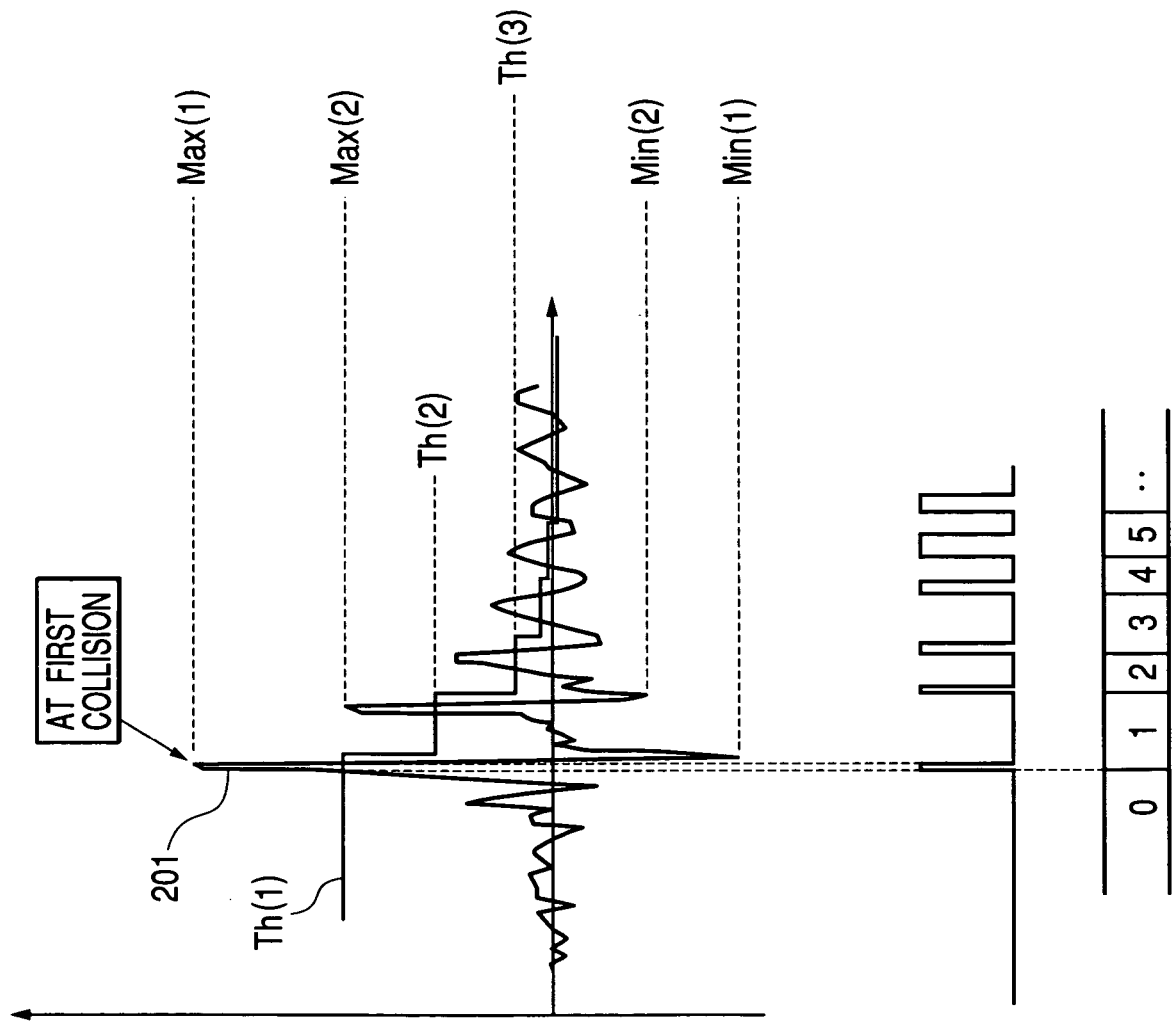
FIG. 60A is a waveform chart showing comparison of a signal outputted from a piezoelectric element with a threshold value.
FIG. 60B shows a waveform chart of the pulse outputted on the basis of the comparison.
FIG. 60C shows detection of the pulse intervals.

As shown in FIG. 60A, output signal 201 from piezoelectric element 2 is inputted into comparator circuit block 3, and is therein compared with initial threshold Th(1) at the first collision. Thereby a binary pulse is outputted (FIG. 60B).

At the first collision, the maximum, Max(1), of the output signal of the piezoelectric element and the minimum, Min(1), thereof are detected respectively by maximum-detecting circuit block 80 and minimum-detecting circuit block 81. The maximum and the minimum are averaged by addition circuit block 82 and ½-circuit block 83 to obtain an average (Th(2)). The average is inputted to holding circuit block 84. Then, at a timing selected by timing circuit block 9 for threshold setting, the output from holding circuit block 84 is changed to the average, Th(2), of the maximum, Max(1), and the minimum, Min(1). The value of Th(2) is fed as the threshold for the second collision to comparator circuit block 3.

Similarly, the threshold, Th(3), at the third collision is the average of the maximum, Max(2), and the minimum, Min(2), of the second collision.

Thus, in this Example, the threshold Th(n) at the n-th collision is represented by $$Th(n)=(Max(1)+Min(1))/2$$

where 1=n−1, and n is an integer of 2 or more. At the first collision, the initial threshold is employed. At the second and later collisions, the thresholds are taken which are calculated by the equation above, namely the average of the maximum and the minimum of the output signal at the preceding collision.

Figure 61A:
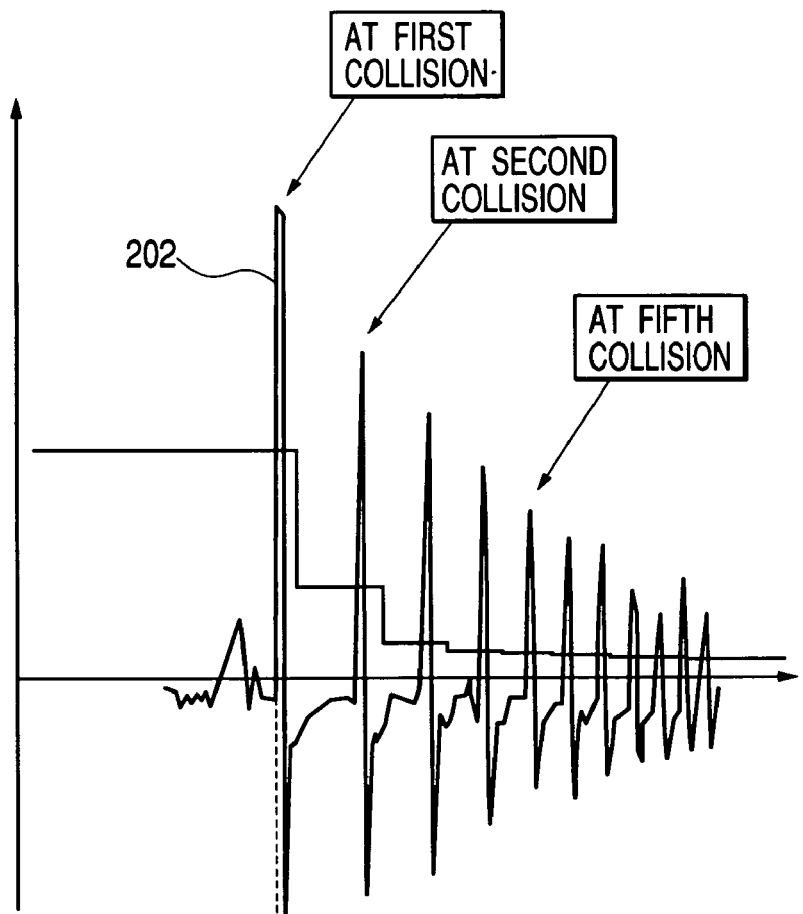
FIG. 61A is a waveform chart showing comparison of a signal outputted from a piezoelectric element with a threshold value.
Figure 61B:
FIG. 61B shows a waveform chart of the pulse outputted on the basis of the comparison.
Figure 61C:
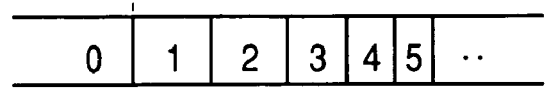
FIG. 61C shows detection of the pulse intervals.

Thereby, even with the signal having a waveform shown by the numeral 202 in FIG. 61A, the collision of impact applying unit 1 can be detected precisely, and the sheet material can be identified therefrom.

The maximum voltage and the minimum voltage may be converted by A/D conversion or the threshold may be converted by A/D conversion by microcomputer processing.

Example 16

In the above described Example 14, the initial threshold (the threshold for the comparator in the first collision) is preliminarily set at a prescribed level. In contrast, in this Example, the paper sheet material is preliminarily tested (for determination of the threshold only (hereinafter referred to as "trial measurement")) before conducting the practical identification of the paper sheet material (hereinafter referred to as "practical measurement"), and the threshold determined by the trial measurement is used as "the initial threshold at the first collision for practical identification of the paper material". In other words, in this Example, the initial threshold in the practical identification of the paper sheet material is predetermined by conducting the preliminary trial measurement to measure the maximum at the first collision and halving the maximum.

Figure 62A:
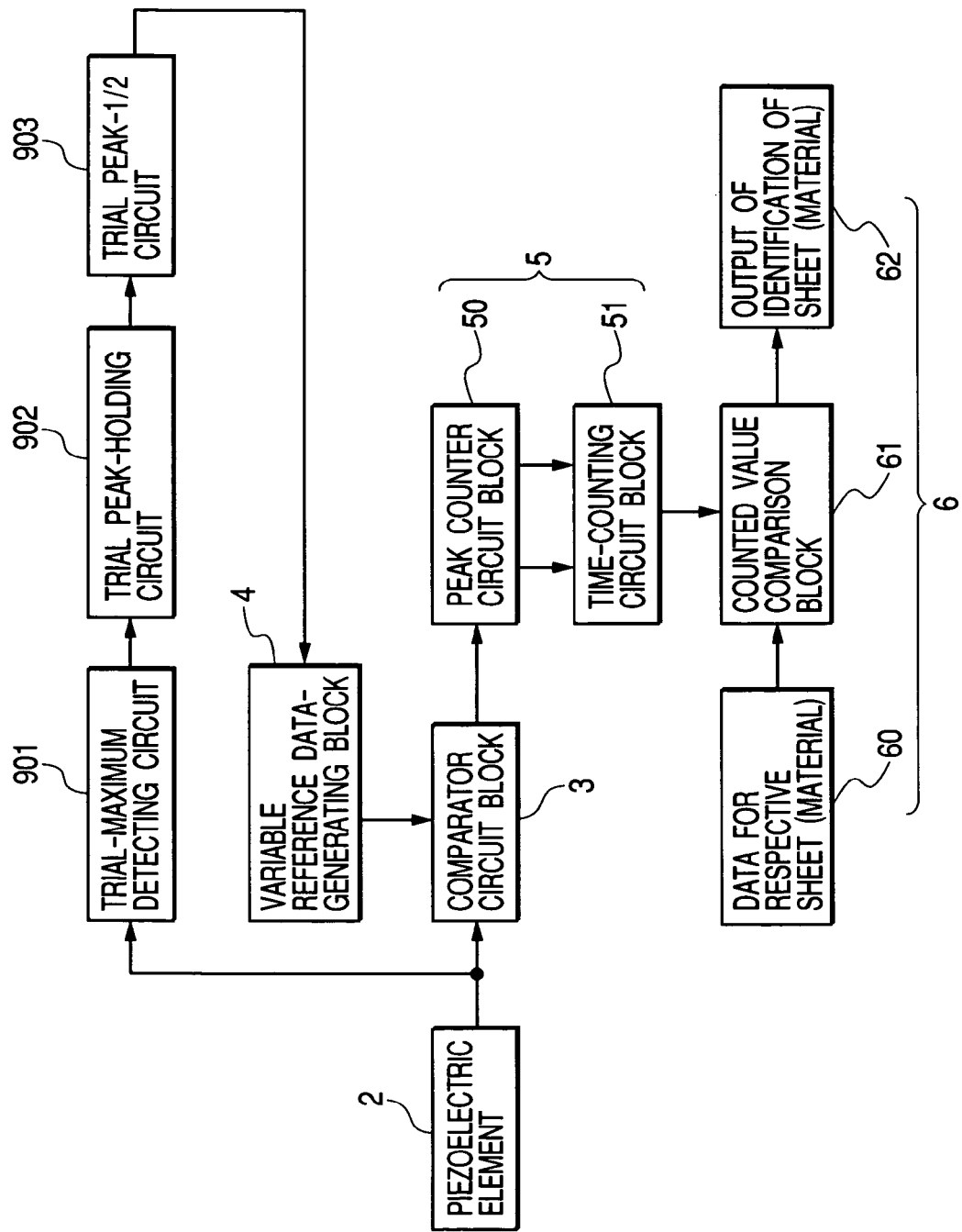
FIGS. 62A and 62B are block diagrams showing an example of constitution of the apparatus for determining the type of sheet of the present invention.
Figure 62B:
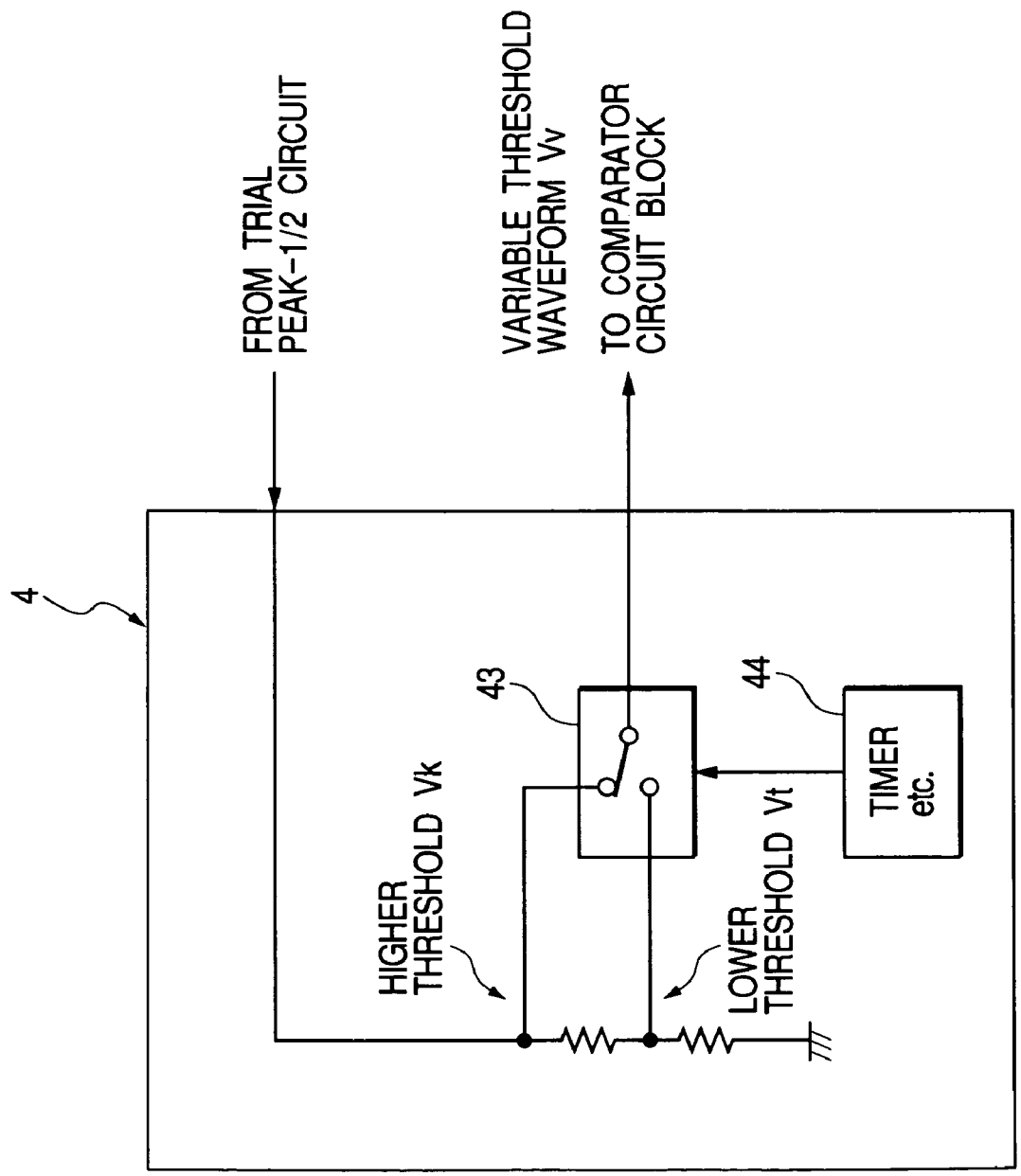

In this Example, an apparatus is prepared as shown in FIGS. 62A and 62B. In FIG. 62A, the numeral 901 denotes a trial-maximum detecting circuit for detecting the maximum of the piezoelectric element in the trial measurement; the numeral 902 denotes a trial peak-holding circuit for holding the maximum obtained in the trial measurement by trial maximum-detecting circuit 901 until the practical measurement is conducted; and the numeral 903 denotes a ½ circuit block for halving the held maximum value. Otherwise the constitution is the same in FIGS. 56A and 56B.

[Trial Measurement]

Figure 63:
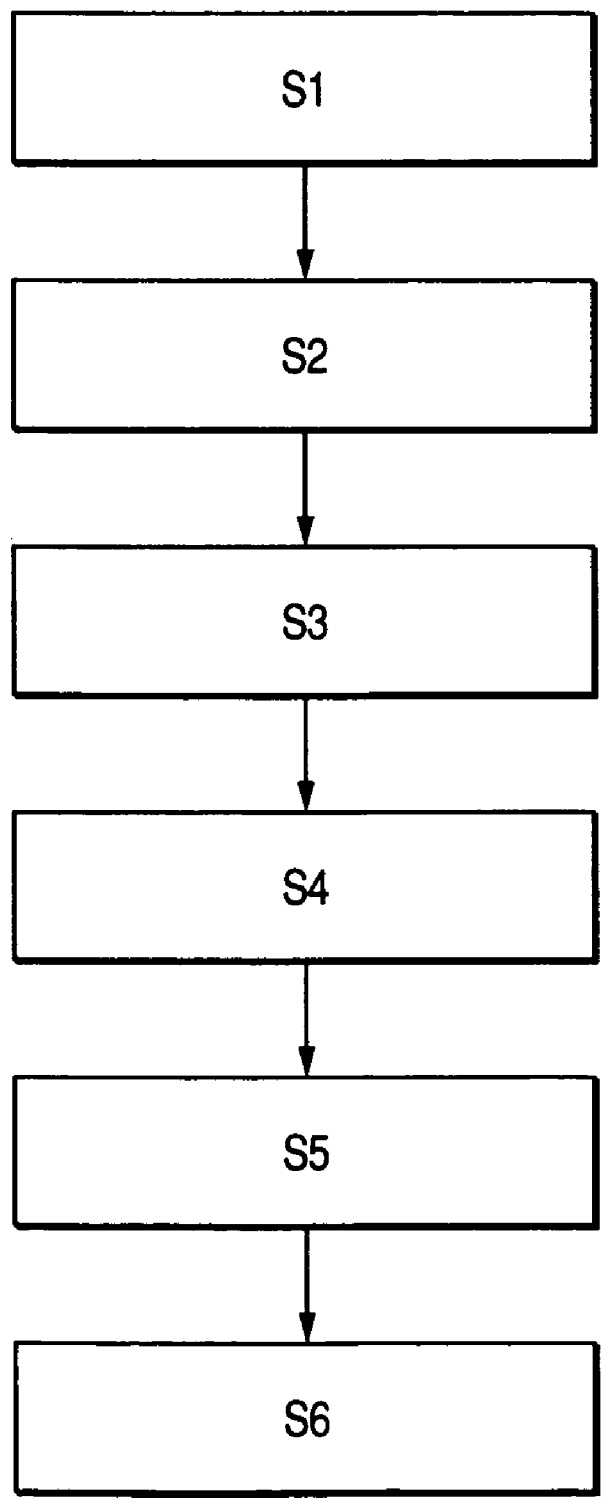
FIG. 63 is a flow chart for identifying a type of the sheet material.

Firstly, in the trial measurement, impact applying unit 1 is allowed to collide against sheet material P (Steps S1 and S2 in FIG. 63). The maximum output of the piezoelectric element at the first collision is detected by trial maximum-detecting circuit block 901. The detected maximum output is held by trial peak-holding circuit 902, halved by trial peak-½-circuit 903 (Step S3 in FIG. 63), and fed to comparator circuit 3 as the threshold.

[Practical Measurement]

In the practical measurement, impact applying unit 1 is allowed to collide against sheet material P (Step S4 in FIG. 63) to identify a type of the sheet material in the same manner as in Example 14 (Steps S5 and S6 in FIG. 63). As the initial threshold, the value obtained by the trial measurement is used.

The maximum in the trial measurement may be A/D-converted and the threshold value may be D/A-converted to input to the comparator circuit.

Example 17

Figure 64:
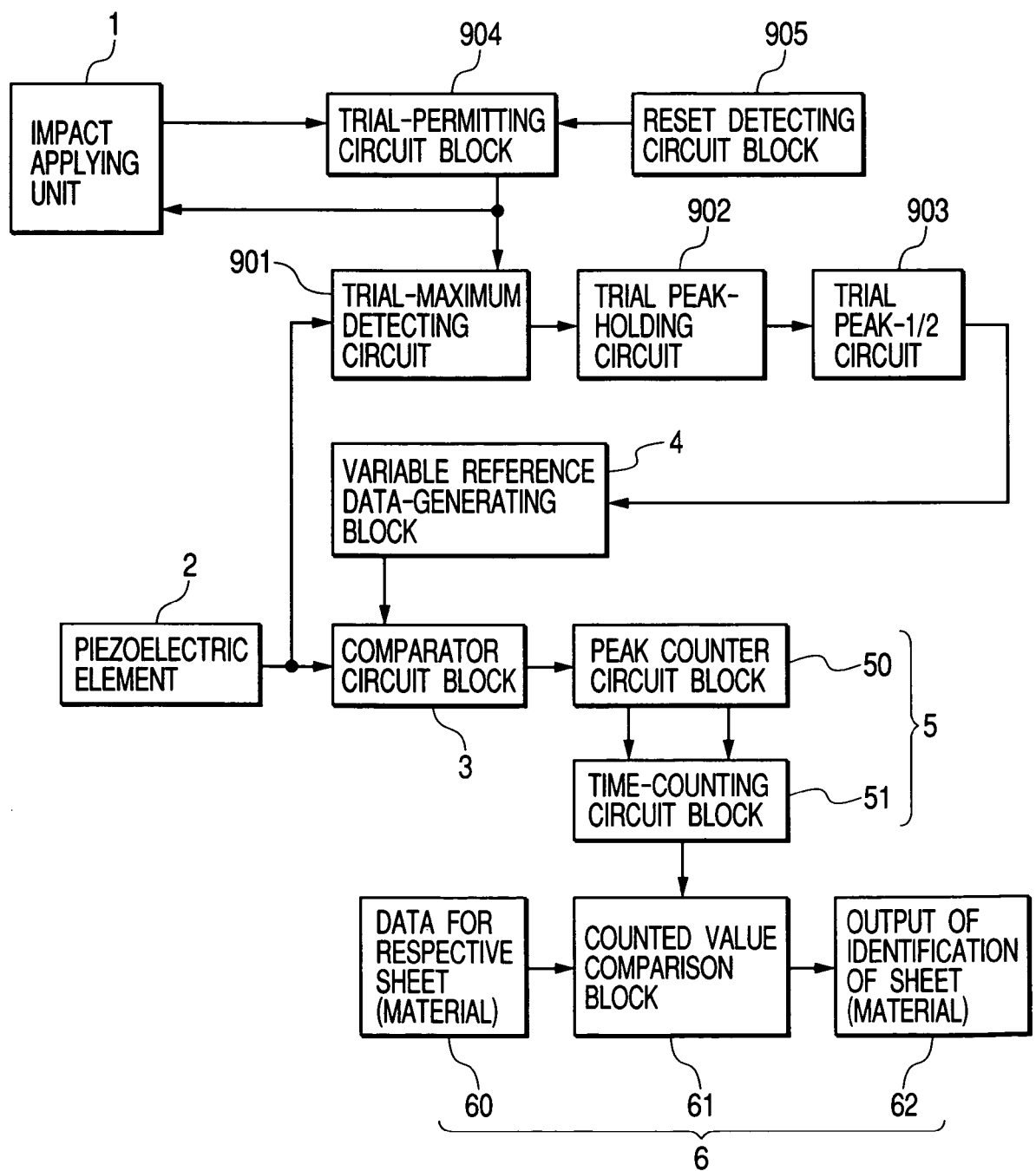
FIG. 64 is a block diagram showing an example of constitution of the apparatus for determining the type of sheet of the present invention.

In this Example, the apparatus for determining the type of sheet having the constitution shown in FIG. 64 is mounted on a machine like a copying machine (hereinafter referred to as "a paper-identifying unit-carrying machine"), and the trial measurement as conducted in Example 3 (paper identification for obtaining the threshold only) is conducted at the power switch-on and resetting of the paper-identifying unit-carrying machine.

In FIG. 64, the numeral 904 denotes a trial-permitting circuit block for permitting the trial by sending a signal to trial maximum-detecting circuit block 901 to allow impact applying unit 1 to rebound from sheet material P. The numeral 905 denotes a reset detecting circuit block for detecting the reset signal emitted from the paper-identifying unit-carrying machine.

Reset detecting circuit block 905 detects the reset signal from the paper-identifying unit-carrying machine and transmits it to trial-permitting circuit 904. Trial-permitting circuit 904 gives indication for impact application, and transmits an operation permission signal from trial maximum detecting circuit block 901 to conduct the trial operation.

Example 18

Figure 65:
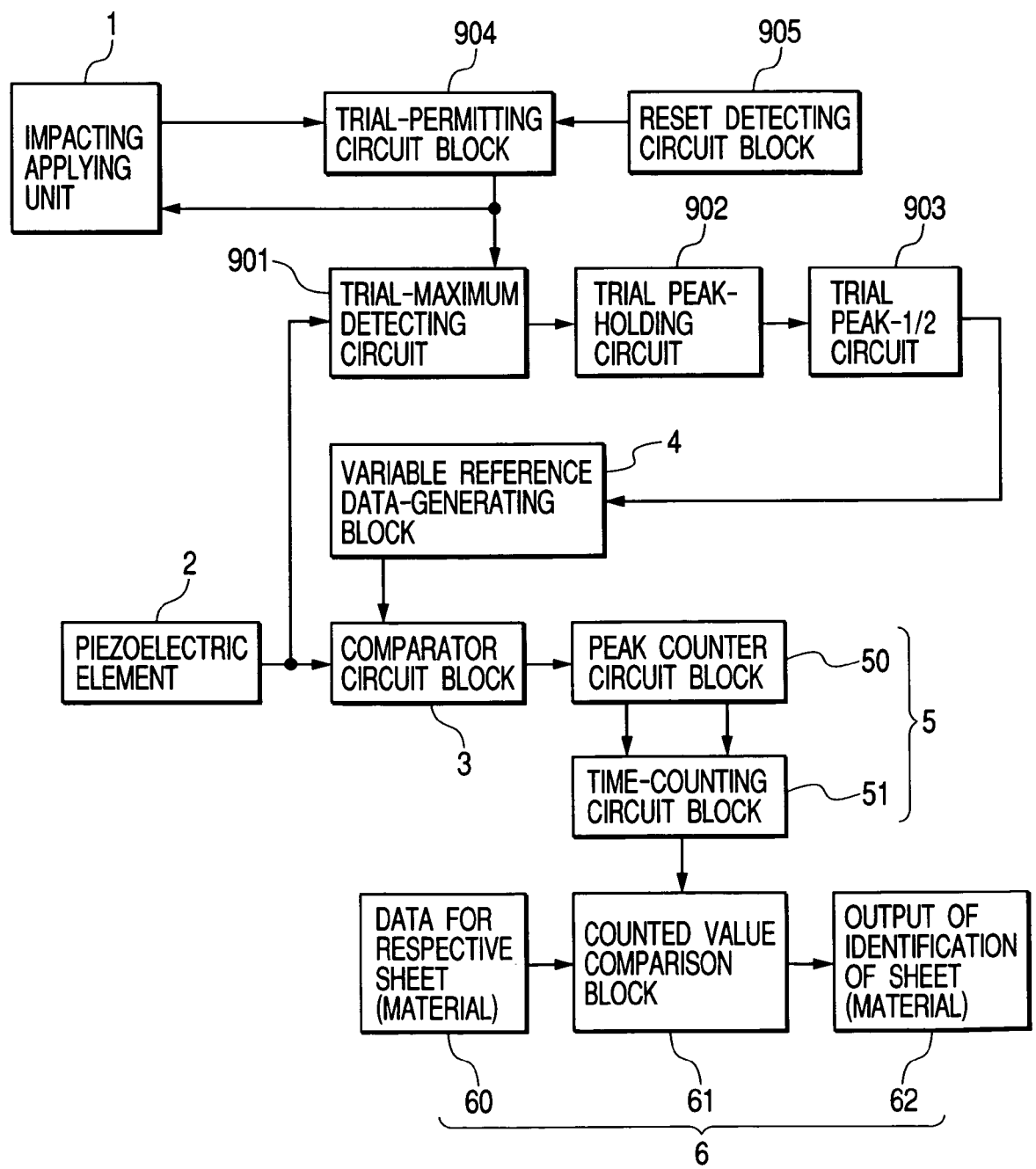
FIG. 65 is a block diagram showing an example of constitution of the apparatus for determining the type of sheet of the present invention.

In this Example, the apparatus for determining the type of sheet having the constitution shown in FIG. 65 is mounted on a machine like a copying machine (hereinafter referred to as "a paper-identifying unit-carrying machine"), and the trial measurement conducted in Example 3 (paper sheet identification conducted only for obtaining the threshold) is conducted when change of the paper type is expected.

The numeral 1101 denotes a circuit block for detection of exchange of the paper feed tray in the paper-identifying unit-carrying machine.

Circuit block 1101 for detection of exchange of the paper feed tray after detection of the exchange of the paper feed tray in the paper-identifying unit-carrying machine sends a signal of paper feed tray exchange to trial permitting circuit 904. The trial permitting circuit 904 is driven in accordance with a paper feed tray exchange signal, giving instruction for the trial operation to impacting driver circuit 301 and trial maximum-detecting circuit block 901 to conduct the trial operation. Other operations are conducted in the same manner as in the above Examples.

What is claimed is:

1. An image-forming apparatus comprising an apparatus for determining the type of sheet, and an image-forming section for forming an image under conditions corresponding to the identified sheet material, wherein
    the apparatus for determining the type of sheet comprises
    an impact applying unit for applying an impact against a sheet material,
    a detection unit for outputting a signal in response to the impact,
    a pulse-generating means for generating a pulse in response to a signal outputted from the detection unit at or above a prescribed threshold level, and
    a threshold-setting means for setting the threshold in correspondence with intensity of the signal.

2. The image-forming apparatus according to claim 1, wherein the threshold-setting means computes the threshold on start or reset of the image-forming apparatus.

3. The image-forming apparatus according to claim 1, wherein the threshold-setting means computes the threshold when a change of the sheet material is expected.

4. A method of identifying a type of a sheet material comprising the steps:
    applying an impact force to the sheet material;
    detecting attenuation of the applied impact force by the sheet material;
    outputting a signal in correspondence with the detected force;
    generating a pulse when the signal is at or above a prescribed threshold;
    setting the prescribed threshold; and
    identifying the type of the sheet material based on the output of the pulse generated according to the threshold set above,
    wherein the threshold is set according to the output state of the signal.

5. An information output apparatus used in an image forming apparatus, comprising:
    an impact applying unit applying an impact to a target from the outside thereof;
    a detection unit outputting information by the impact, wherein said target is a liquid container, and said impact is an external force other than vibration.

6. A signal output apparatus comprising:
    an impact applying unit for applying an impact to a sheet;
    a substrate for supporting the sheet;
    an impact receiving unit for receiving the impact through the sheet; and
    a signal output unit for outputting a signal according to a mechanical property of the sheet, the signal output unit being provided on at least one of the impact applying unit side and the impact receiving unit side,
    wherein the impact receiving unit is provided in a recess of the substrate, and, the level of the surface of the impact receiving unit is lower than the level of the surface of the substrate.

7. The signal output apparatus according to claim 5, wherein the level of the surface of the impact receiving unit is designed so as to make the impact receiving unit and the sheet not come in contact with each other at a position opposite to the impact applying unit before an impact is applied to the sheet and come into contact with each other when the impact is applied to the sheet.

8. A signal output apparatus comprising:
    an impact applying unit for applying an impact to a sheet;
    an impact receiving unit for receiving the impact through the sheet; and
    a signal output unit for outputting a signal according to a mechanical property of the sheet, the signal output unit being provided on at least one of the impact applying unit side and the impact receiving unit side,
    wherein the impact applied to the sheet by the impact applying unit causes the bending of the sheet, whereby the sheet and the impact receiving unit are made to come into contact with each other, to output the signal from the signal output unit, and wherein the impact applying unit applies a plurality of the impacts to the sheet.

9. A signal output apparatus comprising:
    an impact applying unit for applying an impact to a sheet;
    an impact receiving unit for receiving the impact through the sheet; and
    a signal output unit for outputting a signal according to a mechanical property of the sheet, the signal output unit being provided on at least one of the impact applying unit side and the impact receiving unit side,
    wherein the impact applied to the sheet by the impact applying unit causes the bending of the sheet, whereby the sheet and the impact receiving unit are made to come into contact with each other, to output the signal from the signal output unit, and wherein the impact applying unit applies plural kinds of impacts to the sheet.

10. A signal output apparatus comprising:
an impact applying unit for applying an impact to a sheet;
an impact receiving unit for receiving the impact through the sheet; and
a signal output unit for outputting a signal according to a mechanical property of the sheet, the signal output unit being provided on at least one of the impact applying unit side and the impact receiving unit side,
wherein the impact applied to the sheet by the impact applying unit causes the bending of the sheet, whereby the sheet and the impact receiving unit are made to come into contact with each other, to output the signal from the signal output unit, and wherein the impact is applied at the time when the sheet is moving.

11. A method for determining a sheet type, comprising the step of comparing an output signal from a signal output unit of a signal output apparatus with sheet information previously stored to determine the type of a sheet to which an impact was applied, wherein the signal output apparatus comprises:
an impact applying unit for applying an impact to a sheet;
an impact receiving unit for receiving the impact through the sheet; and
a signal output unit for outputting a signal according to a mechanical property of the sheet, the signal output unit being provided on at least one of the impact applying unit side and the impact receiving unit side,
wherein the impact applied to the sheet by the impact applying unit causes the bending of the sheet, whereby the sheet and the impact receiving unit are made to come into contact with each other, to output the signal from the signal output unit.

12. The method for determining the type of sheet according to claim 11, wherein the type of a sheet to be determined is the kind of material of the sheet.

13. The method for determining the sheet type according to claim 12, wherein the kind of material of the sheet is determined using a peak value of the output signal from the signal output unit.

14. The method for determining the sheet type according to claim 12, wherein the kind of material of the sheet is determined using a number of peaks of the output signal from the signal output unit or an interval of time between the peaks.

15. The method for determining the sheet type according to claim 12, wherein the kind of material of the sheet is determined using the n-th peak value and the (n+••)-th peak value, where •• represents a natural number, of the output signal from the signal output unit.

16. The method for determining the sheet type according to claim 12, wherein the kind of material of the sheet is determined using a recoil period of the impact applying unit.

17. An image forming apparatus comprising:
a signal output apparatus comprising:
an impact applying unit for applying an impact to a sheet;
an impact receiving unit for receiving the impact through the sheet; and
a signal output unit for outputting a signal according to a mechanical property of the sheet, the signal output unit being provided on at least one of the impact applying unit side and the impact receiving unit side; and
a memory unit in which information on sheets is stored,
wherein the impact applied to the sheet by the impact applying unit causes the bending of the sheet, whereby the sheet and the impact receiving unit are made to come into contact with each other, to output the signal from the signal output unit, and
wherein the image forming apparatus performs a function of determining the kind of material of the sheet using an output signal from the signal output unit of the signal output apparatus and information in the memory unit.

18. An image forming apparatus, which comprises:
a signal output apparatus comprising:
an impact applying unit for applying an impact to a sheet;
an impact receiving unit for receiving the impact through the sheet; and
a signal output unit for outputting a signal according to a mechanical property of the sheet, the signal output unit being provided on at least one of the impact applying unit side and the impact receiving unit side,
wherein the impact applied to the sheet by the impact applying unit causes the bending of the sheet, whereby the sheet and the impact receiving unit are made to come into contact with each other, to output the signal from the signal output unit, and
a conveying means which conveys a sheet; and
an image forming means for forming an image on the sheet,
wherein the conveying means is controlled by using an output signal from the signal output unit and a memory unit in which information on sheets is stored.

19. An image forming apparatus, which comprises:
a signal output apparatus comprising:
a signal output apparatus comprising:
an impact applying unit for applying an impact to a sheet;
an impact receiving unit for receiving the impact through the sheet; and
a signal output unit for outputting a signal according to a mechanical property of the sheet, the signal output unit being provided on at least one of the impact applying unit side and the impact receiving unit side,
wherein the impact applied to the sheet by the impact applying unit causes the bending of the sheet, whereby the sheet and the impact receiving unit are made to come into contact with each other, to output the signal from the signal output unit, and
a conveying means which conveys a sheet; and
an image forming means for forming an image on the sheet,
wherein the image forming means is controlled by using an output signal from the signal output unit of the signal output apparatus and a memory unit in which information on sheets is stored.

20. The image forming apparatus according to claim 19, further comprising fixing means for fixing on the sheet a toner image formed by the image forming means, wherein the fixing means is controlled by using an output signal from the signal output unit.

21. The image forming apparatus according to claim 20, wherein the controlling of the fixing means includes controlling the amount of ink to be discharged toward the sheet.

22. An image forming apparatus, which comprises a signal output apparatus comprising:
an impact applying unit for applying an impact to a sheet;
an impact receiving unit for receiving the impact through the sheet; and
a plurality of signal output units for outputting a signal according to a mechanical property of the sheet, the signal output units being provided on at least one of the impact applying unit side and the impact receiving unit side, wherein the impact applied to the sheet by the impact applying unit causes the bending of the sheet, whereby the sheet and the impact receiving unit are made to come into contact with each other, to output the signal from a signal output unit of the plurality of signal output units;

a conveying means which conveys a sheet and an image forming means for forming an image on the sheet.

23. A sheet conveying apparatus comprising:

a signal output apparatus comprising:

an impact applying unit for applying an impact to a sheet;

an impact receiving unit for receiving the impact through the sheet; and a signal output unit for outputting a signal according to a mechanical property of the sheet, the signal output unit being provided on at least one of the impact applying unit side and the impact receiving unit side, wherein the impact applied to the sheet by the impact applying unit causes the bending of the sheet, whereby the sheet and the impact receiving unit are made to come into contact with each other, to output the signal from the signal output unit; and conveying means for conveying a sheet, wherein a conveying condition in the conveying means is determined by using a signal from the signal output unit in the signal output apparatus.

24. A signal output method comprising the steps of:

making a sheet exist between an impact applying unit and an impact receiving unit, applying an impact to the sheet to cause the bending of the sheet, whereby the sheet and the impact receiving unit are made to come in contact with each other at a position opposite to the impact applying unit, to output a signal according to a mechanical property of the sheet.

25. A signal output method comprising the step of applying an impact to a sheet with an impact applying unit to bend the sheet toward a recess provided at a position opposite to the impact applying unit, whereby the sheet and an impact receiving unit are made to come into contact with each other at the position, to output a signal according to a mechanical property of the sheet.

* * * * *

UNITED STATES PATENT AND TRADEMARK OFFICE
CERTIFICATE OF CORRECTION

PATENT NO.      : 7,426,062 B2
APPLICATION NO. : 10/760293
DATED           : September 16, 2008
INVENTOR(S)     : Hidetoshi Nojiri et al.

It is certified that error appears in the above-identified patent and that said Letters Patent is hereby corrected as shown below:

COLUMN 2
Line 3, "out put" should read --output--.

COLUMN 3
Line 39, "a" should read --an--.

COLUMN 5
Line 29, "invention." should read --invention;--.

COLUMN 9
Line 55, "placed" should read --placed on--.

COLUMN 10
Line 43, "front" should read --the front--.
Line 65, "Pb(Mg." should read --Pb((Mg.--.

COLUMN 11
Line 3, "semiconductor)" should read --a semiconductor--.
Line 60, "(S3-4)" should read --(S3-4).--.

COLUMN 16
Line 44, "off" should read --of--.

COLUMN 18
Line 59, "then" should read --than--.

COLUMN 19
Line 29, "vibration." should read --vibration).--.

COLUMN 21
Line 3, "create" should read --creates--.

UNITED STATES PATENT AND TRADEMARK OFFICE
CERTIFICATE OF CORRECTION

PATENT NO. : 7,426,062 B2
APPLICATION NO. : 10/760293
DATED : September 16, 2008
INVENTOR(S) : Hidetoshi Nojiri et al.

It is certified that error appears in the above-identified patent and that said Letters Patent is hereby corrected as shown below:

COLUMN 22
Line 23, "resistor" should read --a resistor--.

COLUMN 24
Line 18, "toner) In" should read --toner). In--.

COLUMN 36
Line 23, "grove" should read --groove--.
Line 45, "grove" should read --groove--.
Line 62, "Co.," should read --Co,--.

COLUMN 38
Line 42, "lower" should read --lower than--.

COLUMN 41
Line 52, "comprises" should read --comprises:--.

COLUMN 42
Line 19, "thereof;" should read --thereof; and--.
Line 36, "claim 5," should read --claim 6--.

COLUMN 42
Line 43, "type of sheet" should read --sheet type--.

COLUMN 44
Line 30, "a signal output apparatus comprising:" should be deleted.

COLUMN 45
Line 5, "units;" should read --units, and--.
Line 22, "unit; and" should read --unit, and--.

UNITED STATES PATENT AND TRADEMARK OFFICE
CERTIFICATE OF CORRECTION

PATENT NO. : 7,426,062 B2
APPLICATION NO. : 10/760293
DATED : September 16, 2008
INVENTOR(S) : Hidetoshi Nojiri et al.

It is certified that error appears in the above-identified patent and that said Letters Patent is hereby corrected as shown below:

COLUMN 46
Line 7, "unit" should read --unit; and--.

Signed and Sealed this

Twelfth Day of May, 2009

JOHN DOLL
*Acting Director of the United States Patent and Trademark Office*